(12) United States Patent
Wang et al.

(10) Patent No.: US 10,776,998 B1
(45) Date of Patent: Sep. 15, 2020

(54) METHOD AND SYSTEM FOR ANALYSIS OF 3D DEFORMATIONS AND REGIONAL FUNCTION OF A HEART WITH 3D SINMOD

(71) Applicant: University of Louisville Research Foundation, Inc., Louisville, KY (US)

(72) Inventors: Hui Wang, Louisville, KY (US); Amir A. Amini, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 14/635,900

(22) Filed: Mar. 2, 2015

Related U.S. Application Data

(60) Provisional application No. 61/946,493, filed on Feb. 28, 2014.

(51) Int. Cl.
| | |
|---|---|
| *A61B 5/055* | (2006.01) |
| *G01R 33/56* | (2006.01) |
| *G01R 33/36* | (2006.01) |
| *G06T 17/00* | (2006.01) |
| *A61B 5/11* | (2006.01) |
| *A61B 5/02* | (2006.01) |
| *G06T 15/08* | (2011.01) |

(52) U.S. Cl.
CPC ............... *G06T 17/00* (2013.01); *A61B 5/02* (2013.01); *A61B 5/055* (2013.01); *A61B 5/1102* (2013.01); *G01R 33/56* (2013.01); *G01R 33/5607* (2013.01); *G06T 15/08* (2013.01); *A61B 2576/023* (2013.01); *G06T 2207/10012* (2013.01); *G06T 2207/10088* (2013.01); *G06T 2207/30048* (2013.01)

(58) Field of Classification Search
CPC ..... A61B 5/055; G01R 33/56; G01R 33/3607
See application file for complete search history.

(56) References Cited

U.S. PATENT DOCUMENTS

2011/0270079 A1\* 11/2011 Osman ................... A61B 5/702
600/421

OTHER PUBLICATIONS

Wang, MR Imaging of Left-Ventricular Function: Novel Image Acquisition and Analysis Techniques, Dec. 2012, University of Louisville, ProQuest Dissertations Publishing, pp. i-160.\*
Arts et al., Mapping Displacement and Deformation of the Heart With Local Sine-Wave Modeling, May 2010, IEEE Transactions on Medical Imaging, vol. 29, No. 5, pp. 1114-1123.\*

(Continued)

*Primary Examiner* — Matthew Salvucci
(74) *Attorney, Agent, or Firm* — Jenkins, Wilson, Taylor & Hunt, P.A.

(57) ABSTRACT

A system and method for analysis of 3D deformations and regional function of a heart includes: a magnetic resonance imaging (MRI) scanner configured to acquire three tagged volume data series with mutually perpendicular tag lines of a heart; a data storage device in communication with the MRI scanner and configured to store the three tagged volume data series; and an image processing machine in communication with data storage device. The image processing machine is configured to: model an intensity distribution around each voxel of each tagged volume data series as a moving sine wave front with a local frequency and an amplitude; and determine a phase and frequency for each voxel from the local frequency and amplitude and a displacement from a quotient of a phase difference and the local frequency.

12 Claims, 74 Drawing Sheets
(68 of 74 Drawing Sheet(s) Filed in Color)

(56) References Cited

OTHER PUBLICATIONS

Rutz et al., Accelerated Whole-Heart 3D CSPAMM for Myocardial Motion Quantification, Mar. 27, 2008, Magnetic Resonance in Medicine, vol. 59, Issue 4, pp. 755-763.*

Arts et al. (2010) Mapping displacement and deformation of the heart with local sine wave modeling. IEEE Transactions on Medical Imaging. 29(5):1114-1123.

Axel et al. (1989) Heart wall motion: improved method of spatial modulation of magnetization for MR imaging. Radiology. 172(2):349-350.

Axel et al. (1989) MR imaging of motion with spatial modulation of magnetization. Radiology. 171(3):841-845.

Deng et al. (2004) Three-dimensional myocardial strain reconstruction from tagged MRI using a cylindrical B-spline model. IEEE Transactions on Medical Imaging. 23(7):861-867.

Moore et al. (2000) Three dimensional systolic strain patterns in the normal human left ventricle: Characterization with tagged MR imaging. Radiology. 214(2):453-466.

Pan et al. (2005) Fast tracking of cardiac motion using 3D-HARP. IEEE Transactions on Biomedical Engineering. 52(8):1425-1435.

Sampath et al. (2003) Real-time imaging of two-dimensional cardiac strain using a harmonic phase magnetic resonance imaging (HARP-MRI) pulse sequence. Magnetic Resonance in Medicine. 50(1):154-163.

Tustison et al. (2003) Myocardial kinematics from tagged MRI based on a 4-D B-spline model. IEEE Transactions on Biomedical Engineering. 50(8):1038-1040.

Tustison et al. (2006) Biventricular myocardial strains via non-rigid registration of anatomical NURBS models. IEEE Transactions on Medical Imaging. 25(1):94-112.

Wang et al. (2013) Cardiac deformation analysis using 3D sinmod from 3D CSPAMM tagged MRI. Proceedings of SPIE Medical Imaging 2013. Biomedical Applications in Molecular, Structural, and Functional Imaging.

Xu et al. (2010) Deformation analysis of 3D tagged cardiac images using an optical flow method. Journal of Cardiovascular Magnetic Resonance. 12:19.

\* cited by examiner

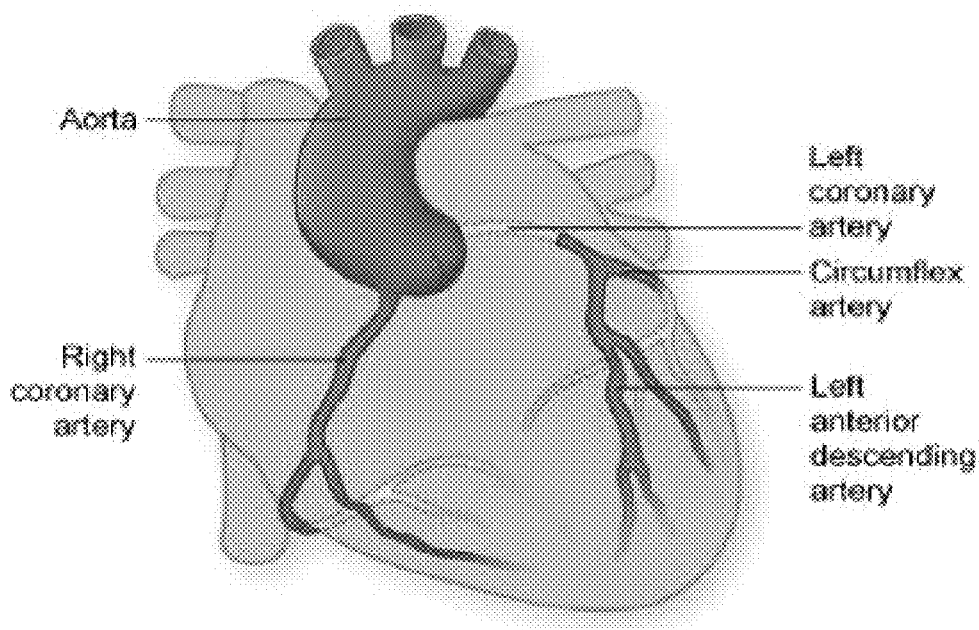
FIG. 2
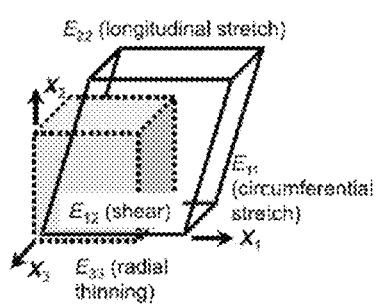  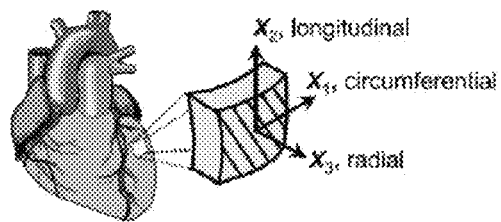
FIG. 3   FIG. 4

METHOD AND SYSTEM FOR ANALYSIS OF 3D DEFORMATIONS AND REGIONAL FUNCTION OF A HEART WITH 3D SINMOD

RELATED APPLICATIONS

This application claims priority to U.S. Provisional Patent Application No. 61/946,493, filed Feb. 28, 2014, the entire disclosure of which is incorporated herein by reference.

STATEMENT REGARDING FEDERALLY SPONSORED RESEARCH OR DEVELOPMENT

Not applicable.

TECHNICAL FIELD

The presently-disclosed subject matter relates to analysis of cardiac deformations and strain. In particular, the presently-disclosed subject matter relates to a method and system for analysis of 3D deformations and regional function of the left-ventricular myocardium with 3D SinMod.

BACKGROUND

Globally, cardiovascular diseases (CVD) are the number one cause of death and are projected to remain so. An estimated 17 million people died from CVD in 2005, representing 30% of all global deaths. Of these deaths, 7.2 million were due to heart attacks and 5.7 million were due to stroke. If current trends continue, by 2030 an estimated 23.6 million people will die from cardiovascular diseases in the world. In America, an estimated 80 million adults (more than one in three) have one or more types of cardiovascular diseases. In 2005, about 864,000 people died of CVD, accounting for 35.3% of all deaths.

Magnetic Resonance Imaging (MRI) is a noninvasive imaging technique with the capability to monitor and assess the progression of CVD so that effective procedures for the care and treatment of patients can be developed by physicians and researchers. It is capable of providing 3D analysis of global and regional cardiac function with great accuracy and reproducibility. MRI can provide three-dimensional analysis of global and regional cardiac function with great accuracy and reproducibility. Compared to ultrasound and X-ray CT, the advantages of MRI are: 1) It is noninvasive and uses non-ionizing radiation; 2) It has 3D and 4D imaging capabilities with high spatial and temporal resolutions and with good soft tissue contrast; 3) It can image the heart at arbitrary orientations; 4) It is valuable in diagnosing a broad range of conditions; 5) It is able to evaluate both the structure and function of the heart. There are also some disadvantages to MRI: it is not real-time, it is expensive, and compared to X-ray CT and ultrasound, has lower resolution.

Many approaches have been proposed for tracking cardiac motion and for computing deformation parameters and mechanical properties of the heart from a variety of cardiac MR imaging techniques.

BRIEF SUMMARY OF THE INVENTION

According to one aspect of the invention, a method for analysis of 3D deformations and regional function of a heart includes: receiving, by an image processing machine, three tagged volume data series with mutually perpendicular tag lines of a heart; modeling, using the image processing machine, an intensity distribution around each voxel of each tagged volume data series as a moving sine wave front with a local frequency and an amplitude; and determining, using the image processing machine, a phase and frequency for each voxel from the local frequency and amplitude and a displacement from a quotient of a phase difference and the local frequency.

In one implementation, each of the three tagged volume data series is acquired, by a magnetic resonance imaging (MRI) scanner, using a 3D complementary spatial modulation of magnetization (CSPAMM) tagging technique. The 3D CSPAMM tagging technique may include rotating, by the MRI scanner, a tagging gradient in such a way as to acquire 3D+t data with orthogonal tags.

In another implementation, the moving sine wave front is formulated as:

$$V_1(x, y, z) = A_1 \cos\left(\omega_x\left(x + \frac{u}{2}\right) + \varphi\right) + n_1(x, y, z)$$

$$V_2(x, y, z) = A_2 \cos\left(\omega_x\left(x - \frac{u}{2}\right) + \varphi\right) + n_2(x, y, z)$$

wherein: $\omega_x$ and $\varphi$ are the spatial frequency and phase of the wave, respectively; $A_1$ and $A_2$ are wave magnitudes for a 3D volume $V_1$ and a short time later, a 3D volume $V_2$; $n_1$ and $n_2$ are additive noise; and u is the displacement between these two volumes at position (x, y, z) along the x direction; and wherein the displacements v and w in they and z directions have a corresponding formulation.

Determining the phase and frequency for each voxel and the displacement may comprise: Fourier transforming, by the processing device, the 3D volume $V_1(x, y, z)$ and the 3D volume $V_2(x, y, z)$ in a first tagging direction; applying, by the processing device, identical 3D band-pass filters to the Fourier-transformed volumes to isolate corresponding spectral peaks and produce two complex volumes in the Fourier domain, $V_{bf1}(\omega_x, \omega_y, \omega_z)$ and $V_{bf2}(\omega_x, \omega_y, \omega_z)$; applying, by the processing device, a low frequency band-pass filter and a high frequency band-pass filter to the two complex volumes in the Fourier domain, followed by an inverse Fourier transform to produce four complex volumes, $V_{bfLf1}(x, y, z)$, $V_{bfHf1}(x, y, z)$, $V_{bFLf2}(x, y, z)$, and $V_{bfHf2}(x, y, z)$; determining, by the processing device, the power spectra and cross power spectrum given by:

$$P_{Lf}(x,y,z)=|V_{bfLf1}|^2+|V_{bfLf2}|^2$$

$$P_{Hf}(x,y,z)=|V_{bfHf1}|^2+|V_{bfHf2}|^2$$

$$P_{cc}(x,y,z)=V_{bfLf1}\overline{V}_{bfLf2}+V_{bfHf1}\overline{V}_{bfHf2}$$

where $\overline{V}$ is the complex conjugate of V; determining, by the processing device, the local frequency $\omega_x$ and local displacement u from:

$$\omega_x(x, y, z) = \omega_c \sqrt{\frac{P_{Hf}}{P_{Lf}}}$$

$$u(x, y, z) = \frac{\arg(P_{cc})}{\omega_x}$$

where $\omega_c$ is the band-pass center-frequency; up-sampling, by the processing device, the local displacement to the initial size of the volume; and repeating the same steps for the other tagging directions to produce full 3D displacements.

According to another aspect of the invention, a system for analysis of 3D deformations and regional function of a heart includes: a magnetic resonance imaging (MRI) scanner configured to acquire three tagged volume data series with mutually perpendicular tag lines of a heart; a data storage device in communication with the MRI scanner and configured to store the three tagged volume data series; and an image processing machine in communication with data storage device. The image processing machine is configured to: model an intensity distribution around each voxel of each tagged volume data series as a moving sine wave front with a local frequency and an amplitude; and determine a phase and frequency for each voxel from the local frequency and amplitude and a displacement from a quotient of a phase difference and the local frequency.

In one implementation, the MRI scanner acquires each of the three tagged volume data series using a 3D complementary spatial modulation of magnetization (CSPAMM) tagging technique. The MRI scanner, performing the 3D CSPAMM tagging technique, may rotate a tagging gradient in such a way as to acquire 3D+t data with orthogonal tags.

In another implementation, the image processing machine formulates the moving sine wave front as:

$$V_1(x, y, z) = A_1 \cos\left(\omega_x\left(x + \frac{u}{2}\right) + \varphi\right) + n_1(x, y, z)$$

$$V_2(x, y, z) = A_2 \cos\left(\omega_x\left(x - \frac{u}{2}\right) + \varphi\right) + n_2(x, y, z)$$

wherein: $\omega_x$ and $\varphi$ are the spatial frequency and phase of the wave, respectively; $A_1$ and $A_2$ are wave magnitudes for a 3D volume $V_1$ and a short time later, a 3D volume $V_2$; $n_1$ and $n_2$ are additive noise; and u is the displacement between these two volumes at position (x, y, z) along the x direction; and wherein the displacements v and w in they and z directions have a corresponding formulation.

The image processing machine may determine the phase and frequency for each voxel and the displacement by: Fourier transforming the 3D volume $V_1(x, y, z)$ and the 3D volume $V_2(x, y, z)$ in a first tagging direction; applying identical 3D band-pass filters to the Fourier-transformed volumes to isolate corresponding spectral peaks and produce two complex volumes in the Fourier domain, $V_{bf1}(\omega_x, \omega_y, \omega_z)$ and $V_{bf2}(\omega_x, \omega_y, \omega_z)$; applying a low frequency band-pass filter and a high frequency band-pass filter to the two complex volumes in the Fourier domain, followed by an inverse Fourier transform to produce four complex volumes, $V_{bfLf1}(x, y, z)$, $V_{bfHf1}(x, y, z)$, $V_{bfLf2}(x, y, z)$, and $V_{bfHf2}(x, y, z)$; determining the power spectra and cross power spectrum given by:

$$P_{Lf}(x,y,z)=|V_{bfLf1}|^2+|V_{bfLf2}|^2$$

$$P_{Hf}(x,y,z)=|V_{bfHf1}|^2+|V_{bfHf2}|^2$$

$$P_{cc}(x,y,z)=V_{bfLf1}\bar{V}_{bfLf2}+V_{bfHf1}\bar{V}_{bfHf2}$$

where $\bar{V}$ is the complex conjugate of V; determining the local frequency $\omega_x$ and local displacement u from:

$$\omega_x(x, y, z) = \omega_c \sqrt{\frac{P_{Hf}}{P_{Lf}}}$$

$$u(x, y, z) = \frac{\arg(P_{cc})}{\omega_x}$$

where $\omega_x$ is the band-pass center-frequency; up-sampling the local displacement to the initial size of the volume; and repeating the same steps for the other tagging directions to produce full 3D displacements.

Further advantages of the presently-disclosed subject matter will become evident to those of ordinary skill in the art after a study of the description, Figures, and non-limiting Examples in this document.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 is a schematic representation of a heart showing coronary circulation.

FIG. 3 is a schematic diagram showing components of a strain tensor of a cardiac deformation along directions $E_{11}$, $E_{12}$, $E_{22}$, and $E_{33}$.

FIG. 4 is a schematic diagram showing cardiac deformation along directions $X_1$, $X_2$, and $X_3$.

FIG. 7—Right is a timing diagram showing state of magnetization as a function of time.

FIG. 19(*b*) is an exemplary displacement field with non-homogeneous translations in x, y, and z directions in a simulated sequence, where the first row displays a 3D visualization and the second row is the 2D projection of the first row. FIG. 19(*c*) is an exemplary contraction displacement field in a simulated sequence, where the first row displays a 3D visualization and the second row is the 2D projection of the first row.

FIG. 22(*b*) is a 3-D graph of mid-wall contours tracked by 3D SinMod at end-systole. FIG. 22(*c*) is a 3-D graph of mid-wall contours tracked by 3D SinMod at the end-diastole.

FIG. 38(*b*) is a graph showing calculated circumferential shortening percentage for slice 3 of data set 1. FIG. 38(*c*) is a graph showing calculated circumferential shortening percentage for slice 4 of data set 1. FIG. 38(*d*) is a graph showing calculated circumferential shortening percentage for slice 5 of data set 1. FIG. 38(*e*) is a graph showing calculated circumferential shortening percentage for slice 6 of data set 1. FIG. 38(*f*) is a graph showing calculated circumferential shortening percentage for slice 7 of data set 1.

FIG. 39(*b*) is a graph showing calculated circumferential shortening percentage for slice 9 of data set 1. FIG. 39(*c*) is a graph showing calculated circumferential shortening percentage for slice 10 of data set 1.

FIG. 40(*b*) is a graph showing calculated circumferential shortening percentage for slice 3 of data set 2. FIG. 40(*c*) is a graph showing calculated circumferential shortening percentage for slice 4 of data set 2. FIG. 40(*d*) is a graph showing calculated circumferential shortening percentage for slice 5 of data set 2. FIG. 40(*e*) is a graph showing calculated circumferential shortening percentage for slice 6 of data set 2. FIG. 40(*f*) is a graph showing calculated circumferential shortening percentage for slice 7 of data set 2.

FIG. 41(*b*) is a graph showing calculated circumferential shortening percentage for slice 9 of data set 2. FIG. 41(*c*) is a graph showing calculated circumferential shortening percentage for slice 10 of data set 2.

FIG. 42(*b*) is a graph showing calculated circumferential shortening percentage for slice 3 of data set 3. FIG. 42(*c*) is a graph showing calculated circumferential shortening percentage for slice 4 of data set 3. FIG. 42(*d*) is a graph showing calculated circumferential shortening percentage for slice 5 of data set 3. FIG. 42(*e*) is a graph showing calculated circumferential shortening percentage for slice 6 of data set 3. FIG. 42(*f*) is a graph showing calculated circumferential shortening percentage for slice 7 of data set 3.

FIG. 43(*b*) is a graph showing calculated circumferential shortening percentage for slice 9 of data set 3. FIG. 43(*c*) is a graph showing calculated circumferential shortening percentage for slice 10 of data set 3.

FIG. 54(a) to FIG. 54(f) are respective results for basal anterior (segment 1), basal antero-septal (segment 2), basal infero-septal (segment 3), basal inferior (segment 4), basal posterior (segment 5), basal lateral (segment 6).

FIG. 55(a) to FIG. 55(f) are respective results for mid-ventricular anterior (segment 7), mid-ventricular antero-septal (segment 8), mid-ventricular infero-septal (segment 9), mid-ventricular inferior (segment 10), mid-ventricular posterior (segment 11), mid-ventricular lateral (segment 12).

FIG. 56(a) to FIG. 56(e) are respective results for apical anterior (segment 13), apical septal (segment 14), apical inferior (segment 15), apical lateral (segment 16), and apex (segment 17).

DETAIL DESCRIPTION OF EXEMPLARY EMBODIMENTS

Figure 1:
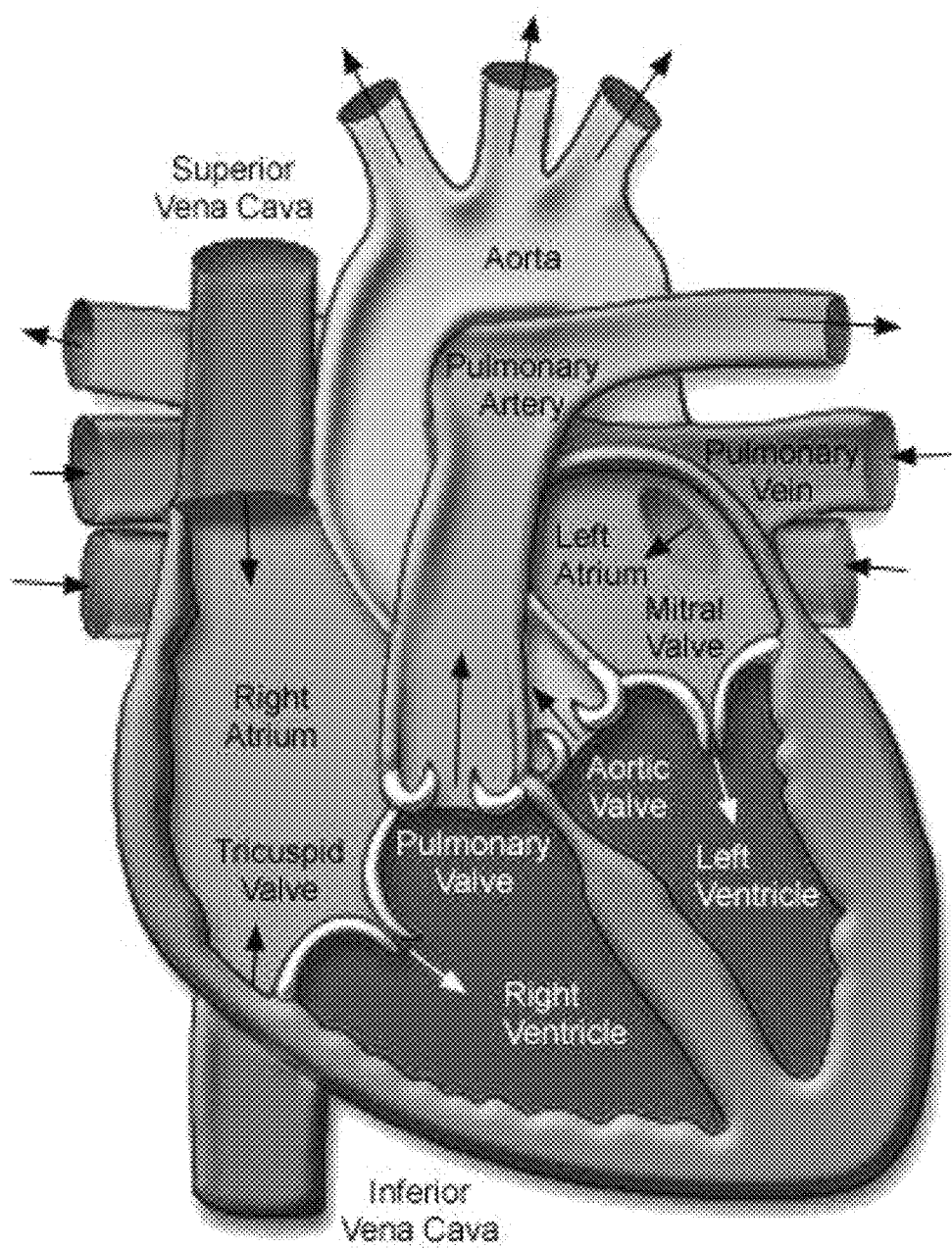
FIG. 1 is a schematic representation of the anatomy of a heart.

The details of one or more embodiments of the presently-disclosed subject matter are set forth in the attachments to this document. Modifications to embodiments described in these attachments, and other embodiments, will be evident to those of ordinary skill in the art after a study of the information provided in these attachments. The information provided in these attachments, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "image processing machine" is used herein to describe one or more microprocessors, microcontrollers, central processing units, Digital Signal Processors (DSPs), Field-Programmable Gate Arrays (FPGAs), Application-Specific Integrated Circuits (ASICs), or the like for executing instructions stored on a data storage device.

The term "data storage device" is understood to mean physical devices (computer readable media) used to store programs (sequences of instructions) or data (e.g. program state information) on a non-transient basis for use in a computer or other digital electronic device, including primary memory used for the information in physical systems which are fast (i.e. RAM), and secondary memory, which are physical devices for program and data storage which are slow to access but offer higher memory capacity. Traditional secondary memory includes tape, magnetic disks and optical discs (CD-ROM and DVD-ROM). The term "memory" is often (but not always) associated with addressable semiconductor memory, i.e. integrated circuits consisting of silicon-based transistors, used for example as primary memory but also other purposes in computers and other digital electronic devices. Semiconductor memory includes both volatile and non-volatile memory. Examples of non-volatile memory include flash memory (sometimes used as secondary, sometimes primary computer memory) and ROM/PROM/EPROM/EEPROM memory. Examples of volatile memory include dynamic RAM memory, DRAM, and static RAM memory, SRAM.

1. Cardiac Anatomy

The heart is a muscular cone-shaped organ located in the upper body between the lungs [1]. The essential function of the heart is to pump blood around the body. The heart is divided into separate right and left sections by the interventricular septum, as shown in FIG. 1. Each of these (right and left) sections is also divided into upper and lower compartments known as atria and ventricles, respectively. The four chambers for the mammalian heart are: right atrium (RA), right ventricle (RV), left atrium (LA), and left ventricle (LV). The two atria act as collecting reservoirs for blood returning to the heart while the two ventricles act as pumps to eject the blood to the body. Deoxygenated blood returns to the heart via the major veins (superior and inferior vena cava), enters the right atrium, passes into the right ventricle, and from there is ejected into the pulmonary artery on the way to the lungs. Oxygenated blood returning from the lungs enters the left atrium via the pulmonary veins, passes into the left ventricle, and is then ejected into the aorta. As in any pumping system, there are four valves to prevent the back flow of blood. The tricuspid valve is between the right atrium and right ventricle. The pulmonic valve is between the right ventricle and pulmonary artery. The mitral valve is between the left atrium and left ventricle and the aortic valve is between the left ventricle and the aorta.

Cardiac cycle refers to the events of one complete heartbeat. In normal adults, the length of the cardiac cycle is usually about 0.8 second. The cardiac cycle consists of two phases: systole and diastole. During diastole the ventricles are filled and the atria contract. Then during systole, the ventricles contract while the atria are relaxed and filled. In detail, the pumping action starts with the simultaneous contraction of the two atria. This contraction gives an added push to get the flood into the ventricles during diastole. Shortly after that, the ventricles contract, signifying the beginning of systole. The aortic and pulmonic valves open and blood is ejected from the ventricles, while the mitral and tricuspid valves close to prevent back flow. At the same time, the atria start to fill with blood again. After a while, the ventricles relax, the aortic and pulmonic valves close, the mitral and tricuspid valves open, and the ventricles start to fill with blood again, signifying the end of systole and the beginning of diastole. In a normal ECG waveform over an R-R interval, the P wave indicates the activation of atria, corresponding to their contraction. The QRS complex indicates the activation of the ventricles. Both P and QRS are known as depolarization waves. T wave indicates the ventricular recovery (repolarization wave). Systole covers the period from the onset of QRS complex to the end of T wave. The remaining part of a cardiac cycle is diastole. In cardiac MRI, where imaging typically requires synchronization with the ECG, the pulse sequence is triggered when the amplitude of the R wave reaches its maximum. This can be determined either by threshold detection or peak-slope detection.

Another important concept is the coronary circulation [1], from which the heart receives the energy and nourishment it needs (FIG. 2), which resides on the epicardial (outer) surface of the heart. Coronary circulation refers to the blood circulation in the vessels of the heart muscle. Because the myocardium is very thick, it requires coronary blood vessels to deliver blood deep into it. The aorta branches off into two main coronary blood vessels: the right coronary artery (RCA) and the left coronary artery (LCA) which divides into left anterior descending and circumflex branches. These vessels deliver oxygen-rich blood to the myocardium.

2. Stress and Strain

The primary function of the heart is fundamentally mechanical [2]. The basic measurements of myocardial mechanics are the three-dimensional stresses and strains, which depend on position and orientation in the myocardium and vary in time throughout the cardiac cycle. The terms "strain" and "stress" are often used together in cardiology. But they are different physical quantities with distinct units. Stress is defined as force per unit area, so it has the same unit $F/m^2$ as pressure. In cardiology, stress is interaction forces acting across surfaces between adjacent regions of muscle, while strain represents the change of shape at any point in the wall between the original reference state and the subsequent deformed state, which is dimensionless [2].

The matrix components of the stress and strain tensors depend on the selected frame of reference. It is conventional to choose the orthogonal system, such as the local circumferential, longitudinal, and radial axes, as shown in FIG. 3 and FIG. 4.
1. Normal (Axial) Stress: stress that acts perpendicular to a surface. It can be either compressional or tensional.
2. Shear Stress: stress that acts parallel to a surface. It can cause one object to slide over another. It also tends to deform originally rectangular objects into parallelograms. The most general definition is that shear acts to change the angles in an object.

Ventricular wall stress and strain are inhomogeneous. Their components can change significantly from place to place in the myocardium. This heterogeneity makes understanding ventricular mechanics a significant challenge, but also gives tagged MRI an opportunity to stand out from other techniques in measuring strains. Development of tagged MRI was a major milestone in the field of cardiac mechanics. The tagged MRI technique will be discussed in detail later.

Figure 5:
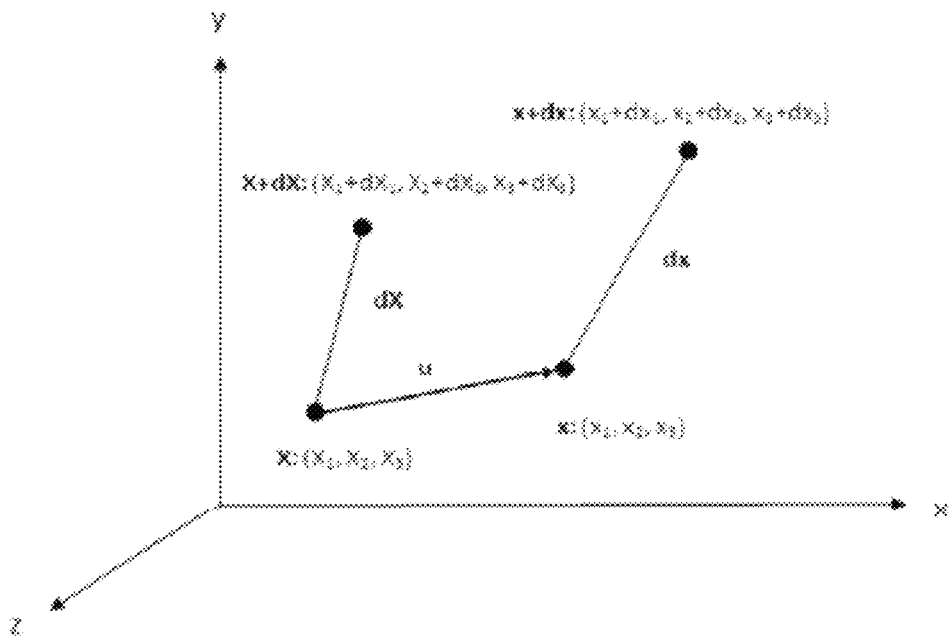
FIG. 5 is a schematic diagram showing displacement of a point during deformation.

Regional myocardial stress and strain have direct or indirect relationship with cardiac diseases. At present, regional strain distribution measurement is much more practical than the stress measurement. For measuring systolic function, end-diastole is a conventional unstrained reference state. An illustration of the relationship between the initial (initial, reference, and undeformed configurations are interchangeable throughout this section) and deformed configuration is shown in FIG. 5. Suppose a material point at position $X:(X_1, X_2, X_3)$ in the undeformed solid moves to a new position $x:(x_1, x_2, x_3)$ when the solid is loaded. A mapping $x=\chi(X, t)$ would describe the motion. The displacement of the material point u is $$u(t)=x(t)-X \quad (1)$$

One measurement of the deformation in the reference configuration is the length change of a segment dX at point X:

$$dx=\chi(X+dX)-\chi(X)\approx[\nabla\chi(X)]\cdot dX=F\cdot dX \quad (2)$$

where $\nabla$ is gradient operator and F is the deformation gradient at X. According to chain rule, the relationship between dx in deformed configuration and dX in reference configuration is:

$$dx_i = \frac{\partial x_i}{\partial X_j} dX_j \quad (3)$$

The mapping in the above equation is called deformation gradient tensor (DGT) $F_{ij}$.

$$F_{ij} = \frac{\partial x_i}{\partial X_j} \quad (4)$$

The matrix form of deformation gradient tensor is:

$$F = \begin{bmatrix} F_{11} & F_{12} & F_{13} \\ F_{21} & F_{22} & F_{23} \\ F_{31} & F_{32} & F_{33} \end{bmatrix} = \begin{bmatrix} \frac{\partial x_1}{\partial X_1} & \frac{\partial x_1}{\partial X_2} & \frac{\partial x_1}{\partial X_3} \\ \frac{\partial x_2}{\partial X_1} & \frac{\partial x_2}{\partial X_2} & \frac{\partial x_2}{\partial X_3} \\ \frac{\partial x_3}{\partial X_1} & \frac{\partial x_3}{\partial X_2} & \frac{\partial x_3}{\partial X_3} \end{bmatrix} \quad (5)$$

From Equation (1), we have:

$$x_i = X_i + u_i \quad (6)$$

Taking the derivative of the above equation with respect to $X_1$, $X_2$, and $X_3$ and writing in matrix form in terms of the displacement field u, F becomes $$F = \begin{bmatrix} 1 & 0 & 0 \\ 0 & 1 & 0 \\ 0 & 0 & 1 \end{bmatrix} + \begin{bmatrix} \frac{\partial u_1}{\partial X_1} & \frac{\partial u_1}{\partial X_2} & \frac{\partial u_1}{\partial X_3} \\ \frac{\partial u_2}{\partial X_1} & \frac{\partial u_2}{\partial X_2} & \frac{\partial u_2}{\partial X_3} \\ \frac{\partial u_3}{\partial X_1} & \frac{\partial u_3}{\partial X_2} & \frac{\partial u_3}{\partial X_3} \end{bmatrix} \quad (7)$$

To find a measure of the change in length of dX, let us define strain:

$$\varepsilon = \frac{1}{2}\frac{|dx|^2 - |dX|^2}{|dX|^2} = \frac{1}{2}\frac{dx^T dx - dX^T dX}{|dX|^2} \quad (8)$$

$$= \frac{1}{2}\frac{(FdX)^T(FdX) - dX^T dX}{|dX|^2}$$

$$= \frac{dX^T \frac{1}{2}(F^T F - I)dX}{|dX|^2}$$

Lagrangian strain tensor (also called Green's strain tensor) E is often used to characterize the infinitesimal deformation at a point.

$$E = \frac{1}{2}(F^T F - I) \quad (9)$$

The normal strain in the direction of the unit vector m can be calculated from the Lagrangian strain tensor through the quadratic form $$n^T E n \quad (10)$$

where n may point to any direction on the unit sphere. Due to the geometry of the ventricle, the normal strains are usually calculated in radial, circumferential, and longitudinal directions (See FIG. 3 and FIG. 4).

Since F is nonsingular, the inverse map, $F^{-1}$, exists and allows for the Eulerian description of strain which is given by $$\varepsilon = \frac{1}{2}\frac{|dx|^2 - |dX|^2}{|dx|^2} = \frac{1}{2}\frac{dx^T dx - dX^T dX}{|dx|^2} \quad (11)$$

$$= \frac{1}{2}\frac{dx^T dx - (F^{-1}dx)F^{-1}dx}{|dx|^2}$$

$$= \frac{dx^T \frac{1}{2}(I - (FF^T)^{-1})dx}{|dx|^2}$$

where G is often called the Eulerian strain tensor which is defined as follows:

$$G = \frac{1}{2}(I - (FF^T)^{-1}) \quad (12)$$

Regional myocardial strains have direct or indirect relationship with cardiac diseases. Most of the motion tracking and analysis methods aim to extract strains in the heart, for the reason that strain encapsulates the basic mechanical function of the myocardium and has clinical potential. This invention is concerned with novel MR imaging techniques and image postprocessing methods to analyze left ventricular deformations.

3. Basic Principles of MRI

The magnetic resonance phenomenon can be described by both microscopic and macroscopic perspectives. The microscopic perspective explains the fundamental behavior of the net magnetization of spinning protons within a strong magnetic field when external energy is added by a short-duration radio frequency (RF) pulse. Once the fundamentals are understood, the formation of MR signals is more easily described by a macroscopic perspective, where the effect of the RF pulse is to move spins from a lower energy state to a higher energy state. In a vector model, this corresponds to transverse magnetization, which normally is zero, having a non-zero value. A detectable MR signal is only possible from components of the transverse magnetization. By applying current through RF coils surrounding the sample, the spin system can be deliberately excited using RF pulses so that the stimulated system will in turn induce RF signals as output. When the RF pulse is turned off, spins relax back to an equilibrium state. The time constant for decay of transverse magnetization is called $T_2$ relaxation. Longitudinal relaxation, also called $T_1$ relaxation, governs the process of return of spins from high energy state to the low energy state. In order to detect the emitted signal, an RF coil is placed close to the object. Farady's Law states that when the magnetic flux enclosed by a loop of wire changes with time, current is produced in the loop, thus inducing a voltage. In fact, this is precisely why the net magnetization needs to be tipped into transverse plane. The free induction decay (FID) signal however is from the entire sample. The MR signal needs to be distinguished in local groups of voxels in order to make an image.

In 1973, Lauterbur [3] proposed the use of magnetic field gradients for spatial localization of MR signals which laid the foundation for magnetic resonance imaging. When the gradient fields are turned on, precessional frequencies of the spins become linearly dependent on their spatial locations. The frequency and the phase of the precessing magnetization are measured by an RF receiver coil. The basic approach to MRI performs slice selection, phase encoding, and frequency encoding multiple times to make an image.

4. MR Tagging Techniques for Imaging Cardiac Function

MRI has revolutionized medicine due to its broad ability to image many organ systems. However, in the case of the heart, development of MRI has been hampered because of heart's inherent motion. Myocardial tagging is a technique that is useful in assessing ventricular function.

The fundamental challenges to cardiac MRI are movement of the heart throughout the cardiac cycle and movement of the lungs during the respiratory cycle, both requiring mitigation to avoid motion artifacts. Respiratory motion can be alleviated with breath holding during imaging. The subject is typically asked to hold his/her breath for 10-15 seconds which is typically sufficient to collect a cine at one slice location. It should be noted that in sick patients and/or those unable to hold their breath, navigator-gated acquisition is an alternative. Cardiac gating/triggering provides methods to synchronize data collection with the cardiac rhythm. It is used to minimize the motion artifacts arising from cardiac motion and from flowing blood or cerebrospinal fluid (CSF). The goal is to acquire an entire set of k-space data at approximately the same slice location for the cardiac cycle.

A variety of approaches to gated/triggered data acquisition can be adopted including: electrocardiography (ECG), Vectorcardiogram (VCG), and peripheral gating. However, the methods more widely used to synchronize with cardiac motion essentially rely on the ECG and VCG, since the signal from peripheral devices which provide blood oxygen situation levels are delayed relative to the electrical activity of the heart. There are two types of triggering: prospective triggering and retrospective triggering. Prospective triggering uses the R-wave to determine the starting point of the acquisition. Slices are acquired at the same time after each new R-wave in successive R-R intervals. Artifacts are reduced by keeping slice excitation consistent in relation to the R-peak. In prospective triggering, only one part of the cardiac cycle is imaged. To account for heart rate variability, retrospective triggering, a continuous acquisition method, can be adopted. With retrospective triggering, k-space data are continuously acquired through-out time and retrospectively "binned" relative to the R-wave. The advantage of retrospective triggering is that it permits imaging the entire cardiac cycle, whereas in prospective gating, there is "dead" time at the end of the diastole.

Figure 6:
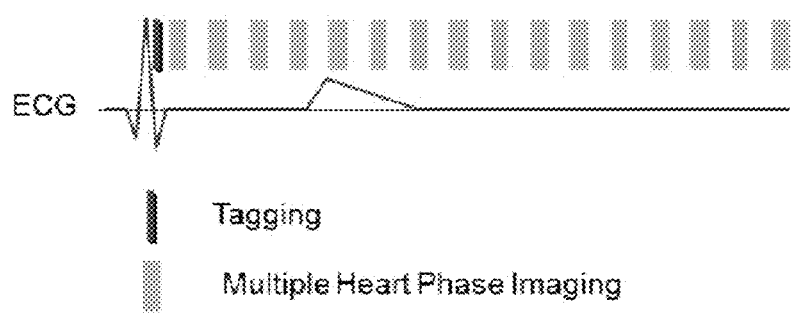
FIG. 6 is a tagging sequence timing diagram.

The process of MR tagging uses a special pulse sequence to spatially modulate the longitudinal magnetization in the imaging volume, prior to image acquisition using conventional imaging, as shown in FIG. 6. The tagging sequence is usually applied immediately after an R-peak. The varying magnetization produces alternating light and dark patterns on the image as noninvasive markers in the tissues. The main reason why tagged MRI can image motion is that when the local magnetization of a material point is altered, the material point maintains the altered magnetization when it moves within the limits of the $T_1$ relaxation time.

Spatial Modulation of Magnetization (SPAMM) [4] is the most commonly used technique to produce sinusoidal tag patterns. Optimal tagging and acquisition of MR images for cardiac motion analysis was investigated by Nguyen et al. [5]. Pai and Axel [6] gave a thorough review of tagged cardiac MR imaging methods, including advances in pulse sequence development, image acquisition, high temporal and spatial resolution imaging, high field strength imaging, and 3D whole heart tagging. A review paper covering clinical applications of myocardial tagging is [7].

Figure 7:
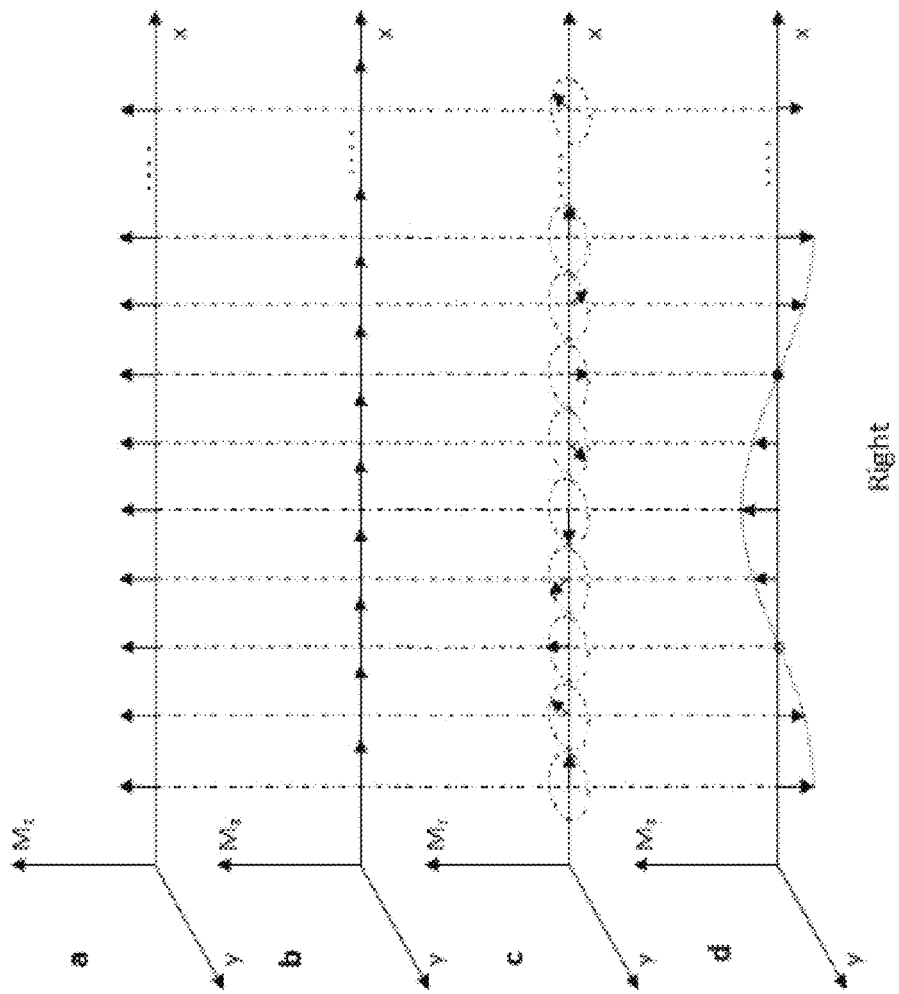
FIG. 7—Left is a timing diagram for a Spatial Modulation of Magnetization (SPAMM) imaging method.
Figure 7:
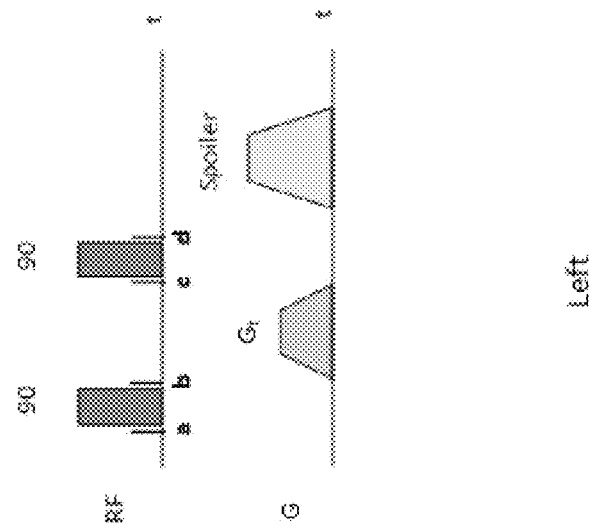

A one-dimensional 1-1 SPAMM sequence is shown in FIG. 7 (Left) which consists of two 90° RF pulses, an interspersed tagging gradient in the readout direction, and a spoiler gradient. Before the first RF pulse, magnetization in rotating frame is initially all polarized along the main magnetic field (in the z direction) (FIG. 7(a)). The first RF pulse flips the initial longitudinal magnetization into the transverse plane (FIG. 7(b)). The tagging gradient $G_t$ produces a periodic spatial modulation of the phase of the transverse magnetization along the gradient direction (FIG. 7(c)). The second RF pulse produces modulated longitudinal magnetization (FIG. 7(d)). The function of the spoiler gradient is to eliminate any remaining transverse magnetization. A tag grid can be produced by following the second RF pulse with a second gradient in a direction orthogonal to the first gradient and then with another RF pulse. In the subsequent imaging step, the spatially modulated longitudinal magnetization is made visible by the excitation RF pulse which flips it to the transverse plane. The tag lines are not sharply changed, but with sinusoidal variation of intensity in the image (FIG. 7(d)). An MR tagged image can be considered to be product of two components. The first component is signal from the anatomy, and the second is the sinusoidal tagging component. Therefore, tagged image produced by the sequence in FIG. 7 amounts to amplitude modulation (AM) of the anatomical image by a carrier frequency prescribed by tagging pulse. Sharper tagging stripes can be obtained by using other binomially distributed RF pulses that are each separated by dephasing gradients [8]. The effect of the SPAMM pulse sequence is to produce a series of stripes in the acquired images. One drawback of SPAMM tagging is that due to $T_1$ relaxation, tags fade in later phases of the cardiac cycle.

Complementary SPAMM (CSPAMM) was introduced by Fischer et al. to improve tagging contrast in later phases of the cardiac cycle [9]. Two SPAMM images which are out of phase by 180° are acquired and subtracted. CSPAMM has the advantage of longer net tag persistence while suppressing untagged blood. In CSPAMM, the longitudinal magnetization M is decomposed into two terms: one for tagging information $Q_T$ and the other for the relaxation part $Q_R$.

Figure 8:
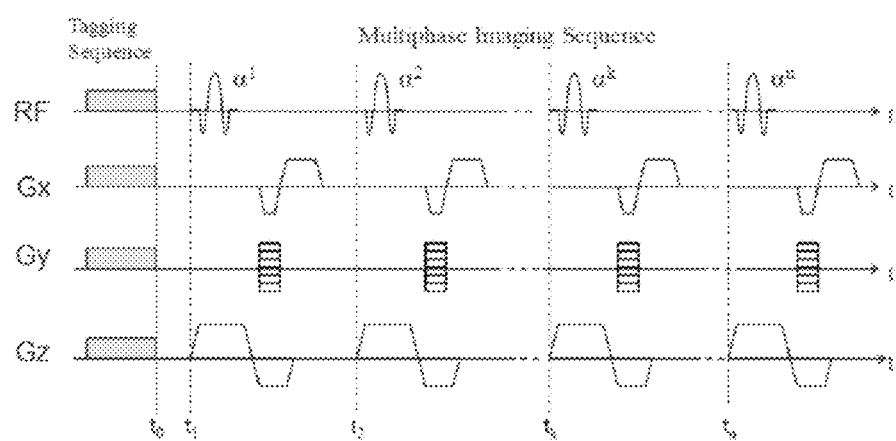
FIG. 8 is a timing diagram of a typical tagging experiment.

FIG. 8 is a timing diagram of a typical tagging experiment. A tagging sequence is applied before $t_0$ followed by a standard multiphase imaging sequence. $t_k$ corresponds to the start of the $k^{th}$ phase in the cardiac cycle. $\alpha^k$ corresponds to the RF pulse flip angle at the $k^{th}$ phase in the cardiac cycle where $\alpha^1 = \ldots \alpha^k = \ldots \alpha^n$. Note that each of the RF pulses $\alpha^1, \alpha^2, \ldots$ is applied multiple times corresponding to different strength of the phase encoding gradient. That creates a single image in the cine sequence.

At time $t_0$ immediately after the SPAMM tagging sequence, the modulated longitudinal magnetization is:

$$M_z(t_0) = M_{ss} TAG(x, y) \quad (13)$$

where $M_{ss}$ is the steady state magnetization before tagging and TAG(x, y) represents a spatially varying sinusoidal function introduced by tagging sequence. At time $t_1 > t_0$, longitudinal magnetization becomes $$M_z(t_1) = (M_z(t_0) - M_0)e^{-t_1/T_1} + M_0 \quad (14)$$
$$= (M_{ss} TAG(x, y) - M_0)e^{-t_1/T_1} + M_0$$
$$= M_{ss} TAG(x, y))e^{-t_1/T_1} + M_0(1 - e^{-t_1/T_1})$$
$$= Q_{T_1} + Q_{R_1}$$

where $M_0$ is the equilibrium magnetization, and $T_1$ is the longitudinal relaxation time. At time $t_k$, $$M_z(t_k) = (M_z(t_{k-1}) - M_0)e^{-(t_k - t_{k-1})/T_1} + M_0 \quad (15)$$
$$= [(Q_{T_{k-1}} + Q_{R_{k-1}})\cos\alpha_{k-1} - M_0]e^{-(t_k - t_{k-1})/T_1} + M_0$$
$$= (Q_{T_{k-1}}\cos\alpha_{k-1} + Q_{R_{k-1}}\cos\alpha_{k-1} - M_0]$$
$$e^{-(t_k - t_{k-1})/T_1} + M_0$$
$$= Q_{T_{k-1}}\cos\alpha_{k-1} e^{-(t_k - t_{k-1})/T_1} +$$
$$(Q_{R_{k-1}}\cos\alpha_{k-1} - M_0)e^{-(t_k - t_{k-1})/T_1} + M_0$$
$$= Q_{T_k} + Q_{R_k}$$

Therefore, the two components of the longitudinal magnetization just before the $k_{th}$ RF pulse are:

$$Q_{T_k} = Q_{T_{k-1}}\cos\alpha_{k-1} e^{-(t_k - t_{k-1})/T_1} \quad (16)$$
$$= (Q_{T_{k-2}}\cos\alpha_{k-2} e^{-(t_{k-1} - t_{k-2})/T_1})\cos\alpha_{k-1} e^{-(t_k - t_{k-1})/T_1}$$
$$= \ldots$$
$$= M_{ss} TAG(x, y)e^{-t_k/T_1} \prod_{j=0}^{k-1} \cos\alpha_j$$

$$Q_{R_k} = (Q_{R_{k-1}}\cos\alpha_{k-1} - M_0)e^{-(t_k - t_{k-1})/T_1} + M_0$$

where $Q_{Tk}$ is the tagging component, while $Q_{Rk}$ is the relaxed term. After the $k_{th}$ RF imaging pulse of flip angle $\alpha_k$, the longitudinal magnetization is rotated to the transverse plane which contributes to the $k_{th}$ image.

$$I_k = M_z(t_k)\sin\alpha_k e^{-TE/T^*2} = (Q_{T_k} + Q_{R_k})\sin\alpha_k e^{-TE/T^*2} \quad (17)$$

Figure 9:
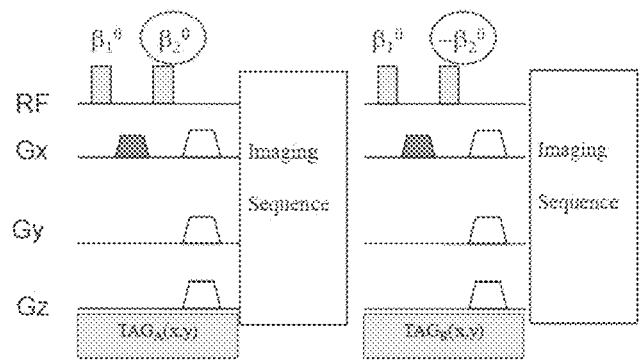
FIG. 9 is a timing diagram of a 1-1 Complimentary Spatial Modulation of Magnetization CSPAMM sequence.

FIG. 9 is a timing diagram of a 1-1 CSPAMM sequence. (a) Measurement with positive tagging pattern TAGA(x, y) (b) Measurement with negative tagging pattern TAGB(x, y). The basic idea of CSPAMM is to eliminate the relaxation term $Q_{Rk}$ while only keeping the tagging information term $Q_{Tk}$ by acquiring two images $A_k$ and $B_k$ using the same parameters except for their respective tagging patterns $TAG_A(x,y)$ and $TAG_B(x,y)$. The subtraction of both $k_{th}$ images leads to $$A_k - B_k = \quad (18)$$
$$M_{ss}[TAG_A(x, y) - TAG_B(x, y)]e^{-t_k/T_1}\left(\prod_{j=0}^{k-1}\cos\alpha_j\right)\sin\alpha_k e^{-TE/T_2^*}$$

Figure 10A:
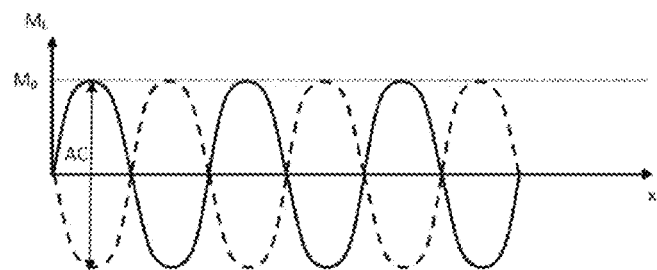
FIG. 10(a) is timing diagram showing magnetization in an initial state immediately after tagging pulse sequence.
Figure 10B:
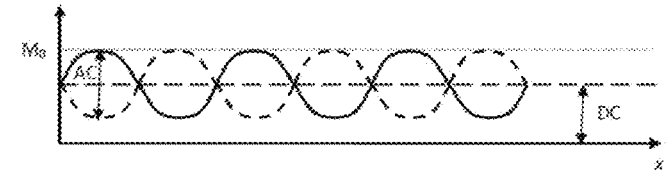
FIG. 10(b) is a timing diagram showing the magnetization after a certain time period after longitudinal relaxation.
Figure 10C:
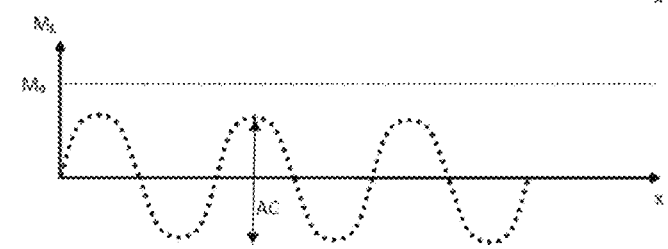
FIG. 10(c) is a timing diagram showing a CSPAMM tagging pattern from the subtraction of the negative pattern from the positive pattern in FIG. 10(b).

FIG. 10 shows a visualization of magnetization subtraction in CSPAMM. The positive sinusoidal SPAMM tagging pattern is shown in solid lines and the negative sinusoidal SPAMM tagging pattern is shown in dashed line. The subtracted CSPAMM pattern is shown in dotted line. (a) Shows the magnetization in the initial state immediately after tagging pulse sequence. With time, longitudinal relaxation occurs. (b) Shows the magnetization after a certain time period. (c) Shows the CSPAMM tagging pattern from the subtraction of the negative pattern from the positive pattern in (b).

Figures 11A, 11B, 11C:
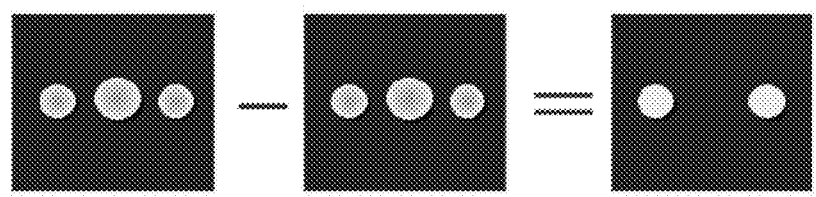
FIG. 11(a) is a visualization diagram of k-space for an image modulated by a cosine in the horizontal direction for one SPAMM with a positive tagging pattern.
FIG. 11(b) is a visualization diagram of k-space for the image modulated by the cosine in the horizontal direction for the other SPAMM with a negative tagging pattern.
FIG. 11(c) is the k-space for CSPAMM using the SPAMM of FIG. 11(a) and FIG. 11(b).
Figures 12A, 12B, 12C:
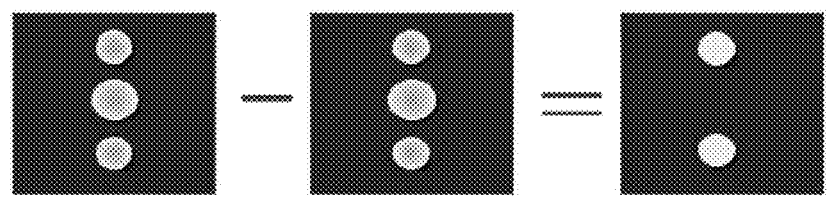
FIG. 12(a) is a visualization diagram of k-space for an image modulated by a cosine in the vertical direction for one SPAMM with a positive tagging pattern.
FIG. 12(b) is a visualization diagram of k-space for the image modulated by the cosine in the vertical direction for the other SPAMM with a negative tagging pattern.
FIG. 12(c) is the k-space for CSPAMM using the SPAMM of FIG. 12(a) and FIG. 12(b).

FIG. 11 shows a visualization of k-space for an image modulated by a cosine tagging function in the horizontal direction. FIG. 12 shows a visualization of k-space for an image modulated by a cosine tagging function in the vertical direction. In both figures, (a) shows the k-space for the SPAMM with positive tagging pattern, (b) shows the k-space for the other SPAMM with negative tagging pattern, and (c) is the k-space for CSPAMM which is the subtraction of (b) from (a).

5. Local Sine Wave Modeling as a Cardiac Deformation Analysis Technique from Tagged MRI Data In recent times, MRI tagging has seen increased applications and is becoming the gold standard for quantifying regional cardiac function. Local parameters such as twist, strain, and strain rate can be derived from tagged MRI data.

Local sine wave modeling (SinMod) is a frequency-based method to analyze the heart displacement and deformation from tagged MRI sequences using phase information [10]. SinMod detects both local spatial phase shift and local spatial frequency from band-pass filtered images. The speed of SinMod method is as fast as Harmonic Phase Analysis (HARP), another frequency-based method, but SinMod method has advantages in accuracy, noise reduction, and lack of artifacts [10]. In SinMod, the intensity distribution around each pixel (p, q) is modeled as a cosine wave front.

$$I_1(p, q) = A_1\cos\left(\omega_p\left(p + \frac{u}{2}\right) + \varphi\right) + n_1(p, q) \quad (19)$$

$$I_2(p, q) = A_2\cos\left(\omega_p\left(p - \frac{u}{2}\right) + \varphi\right) + n_2(p, q)$$

where $\omega_p$ and $\varphi$ are the spatial frequency and phase of the wave, respectively. $A_1$ and $A_2$ are wave magnitudes for the first image $I_1$ and the second image $i_2$, while $N_1$ and $n_2$ are additive noise. u is the displacement between these two images at position (p, q) along the p direction.

Figure 13:
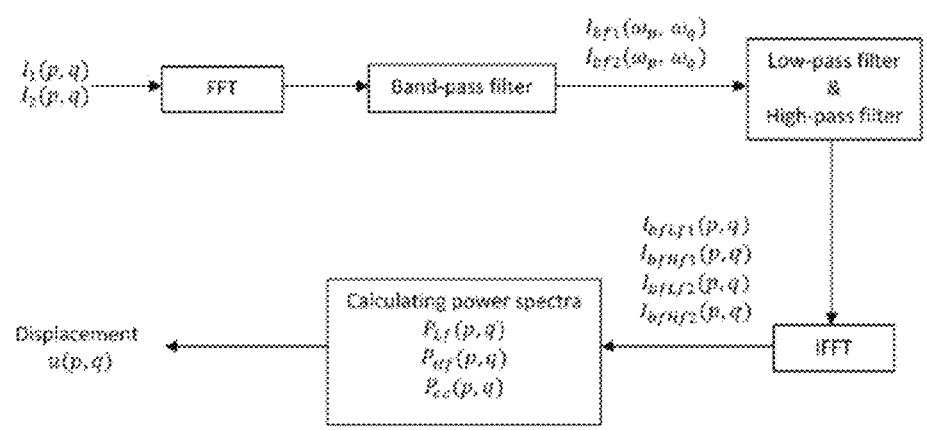
FIG. 13 is a flow chart for the local sine wave modeling (SinMod) method.
Figure 14C:
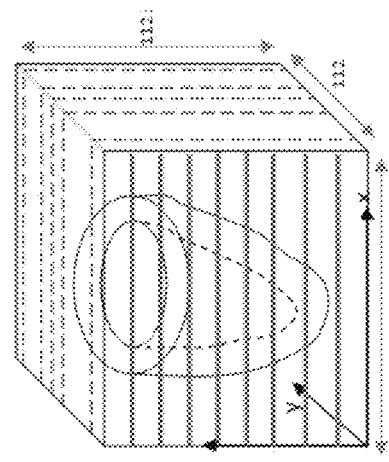
FIG. 14(c) is a schematic drawing of a 3D CSPAMM tagging data acquisition of a second Long Axis (LA2) stack for one cardiac phase.
Figure 14F:
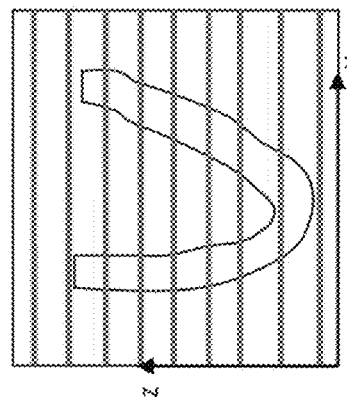
FIG. 14(f) is a 2-D slice from the stack of FIG. 14(c).
Figure 14B:
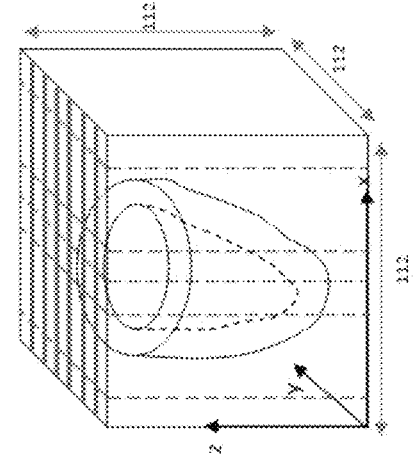
FIG. 14(b) is a schematic drawing of a 3D CSPAMM tagging data acquisition of a first Long Axis (LA1) stack for one cardiac phase.
Figure 14E:
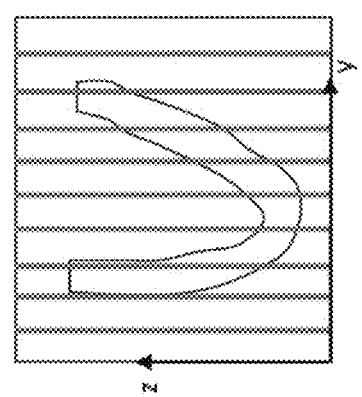
FIG. 14(e) is a 2-D slice from the stack of FIG. 14(b).
Figure 14A:
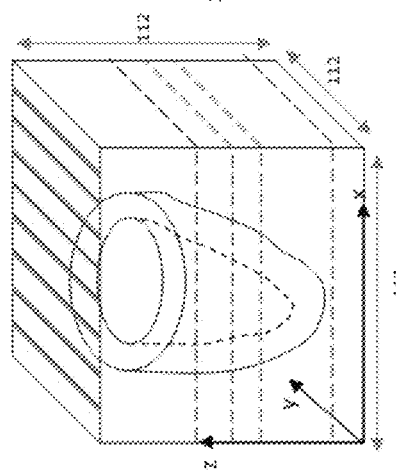
FIG. 14(a) is a schematic drawing of a 3D CSPAMM tagging data acquisition of a Short Axis (SA) stack for one cardiac phase.
Figure 14D:
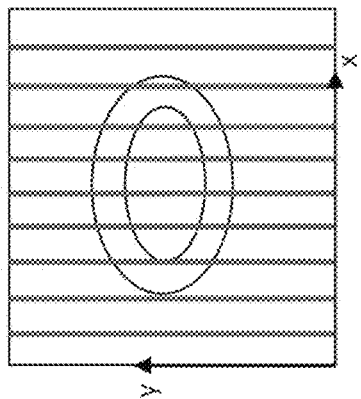
FIG. 14(d) is a 2-D slice from the stack of FIG. 14(a).

FIG. 13 is a flow chart of a SinMod method. The principle behind SinMod tracking is that both phase and frequency for each pixel are determined directly from the frequency analysis and the displacement is calculated from the quotient of phase difference and local frequency. After obtaining the Fourier Transform of the input images $I_1(p, q)$ and $I_2(p, q)$ (temporal frames at time t and time t+1), the same band-pass filter is applied to both to isolate corresponding spectral peaks and produce a pair of complex images in the Fourier domain (since the Fourier Transform will be complex to begin with). Let us refer to the two complex images in Fourier domain following band-pass filtering $I_{bf1}(\omega_p, \omega_q)$ and $I_{bf2}(\omega_p, \omega_q)$. Applying a low frequency band-pass filter and a high frequency one to both $I_{bf1}$ and $I_{bf2}$ followed by an inverse Fourier transform leads to four complex images $I_{bfLF1}(p, q)$, $I_{bfHf1}(p, q)$, $I_{bfLf2}(p, q)$, and $I_{bfHf2}(p, q)$. The reasoning behind application of a LPF and a HPF to $I_{bf1}$ and $I_{bf2}$ is to determine the local spatial frequency by power spectra. Then the displacement is the local quotient of phase difference and local frequency at that position. The power spectra and cross power spectrum are given by:

$$P_{Lf}(p,q) = |I_{bfLf1}|^2 + |I_{bfLf2}|^2$$

$$P_{Hf}(p,q) = |I_{bfHf1}|^2 + |I_{bfHf2}|^2$$

$$P_{cc}(p,q) = I_{bfLf1}\bar{I}_{bfLf2} + I_{bfHf1}\bar{I}_{bfHf2} \quad (20)$$

where $\bar{I}$ is the complex conjugation of I.

The local frequency $\omega_p$ and local displacement u can then be estimated from:

$$\omega_p(p, q) = \omega_c\sqrt{\frac{P_{Hf}}{P_{Lf}}} \quad (21)$$

$$u(p, q) = \frac{\arg(P_{cc})}{\omega_p}$$

where $\omega_c$ is the band-pass center-frequency.

6. Analysis of 3D CSPAMM Tagged MRI Data with 3D SinMod

Most of the current motion analysis techniques are applicable to 2D+t tagged MR image sequences. 2D motion analysis has its inherent disadvantages, since it can only capture in-plane expansions, contractions, and rotations of the myocardium. However, the heart deforms in 3D+t with complex twisting motion combined with longitudinal shortening and wall thickening. A 3D sine wave modeling (3D SinMod) method is described below which accurately recovers true 3D cardiac deformations from 3D CSPAMM MRI. An accelerated 3D complementary spatial modulation of magnetization (3D CSPAMM) tagging technique was used to acquire 3D MR data set for the whole-heart in 7 subjects [11]. The entire framework, from data acquisition to data analysis is in the 3D domain, which overcomes the through-plane motion of the LV myocardium.

The data were acquired using the 3D CSPAMM tagging sequence [11] described above. In three breath-holds each with 18 heartbeats, the acquisition was applied three times (once for each breath-hold) where in each case, the tagging gradient was rotated in such a way to acquire 3D+t data with orthogonal tags. Note that in each acquisition, two 3D SPAMM tagging volumes are acquired and subtracted from each other, which gives CSPAMM data. Typical imaging parameters were: FOV=108×108×108 mm$^3$, matrix size=28 (Frequency Encoding)×14 (Phase Encoding)×16 (16 in slice select direction, but only 14 out of 16 were used in reconstruction). In the spatial domain, the image matrix size was 112×112, slice thickness=8 mm, and tag spacing was 7 mm. Each data set consisted of 20-24 frames per cardiac cycle.

FIG. 14 illustrates the tagging directions and image slice orientations for 3D CSPAMM acquisition. Solid lines represent tagging planes, while dashed lines represent imaging planes. For each cardiac phase, there are three 3D data sets. (a) is a short axis (SA) stack, (b) is a first long axis (LA1) stack, and (c) is a second long axis (LA2) stack. (d) is a 2D slice from (a). (e) is a 2D slice from (b). (f) is a 2D slice from (c).

Figure 15:
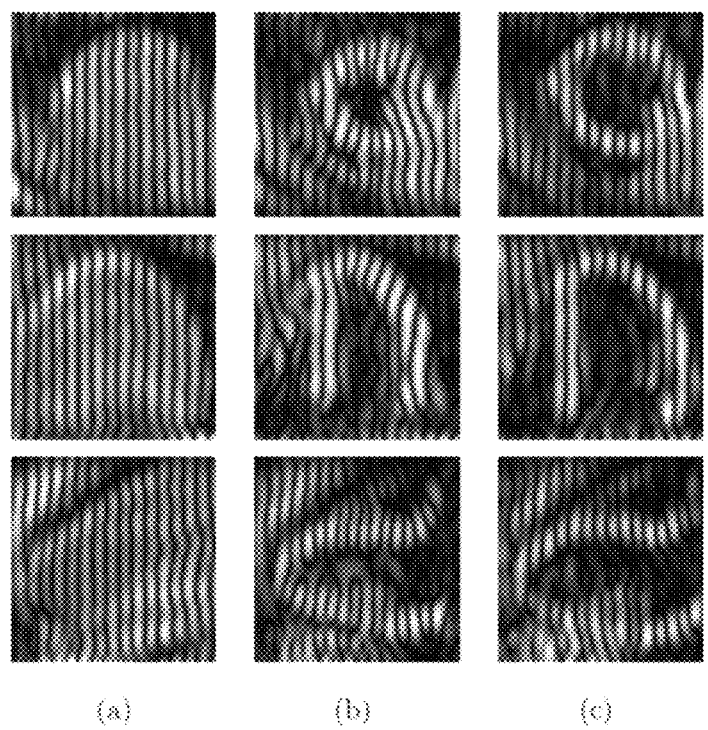
FIG. 15 shows exemplary mid-ventricular slices for three data sets with orthogonal tagging directions from 3D CSPAMM sequence. The first row is from the SA view, and the second and third rows are from two LA views. Column (a) is at beginning systole. Column (b) is at end-systole. Column (c) is at end-diastole.

FIG. 15 shows images at select time frames at end-diastole and end-systole for a single mid-ventricular slice at each orthogonally line tagged 3D CSPAMM data set. The first row is for SA view, and the second and third rows are for two LA views. (a) is at the beginning of systole. (b) is at end-systole. (c) is at end-diastole. At end-systole (column (b)), the tag lines contract and rotate (row 1 and row 2) and exhibit longitudinal shortening (row 3).

Figure 16:
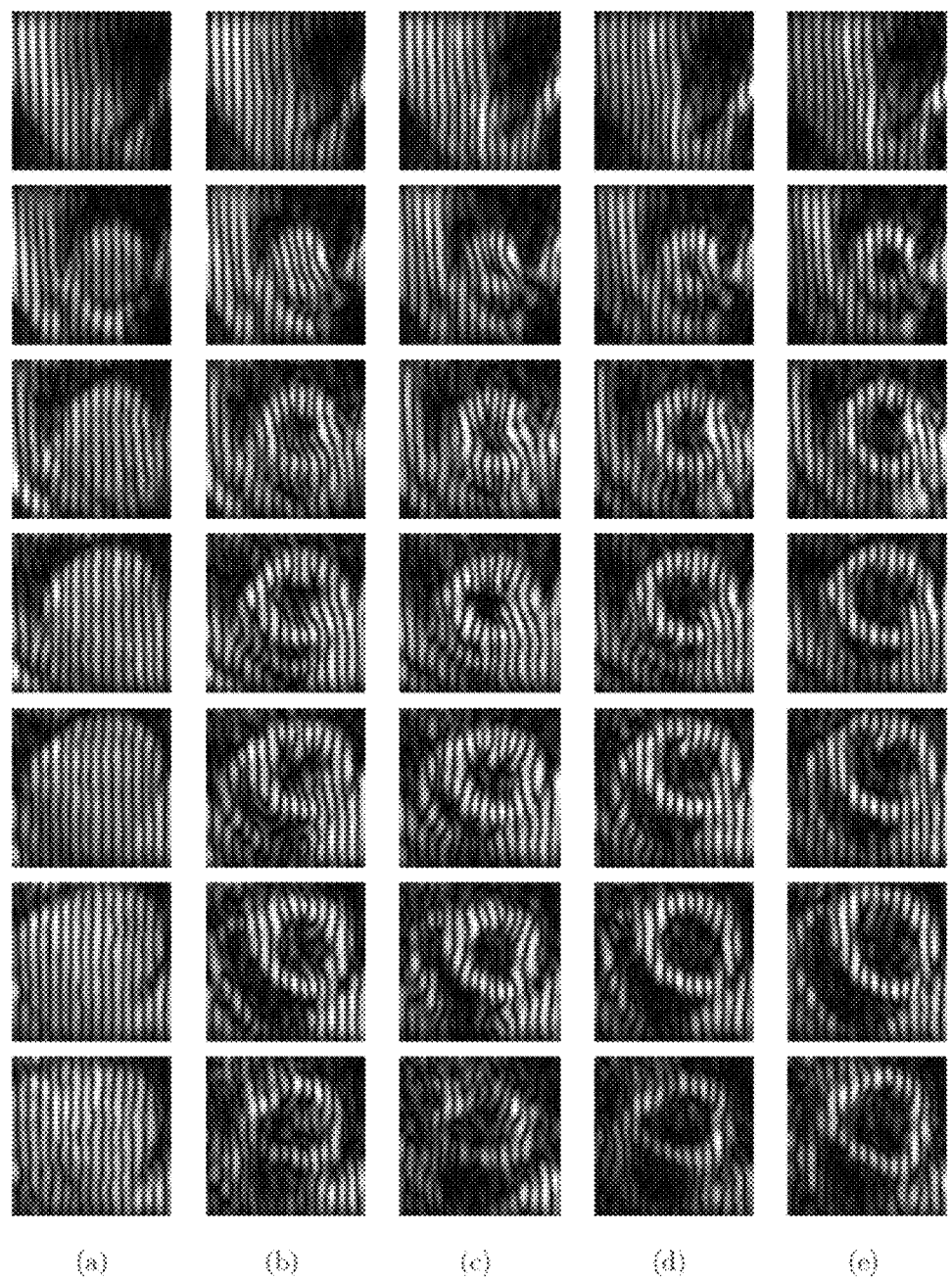
FIG. 16 shows exemplary axis slices from apex to base acquired with the 3D CSPAMM sequence. Column (a) is at the first phase (at end-diastole). Column (b) is at the 6th phase (at mid-systole). Column (c) is at the 11th phase (at end-systole). Column (d) is at the 16th phase (at mid-diastole). Column (e) is at the 20th phase (at end-diastole). Row 1 is of slice 1 (apex). Row 2 is of slice 3. Row 3 is of slice 5. Row 4 is of slice 7. Row 5 is of slice 9. Row 6 is of slice 11. Row 7 is of slice 13 (basal).

FIG. 16 shows select short axis slices from apex to base acquired with the 3D CSPAMM sequence. (a) is the first phase (at end-diastole). (b) is the 6th phase (at mid-systole). (c) is the 11th phase (at end-systole). (d) is the 16th phase (at mid-diastole). (e) the 20th phase (at end-diastole). Row 1 is slice 1 (apex). Row 2 is slice 3. Row 3 is slice 5. Row 4 is slice 7. Row 5 is slice 9. Row 6 is slice 11. Row 7 is slice 13 (basal). The left ventricular contraction and rotation can be observed during systole.

As with 2D SinMod [10] that was described above, the neighborhood around each voxel in the 3D tagged volume is modeled as a moving sine wave front with local frequency and amplitude.

$$V_1(x, y, z) = A_1\cos\left(\omega_x\left(x + \frac{u}{2}\right) + \varphi\right) + n_1(x, y, z) \quad (22)$$

$$V_2(x, y, z) = A_2\cos\left(\omega_x\left(x - \frac{u}{2}\right) + \varphi\right) + n_2(x, y, z)$$

where $\omega_x$ and $\varphi$ are the spatial frequency and phase of the wave, respectively. $A_1$ and $A_2$ are wave magnitudes for a 3D volume $V_1$ and a short time later, a 3D volume $V_2$, while $n_1$ and $n_2$ are additive noise. u is the displacement between these two volumes at position (x, y, z) along the x direction. The displacements v and w in the y and z directions have expressions similar to Equation (22). The principle behind 3D SinMod tracking is that both phase and frequency of the moving wave front for each voxel can be determined directly from the frequency analysis and the 3D displacement can be calculated from the quotient of phase difference and local frequency.

Figure 17:
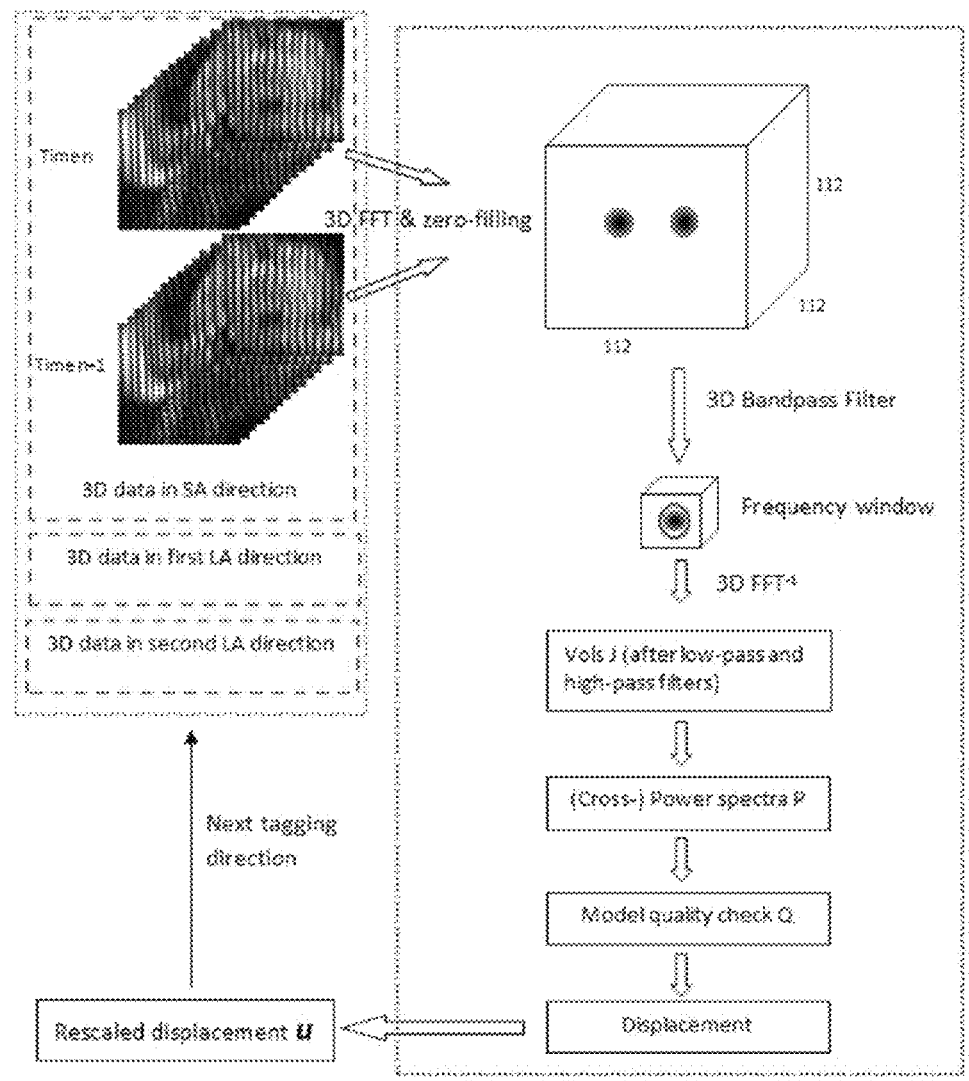
FIG. 17 is a flow chart of the 3D SinMod algorithm to obtain 3D displacements.

FIG. 17 is a flow chart for the 3D SinMod method. A first step is Fourier transforming two stacks of 3D image volumes at times n and n+1 (obtaining the Fourier Transform of the input volumes ($V_1(x, y, z)$ and $V_2(x, y, z)$ (temporal frames at time n and time n+1)). Next, a 3D band-pass filter is applied to isolate corresponding spectral peaks (i.e., to separate one off-center spectral peak) and to produce a pair of complex volumes in the Fourier domain ($V_{bf1}(\omega_x, \omega_y, \omega_z)$ and $V_{bf2}(\omega_x, \omega_y, \omega_z)$). Applying a low frequency band-pass filter (LPF) and a high frequency band-pass filter (HPF) to both $V_{bf1}$ and $V_{bf2}$ followed by an inverse Fourier transform leads to four complex volumes $V_{bfLf1}(x, y, z)$, $V_{bfHf1}(x, y, z)$, $V_{bfLf2}(x, y, z)$, and $V_{bfHf2}(x, y, z)$ ((i.e., a window around the band-passed frequencies is inverse Fourier transformed to obtain down-sampled complex volume J). The reasoning behind application of a LPF and a HPF to $V_{bf1}$ and $V_{bf2}$ is to determine the local spatial frequency by power spectra. Then the displacement is the local quotient of phase difference and local frequency at that position. The power spectra and cross power spectrum are given by:

$$P_{Lf}(x,y,z) = |V_{bfLf1}|^2 + |V_{bfLf2}|^2$$

$$P_{Hf}(x,y,z) = |V_{bfHf1}|^2 + |V_{bfHf2}|^2$$

$$P_{cc}(x,y,z) = V_{bfLf1}\overline{V}_{bfLf2} + V_{bfHf1}\overline{V}_{bfHf2} \quad (23)$$

where $\overline{V}$ is the complex conjugate of V.

The local frequency $\omega x$ and local displacement u can then be estimated from:

$$\omega_x(x, y, z) = \omega_c \sqrt{\frac{P_{Hf}}{P_{Lf}}} \quad (21)$$

$$u(x, y, z) = \frac{\arg(P_{cc})}{\omega_p}$$

where $\omega_c$ is the band-pass center-frequency.

This map is then up-sampled to the initial size of the volume. Repeating the same steps for the two LA directions recovers the full 3D displacements.

To isolate the spectral peaks, a Butterworth filter was applied in k-space. As shown in Equation (25), the Butterworth filter is a discrete approximation to the Gaussian. In the exemplary embodiment, a $5^{th}$ order Butterworth band-pass filter was used with the cutoff frequency being half of the center frequency.

$$H = \frac{1}{1.0 + ((\omega - \omega_c)/\omega_{cutoff})^{2n}} \quad (25)$$

where $\omega_c$ is the off-center frequency for tagged images, $\omega_{cutoff}$ is the cutoff frequency, and n is the order for Butterworth filter (in the example, n=5).

Figure 18:
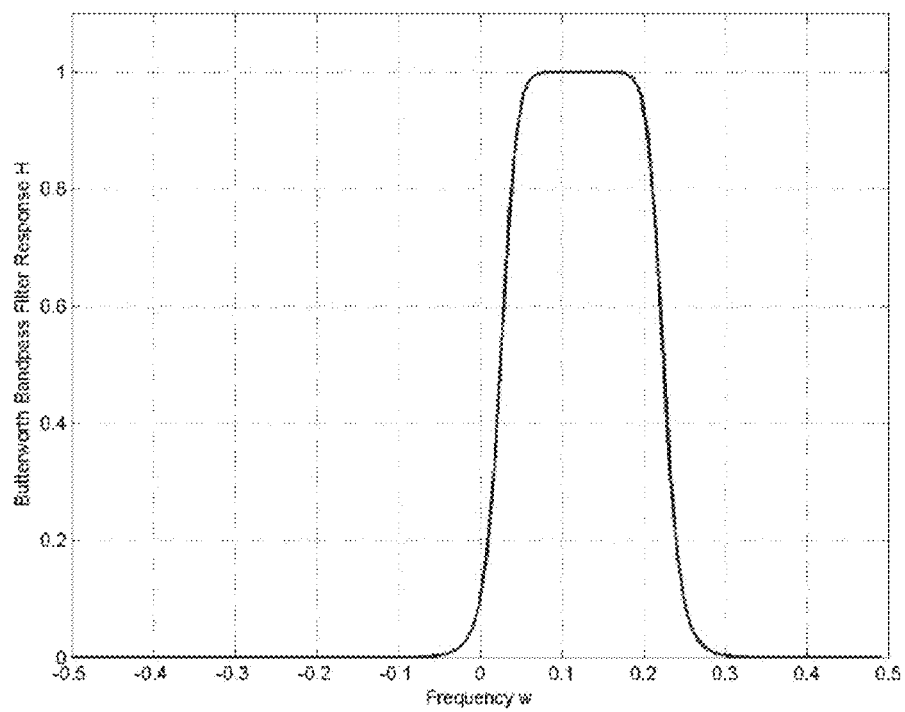
FIG. 18 is a graph showing the response of an exemplary Butterworth band-pass filter transfer function in 1D.

FIG. 18 shows an exemplary Butterworth band-pass filter transfer function, where $\omega_{cutoff}=0.1$, $\omega_c=0.125$, and n=5.

7. Computational Time

In an exemplary embodiment, software code for performing the steps of the methods described above may be programmed in a high-level technical computing language such as MATLAB®, by The MathWorks, Inc., of Nantic, Mass., on a personal computer (e.g., with a microprocessor such as an Core i5 2.6 GHz CPU by Intel Corporation, of Santa Clara, Calif., with 4 GB main memory, running an operating system such as a 64-bit Windows® 7 operating system, by Microsoft Corporation, of Redmond, Wash.). Using such an exemplary system, the overall processing time for 3D SinMod processing is about 5-7 minutes for one 3D+t data set. The average CPU time for calculating the 3D motion fields between a pair of 3D volumes for each of the data sets was 17.37 seconds. Table 1 shows the average computational time for on 7 in-vivo data sets as well as the average time for calculating 3D displacements between a pair of 3D volumes. After zero-fill, each data set consisted of 20-24 volumetric frames each with 112×112 voxels. It would be possible to further reduce the computational time by using a faster computer/workstation with implementation in C++.

TABLE 1

| Data Set Number | Average Time (sec/min) to process all 4-D data | Average Time/phase (sec) |
| --- | --- | --- |
| 1 | 358.16/5.97 | 17.91 |
| 2 | 345.71/5.76 | 17.29 |
| 3 | 414.24/6.90 | 17.26 |
| 4 | 409.96/6.83 | 17.82 |
| 5 | 355.71/5.93 | 16.94 |
| 6 | 368.27/6.14 | 17.54 |
| 7 | 353.82/5.90 | 16.85 |

8. Validations a. Simulation

In order to assess the accuracy of the tracking results, the inventors simulated 3D+t CSPAMM data with the same number of slices and spatial resolution as that of the real data. Three image sequences each containing 2 volumetric frames but with different displacement fields were generated.

Figures 19A, 19B, 19C:
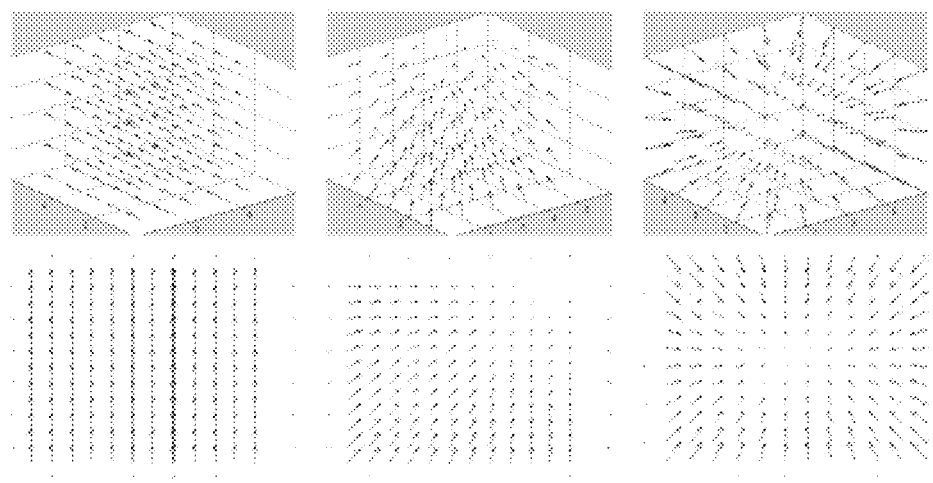
FIG. 19(*a*) is an exemplary displacement field in the y direction in a simulated sequence, where the first row displays a 3D visualization and the second row is the 2D projection of the first row.

FIGS. 19(a)-(c) show displacement fields in a simulated sequence. FIG. 19(a) shows a translation displacement field in the y direction. FIG. 19(b) shows non-homogeneous translations in the x, y, z directions. FIG. 19 (c) shows a contraction displacement field. The first row displays 3D visualization, while the second row is the 2D projection of the first row.

FIG. 19(a) is the first sequence and contains tags with 2 pixel uniform translation in the y direction alone. FIG. 19(b) is the second sequence and contains tags with 2, 3, and 2 pixel gradual translations in x, y, and z directions. Non-rigid motion, such as contraction (FIG. 19(c)) and expansion were also applied to test the algorithm. The simulated displacement fields for the translating sequence and the contracting sequence are illustrated in FIGS. 19(a)-(c). Expansion can be considered as the inverse of the contraction motion.

The 3D SinMod method was applied to the artificially deformed data sets, permitting comparison between the algorithm estimated deformations in the presence of additional Gaussian noise and the known true deformations. Tracking error was calculated for every material point within the 3D volume and then averaged. The performance of the proposed 3D SinMod method, reported here as the average error in pixels, is shown in Table 2, below.

TABLE 2

| | Translation Y | Translation X, Y, Z | Contraction | Expansion |
| --- | --- | --- | --- | --- |
| AveError | 0.0043 | 0.0329 | 0.0067 | 0.0079 | b. Comparison to 3D HARP

Seven real 3D+t CSPAMM data sets of healthy human subjects were used to validate the 3D SinMod method. For each data set, there were about 20×3 image volumes, with 14 slices in each volume. Therefore, in total, there were about 20×3×14=840 images in each subject data set.

Figure 20:
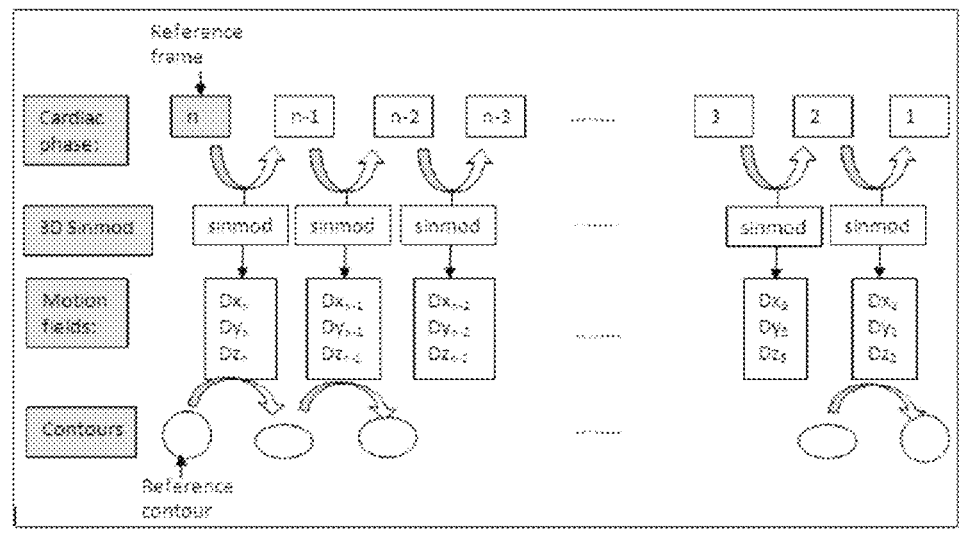
FIG. 20 is a flow diagram for comparison of mid-wall contour deformation using motion field from 3D SinMod algorithm with 3D HARP.

For each image volume at reference state, ten mid-wall contours, constructed from multiple landmark points with about 5° separation were defined on different short-axis slices. The reference state was chosen to be the last cardiac phase which had good myocardial-blood pool contrast permitting good contour definition. The 3D SinMod method was applied to every consecutive pair of cardiac phases and the displacement fields were reconstructed. In order to validate the results, the mid-wall contours at the reference state were deformed to the following phases according to the motion fields obtained from 3D SinMod and results were compared with the deformed contours obtained from 3D HARP [11]. FIG. 20 shows the workflow for comparison of mid-wall contour deformation using motion field from the 3D SinMod method with the 3D HARP method.

Figure 21:
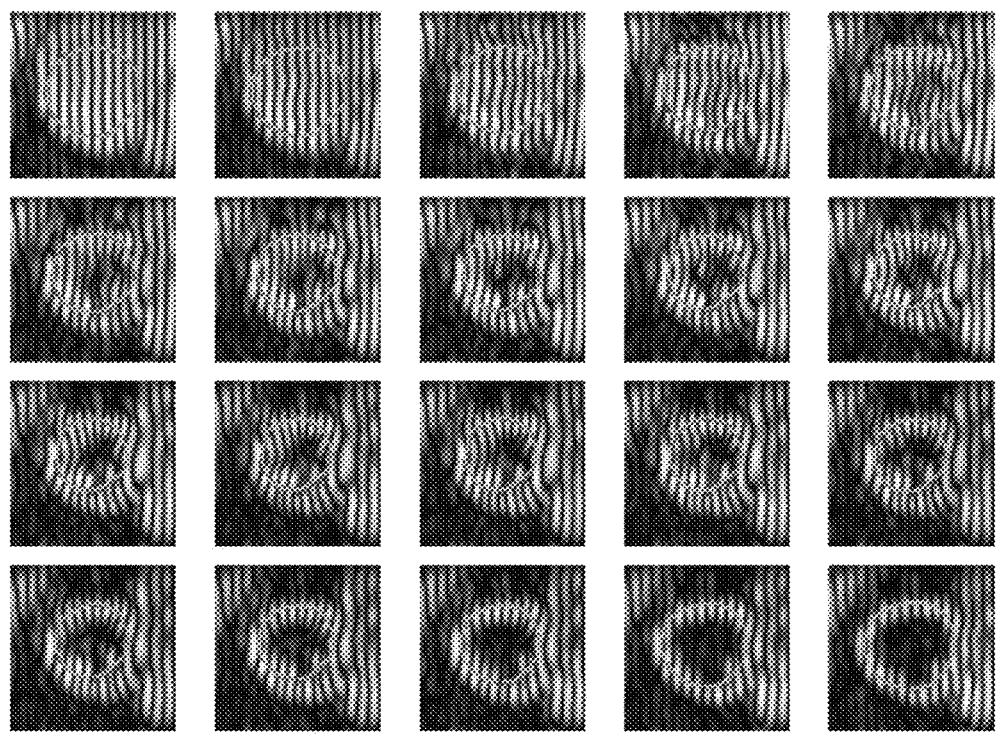
FIG. 21 shows mid-wall contours at a mid-ventricular slice for all phases. Traversing from top-left to the bottom-right are phases 1 to 20. The red contours are deformed with motion field from 3D SinMod. The green contours are deformed with motion field from 3D HARP.

FIG. 21 shows mid-wall contours at a mid-ventricular slice for all phases. Traversing from top-left to the bottom-right are phases 1 to 20. The red contours are deformed with motion field from 3D SinMod. The green contours are deformed with motion field from 3D HARP. There is a good degree of correspondence between the two. Table 3 shows the average error between deformed mid-wall contours from 3D SinMod and 3D HARP for slices 2 to 10 over all cardiac phases. The reported errors are in pixels.

TABLE 3

|  | data 1 | data 2 | data 3 | data 4 | data 5 | data 6 | data 7 |
| --- | --- | --- | --- | --- | --- | --- | --- |
| slice 2 | 0.90 | 1.16 | 0.86 | 0.86 | 0.70 | 0.74 | 0.82 |
| slice 3 | 0.79 | 1.36 | 0.68 | 0.99 | 0.59 | 0.87 | 0.81 |
| slice 4 | 0.72 | 1.05 | 0.74 | 0.84 | 0.49 | 0.86 | 0.96 |
| slice 5 | 0.73 | 0.88 | 0.75 | 0.95 | 0.54 | 0.83 | 0.95 |
| slice 6 | 0.72 | 0.92 | 0.67 | 0.78 | 0.67 | 0.87 | 1.05 |
| slice 7 | 0.80 | 1.00 | 0.68 | 0.82 | 0.84 | 0.95 | 1.03 |
| slice 8 | 0.96 | 0.94 | 0.93 | 0.90 | 1.12 | 0.94 | 1.01 |
| slice 9 | 1.28 | 0.97 | 1.24 | 1.22 | 1.36 | 0.94 | 1.37 |
| slice 10 | 1.40 | 1.16 | 1.60 | 1.36 | 1.64 | 1.07 | 1.98 |

Figure 22A:
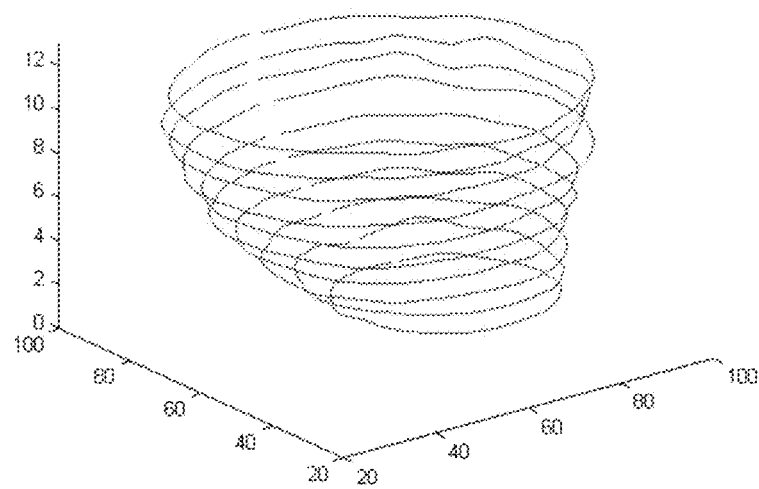
FIG. 22(*a*) is a 3-D graph of mid-wall contours tracked by 3D SinMod at the beginning of systole.
Figure 22B:
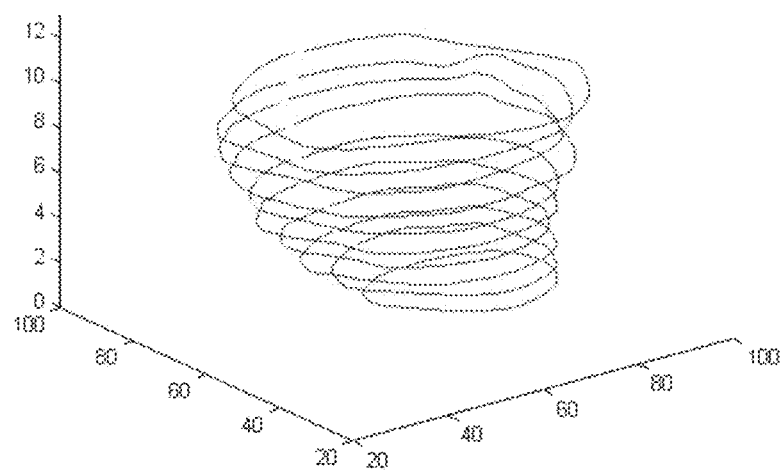
Figure 22C:
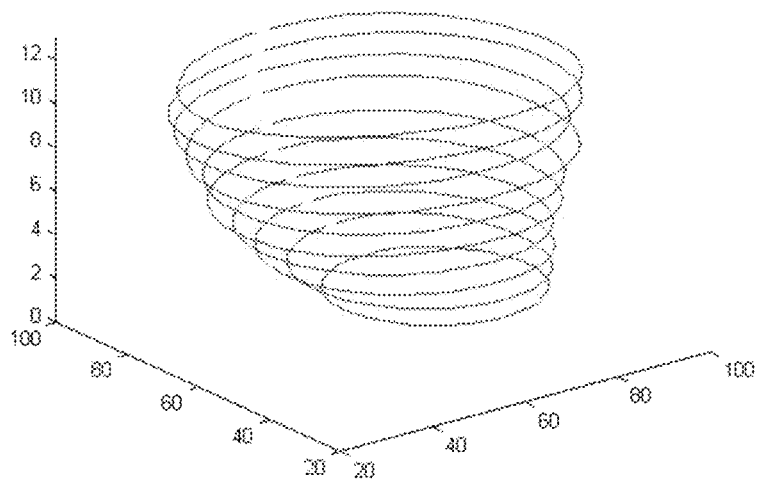

FIGS. 22(a)-(c) show 3D mid-wall contours tracked by 3D SinMod. FIG. 22(a) is at the beginning of systole. FIG. 22(b) is at end-systole. FIG. 22(c) is at end-diastole. Comparing FIG. 22(a) at end-diastole and FIG. 22(b) at end-systole, longitudinal shortening from base to apex may easily be observed.

c. Comparison of Warped with Manually Delineated Tag Lines

All tag lines on 11 slices (from apex to base) and over 11 systolic phases in the same seven 3D CSPAMM tagged data sets were manually delineated. Subsequently, the manually delineated tag lines from each time were warped to time t+1 and the location of the warped tag lines were compared to location of manually delineated tag lines and an average error for all slices at each phase was computed.

Figure 23:
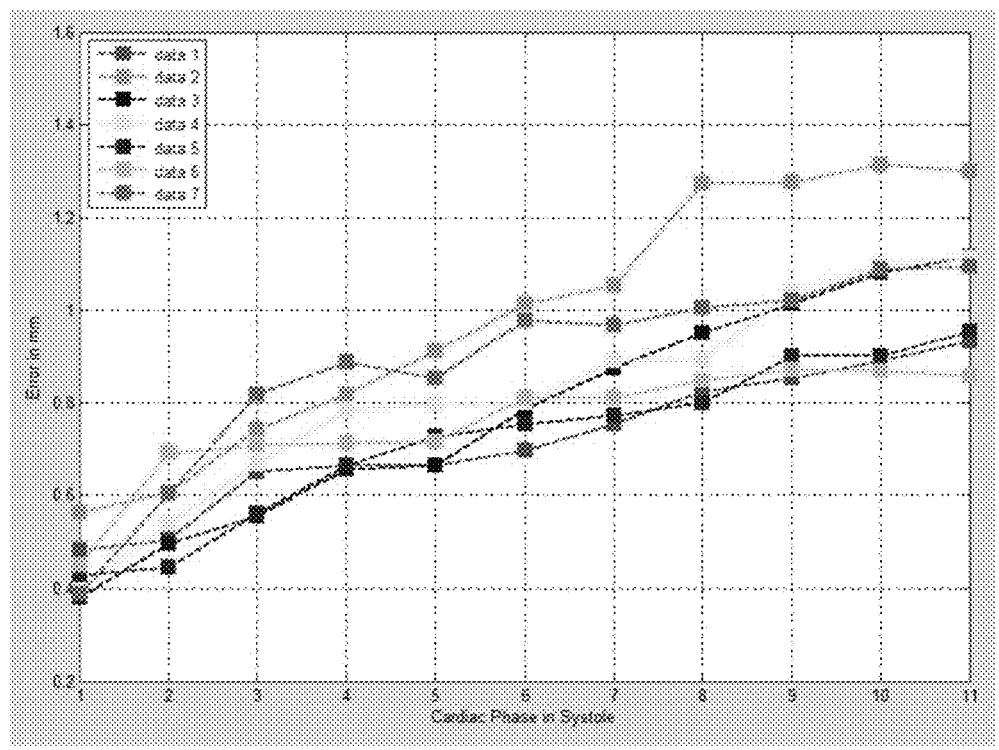
FIG. 23 is a graph of 3D SinMod's average error as a function of time for determining tag line displacements during systole for 7 in-vivo data sets.

FIG. 23 displays the average error as a function of time for each of the 7 data sets. 3D SinMod's average error as a function of time for determining tag line displacements during systole for 7 in-vivo data sets. Results for data sets 1, 2, 3, 4, 5, 6, and 7 are differentiated with red, green, black, yellow, blue, cyan, and magenta colors. Please note that the error for each time point was calculated from the error between tag line locations from time t warped to time t+1 and manually delineated tag lines on all image slices. As may be observed, all errors are in the sub-pixel range.

9. Results a. Visualization of Motion Fields

Figure 24:
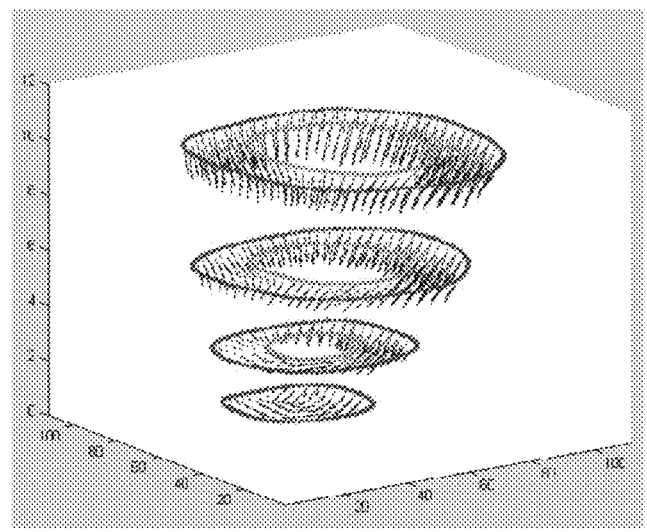
FIG. 24 is a 3-D graph of calculated 3-D motion fields at apex, apical, mid-cavity, and basal slices for data set 1.
Figure 25:
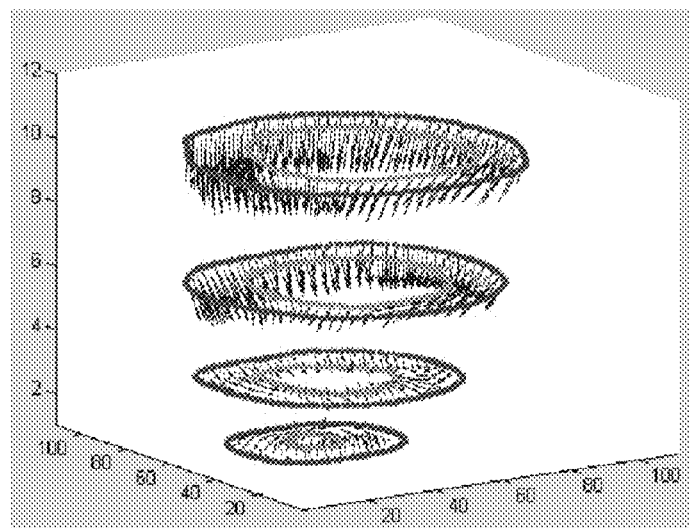
FIG. 25 is a 3-D graph of calculated 3-D motion fields at apex, apical, mid-cavity, and basal slices for data set 2.
Figure 26:
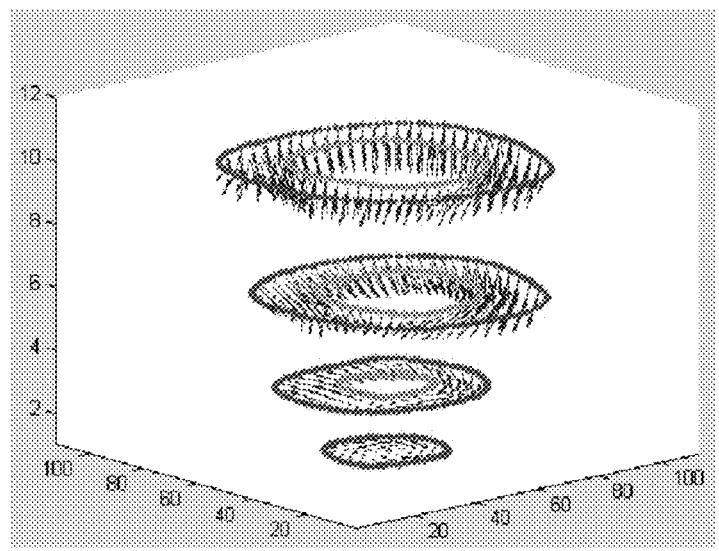
FIG. 26 is a 3-D graph of calculated 3-D motion fields at apex, apical, mid-cavity, and basal slices for data set 3.
Figure 27:
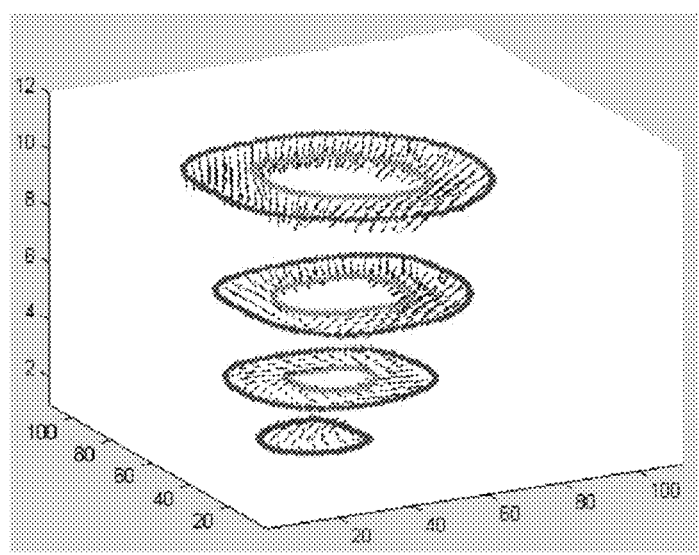
FIG. 27 is a 3-D graph of calculated 3-D motion fields at apex, apical, mid-cavity, and basal slices for data set 4.
Figure 28:
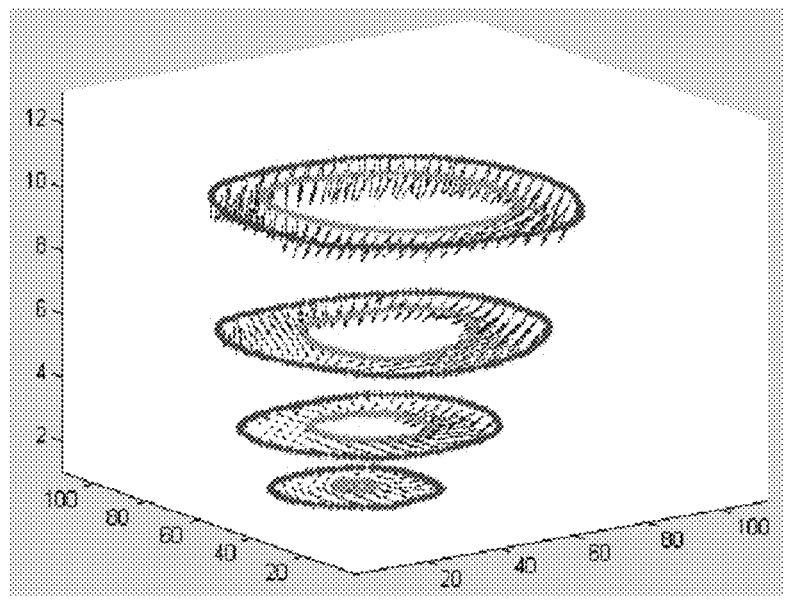
FIG. 28 is a 3-D graph of calculated 3-D motion fields at apex, apical, mid-cavity, and basal slices for data set 5.
Figure 29:
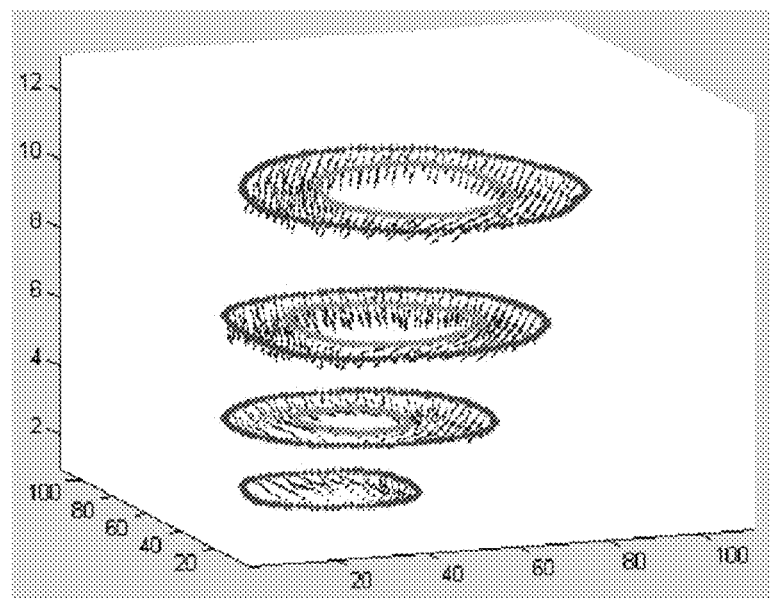
FIG. 29 is a 3-D graph of calculated 3-D motion fields at apex, apical, mid-cavity, and basal slices for data set 6.
Figure 30:
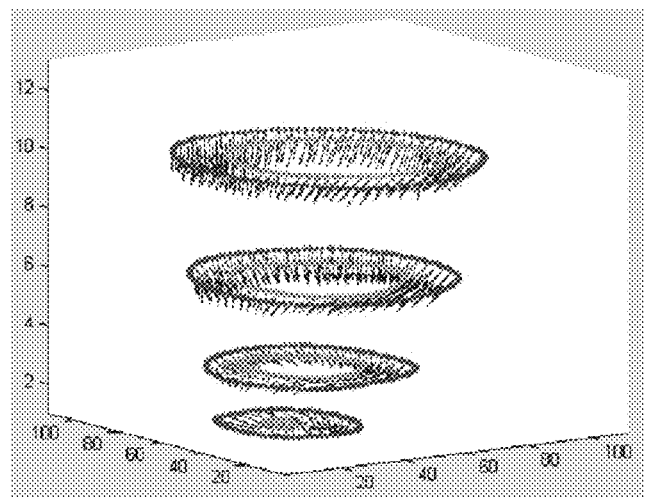
FIG. 30 is a 3-D graph of calculated 3-D motion fields at apex, apical, mid-cavity, and basal slices for data set 7.

Left ventricular endocardial and epicardial contours were traced manually at all phases for all 3D data sets. The calculated 3D motion fields at apex, apical, mid-cavity, and basal slices are shown in FIG. 24 to FIG. 30 for data set 1 to 7. FIG. 24 is the end systolic 3D motion field for slice 1, 3, 6, and 10 for data set 1. FIG. 25 is the end systolic 3D motion field for slice 1, 3, 6, and 10 for data set 2. FIG. 26 is the end systolic 3D motion field for slice 1, 3, 6, and 10 for data set 3. FIG. 27 is the end systolic 3D motion field for slice 1, 3, 6, and 10 for data set 4. FIG. 28 is the end systolic 3D motion field for slice 1, 3, 6, and 10 for data set 5. FIG. 29 is the end systolic 3D motion field for slice 1, 3, 6, and 10 for data set 6. FIG. 30 is the end systolic 3D motion field for slice 1, 3, 6, and 10 for data set 7.

Figure 31:
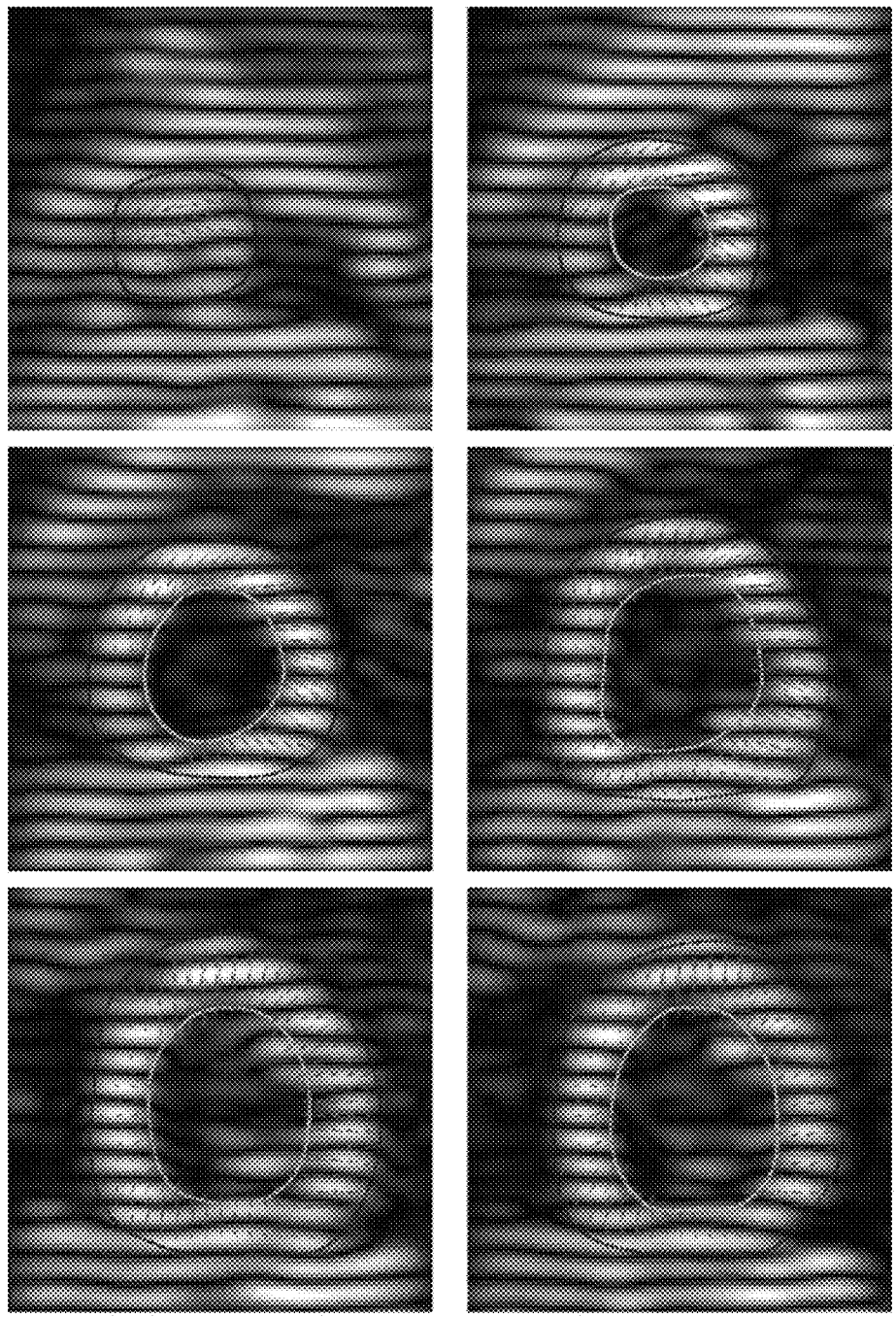
FIG. 31 is a projected 2-D end-systolic motion field on slices 1, 3, 5, 7, 9, 10 for data set 1 (row 1: apex, row 2: mid-ventricular, row 3: base).
Figure 32:
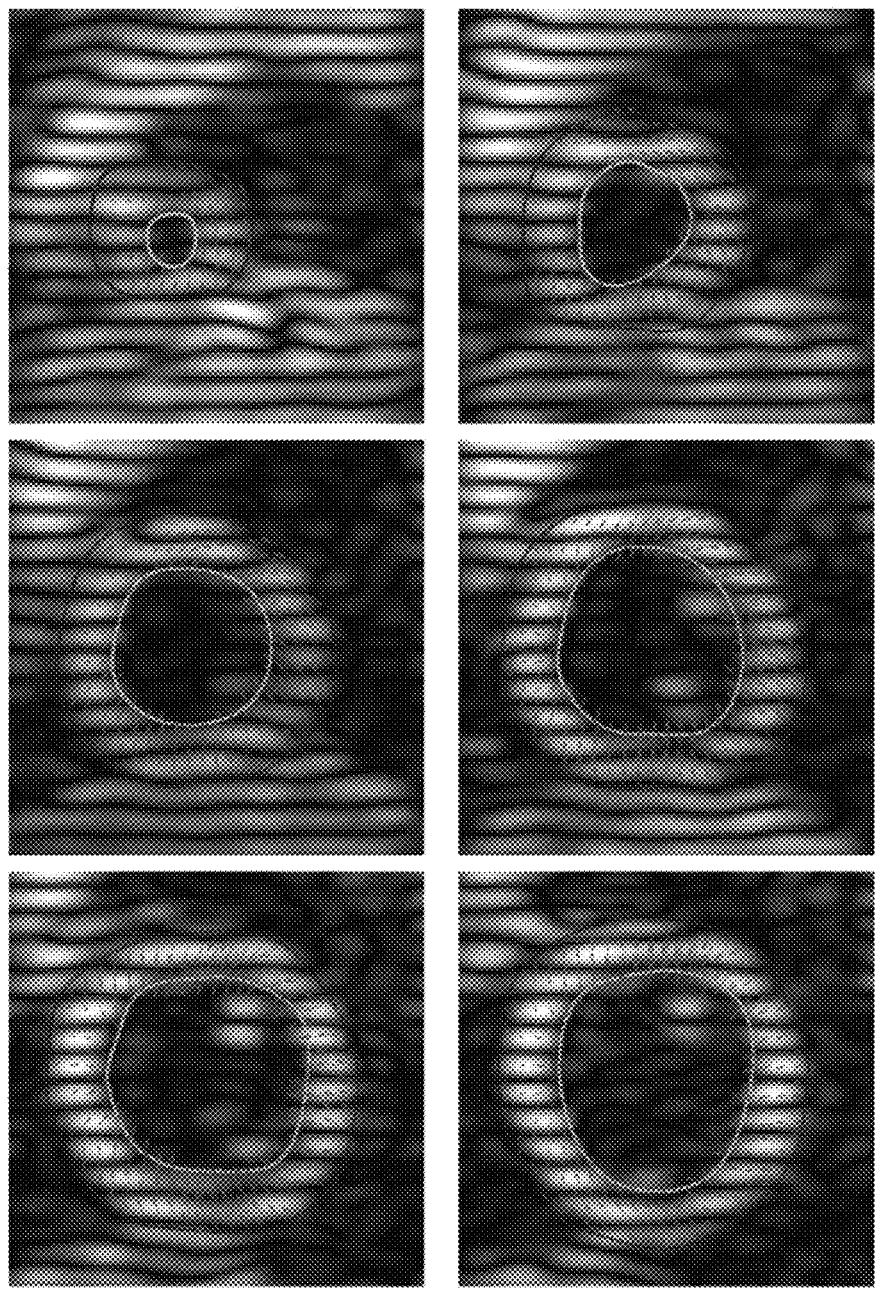
FIG. 32 is a projected 2-D end-systolic motion field on slices 1, 3, 5, 7, 9, 10 for data set 2 (row 1: apex, row 2: mid-ventricular, row 3: base).
Figure 33:
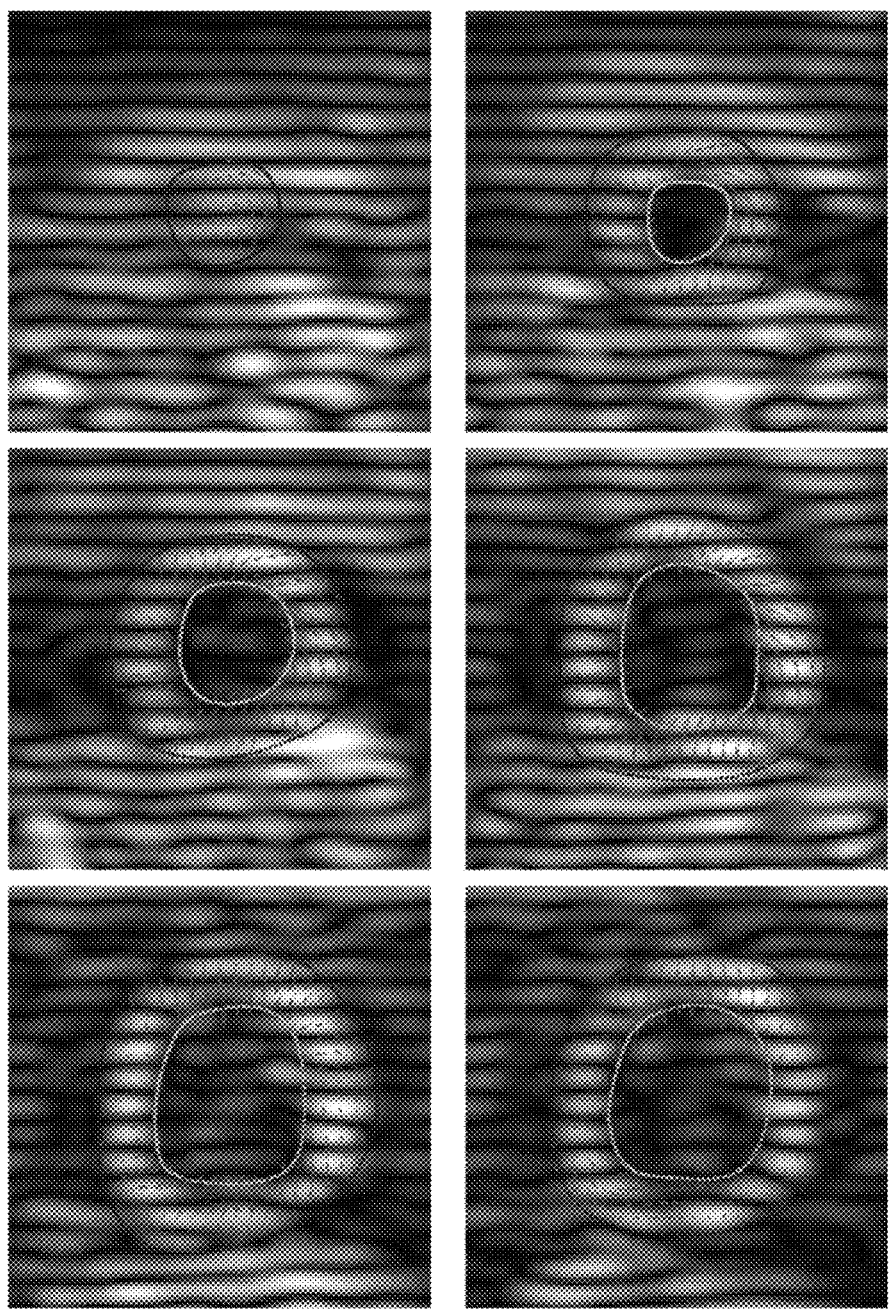
FIG. 33 is a projected 2-D end-systolic motion field on slices 1, 3, 5, 7, 9, 10 for data set 3 (row 1: apex, row 2: mid-ventricular, row 3: base).
Figure 34:
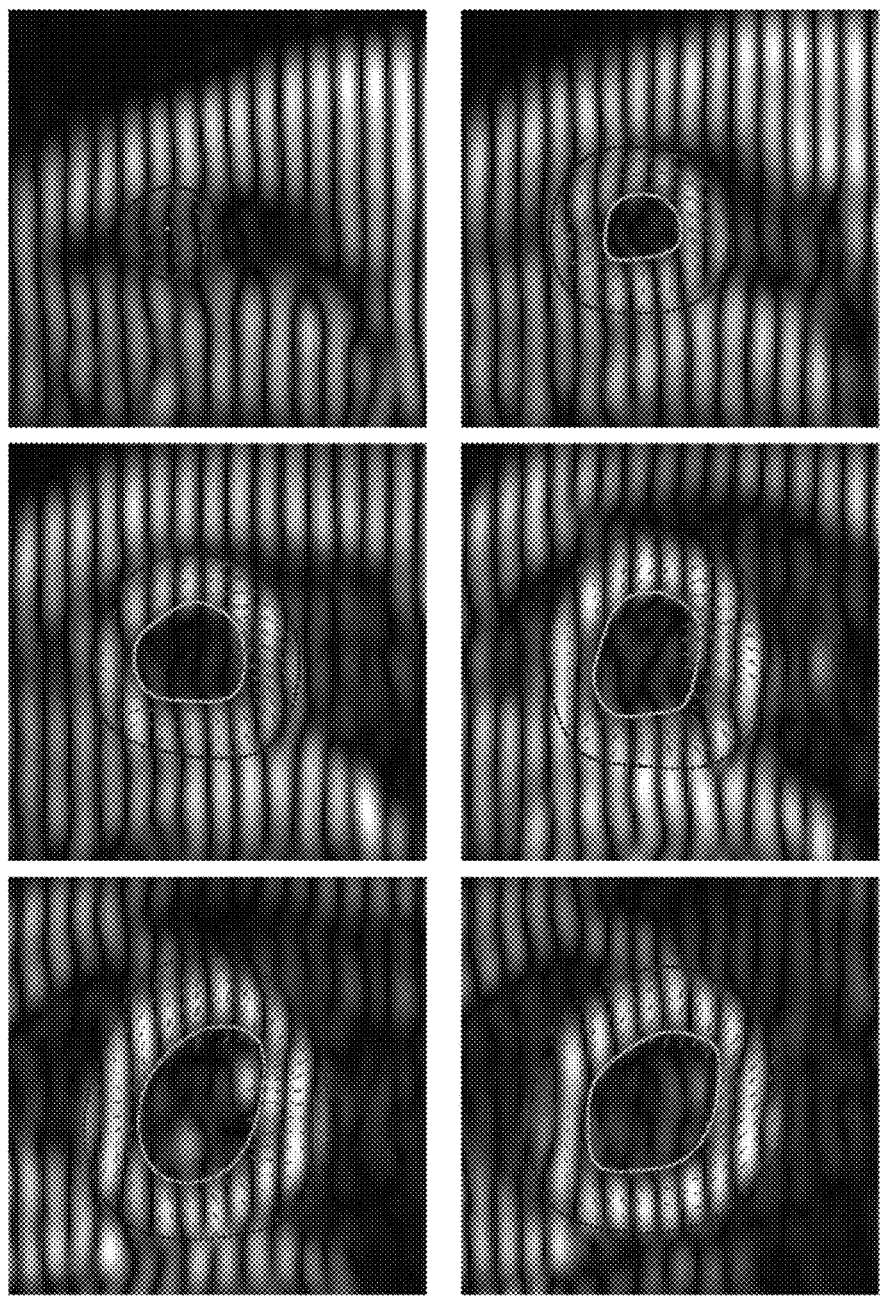
FIG. 34 is a projected 2-D end-systolic motion field on slices 1, 3, 5, 7, 9, 10 for data set 4 (row 1: apex, row 2: mid-ventricular, row 3: base).
Figure 35:
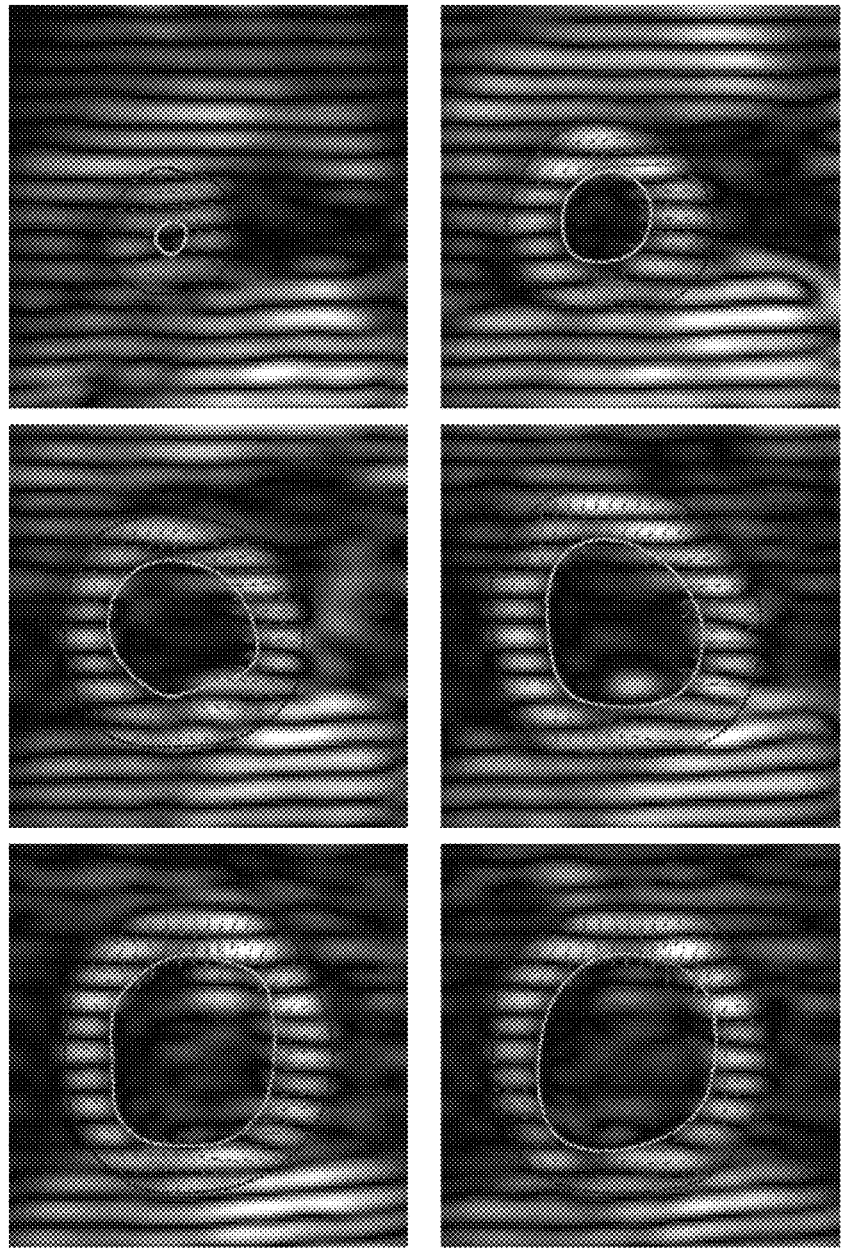
FIG. 35 is a projected 2-D end-systolic motion field on slices 1, 3, 5, 7, 9, 10 for data set 5 (row 1: apex, row 2: mid-ventricular, row 3: base).
Figure 36:
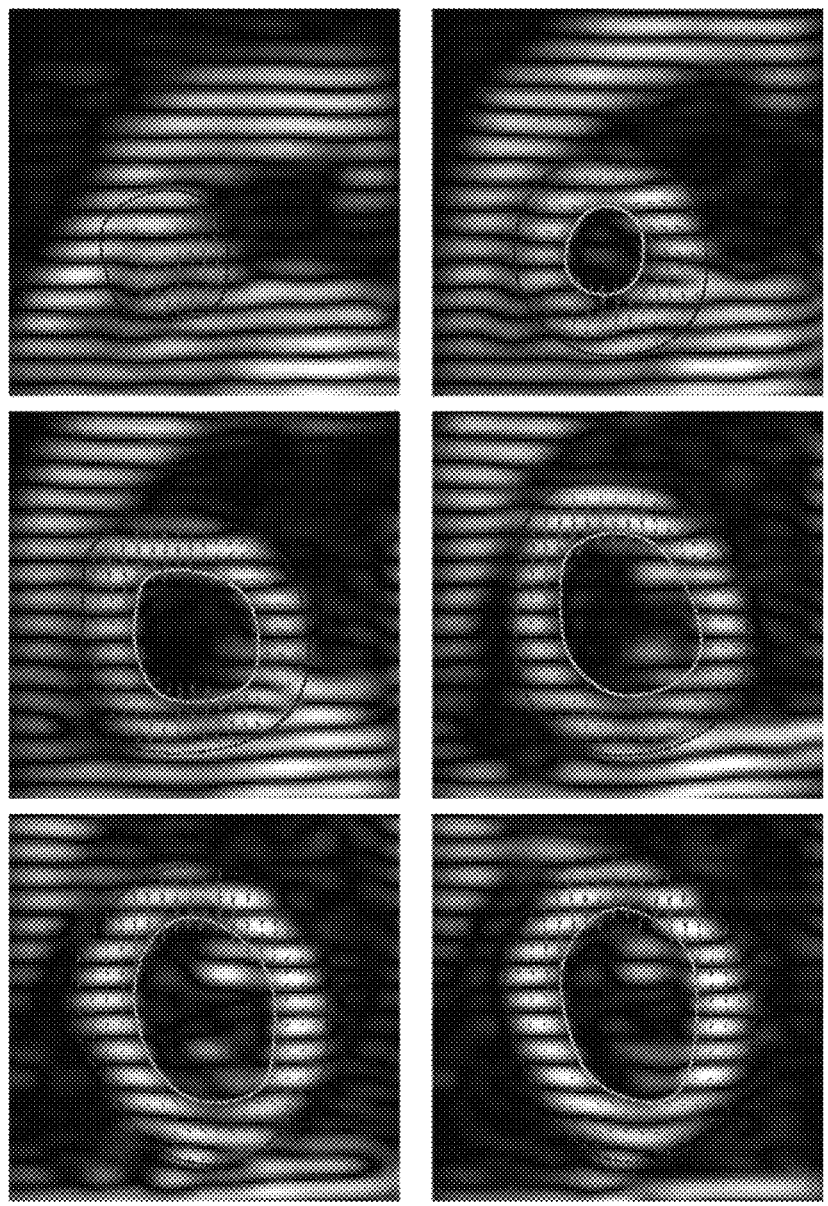
FIG. 36 is a projected 2-D end-systolic motion field on slices 1, 3, 5, 7, 9, 10 for data set 6 (row 1: apex, row 2: mid-ventricular, row 3: base).
Figure 37:
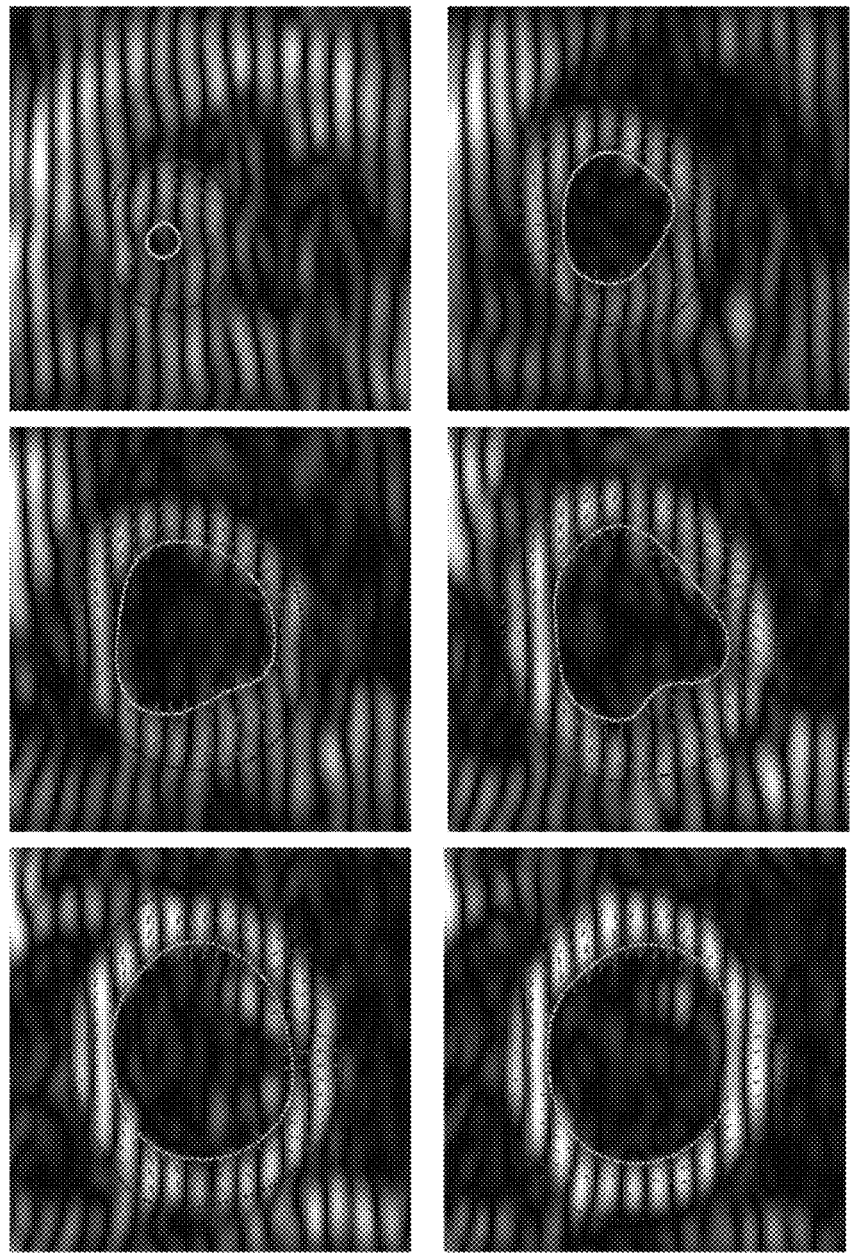
FIG. 37 is a projected 2-D end-systolic motion field on slices 1, 3, 5, 7, 9, 10 for data set 7 (row 1: apex, row 2: mid-ventricular, row 3: base).
Figure 38A:
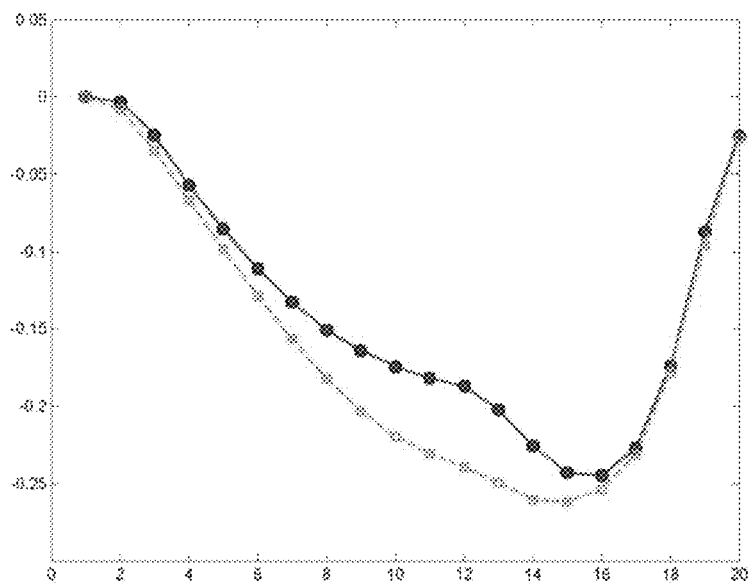
FIG. 38(*a*) is a graph showing calculated circumferential shortening percentage for slice 2 of data set 1.
Figure 38B:
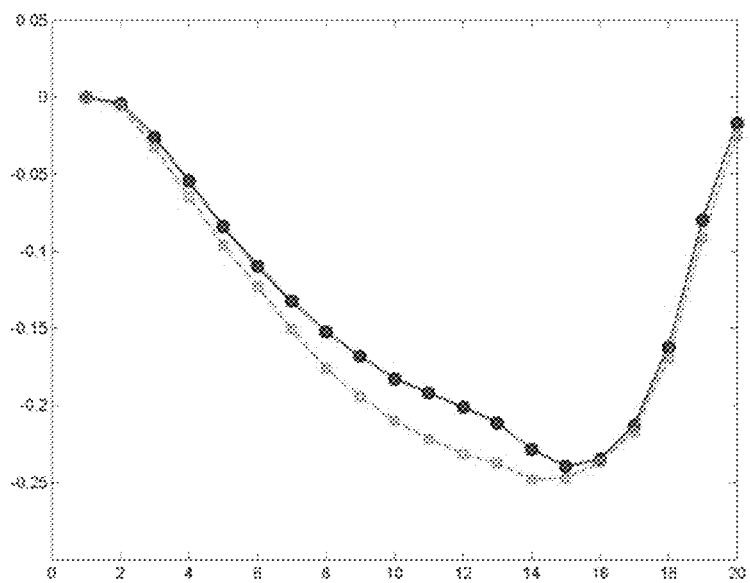
Figure 38C:
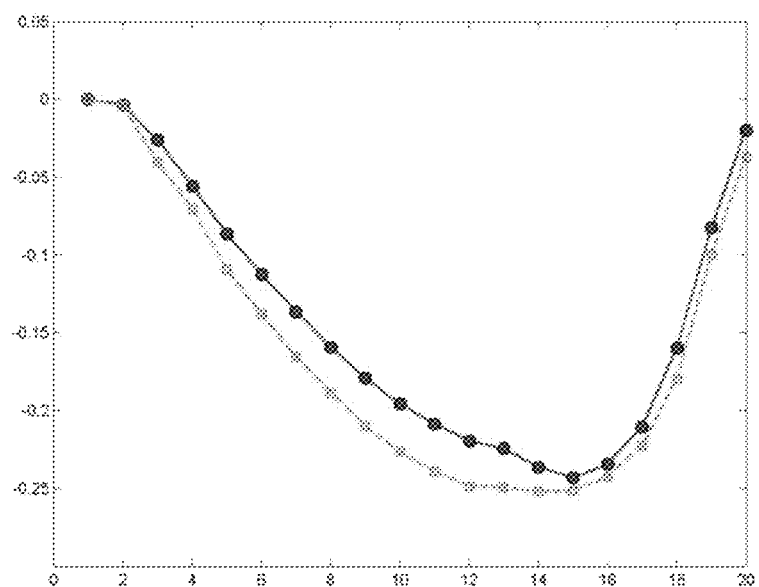
Figure 38D:
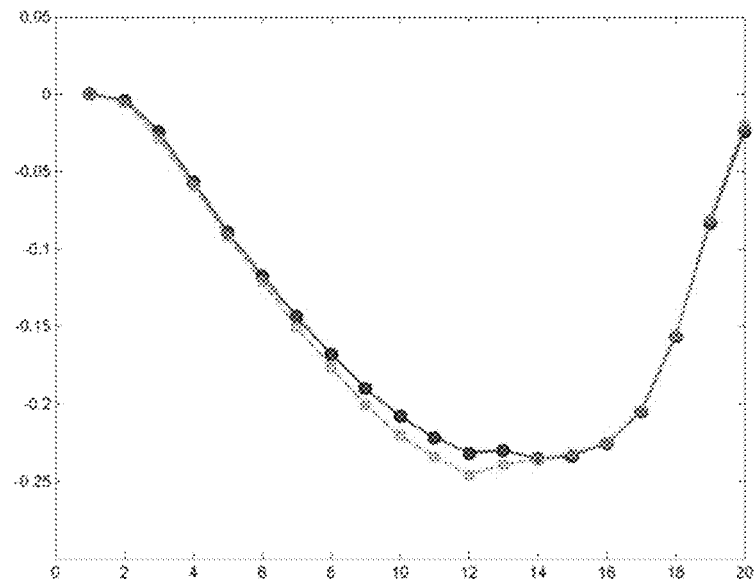
Figure 38E:
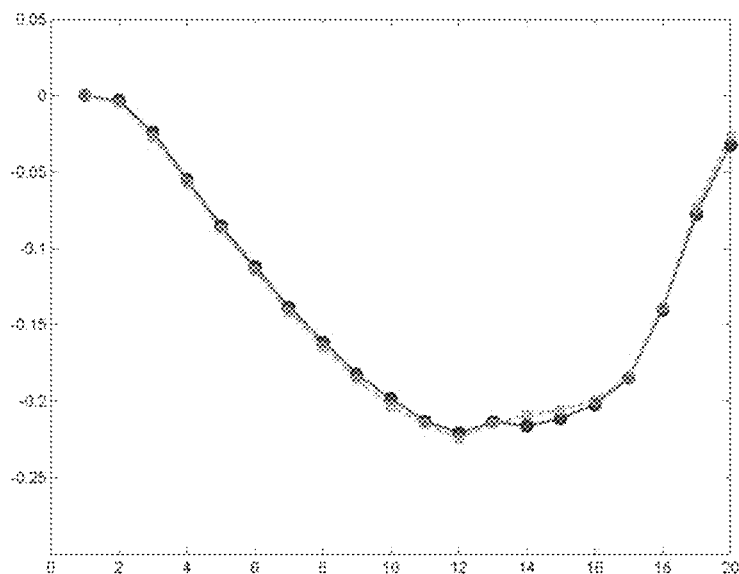
Figure 38F:
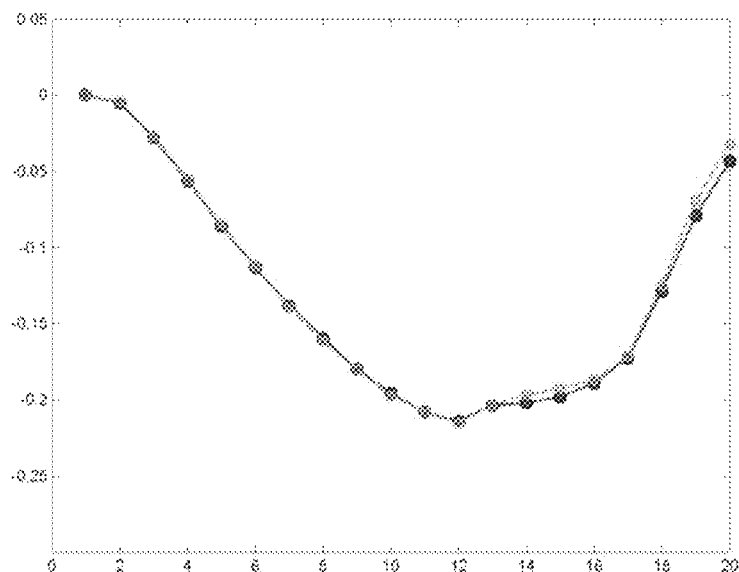

The projected 2D end-systolic motion fields on selected slices for each data set are shown in FIG. 31 to FIG. 37. FIG. 31 is the end systolic motion field on slices 1, 3, 5, 7, 9, 10 for data set 1. FIG. 32 is the end systolic motion field on slices 1, 3, 5, 7, 9, 10 for data set 2. FIG. 33 is the end systolic motion field on slices 1, 3, 5, 7, 9, 10 for data set 3. FIG. 34 is the end systolic motion field on slices 1, 3, 5, 7, 9, 10 for data set 4. FIG. 35 is the end systolic motion field on slices 1, 3, 5, 7, 9, 10 for data set 5. FIG. 36 is the end systolic motion field on slices 1, 3, 5, 7, 9, 10 for data set 6. FIG. 37 is the end systolic motion field on slices 1, 3, 5, 7, 9, 10 for data set 7. In each case, row 1 is the apex (i.e., apical location), row 2 is the mid-ventricular (i.e., mid-cavity location), and row 3 is the base (i.e., basal location).

b. Circumferential Shortening

Figure 39A:
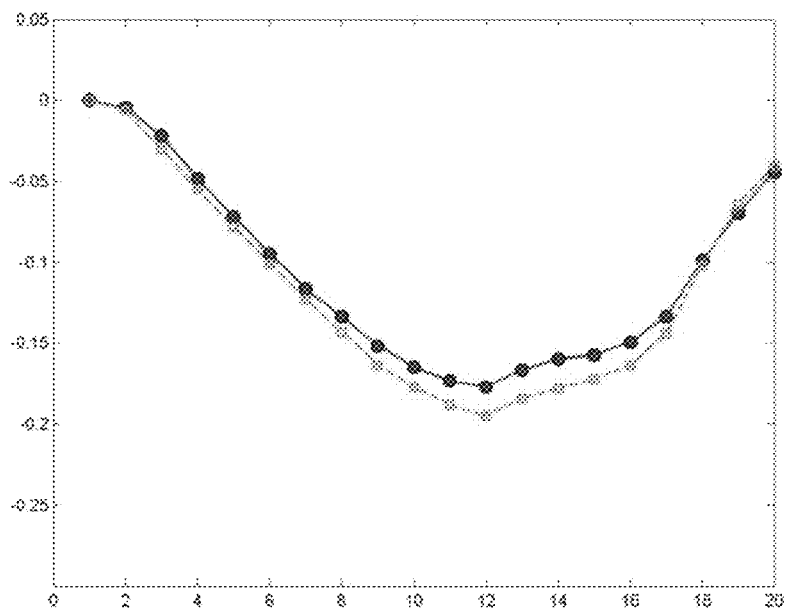
FIG. 39(*a*) is a graph showing calculated circumferential shortening percentage for slice 8 of data set 1.
Figure 39B:
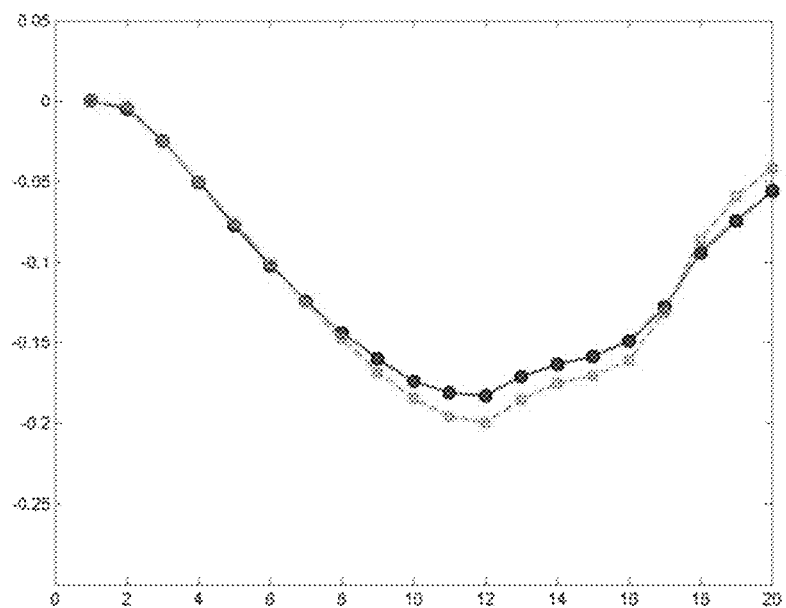
Figure 39C:
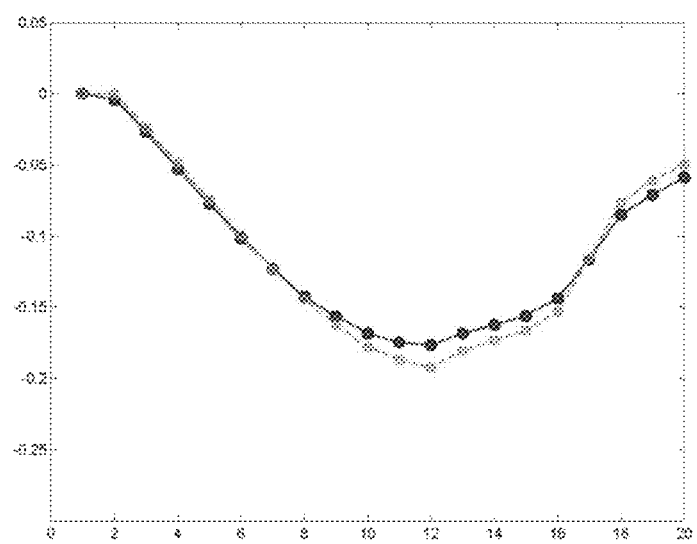
Figure 40A:
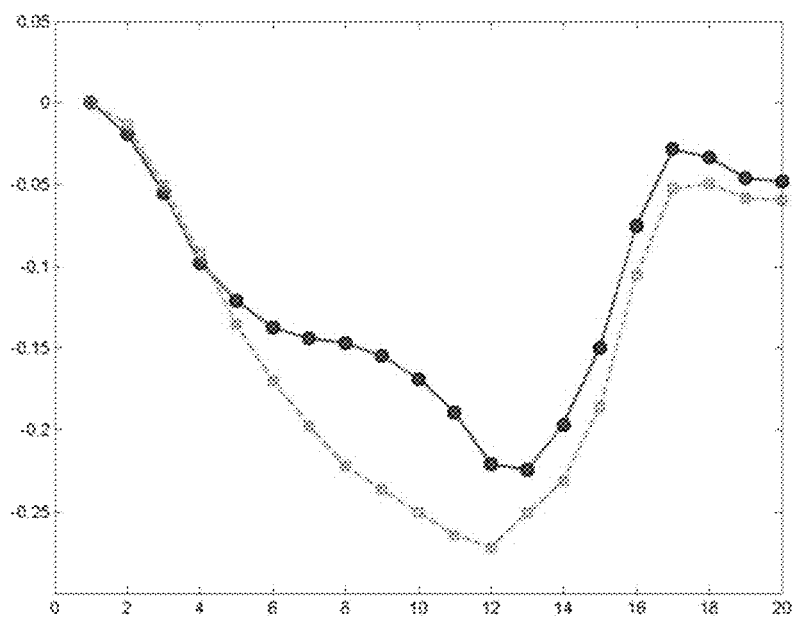
FIG. 40(*a*) is a graph showing calculated circumferential shortening percentage for slice 2 of data set 2.
Figure 40B:
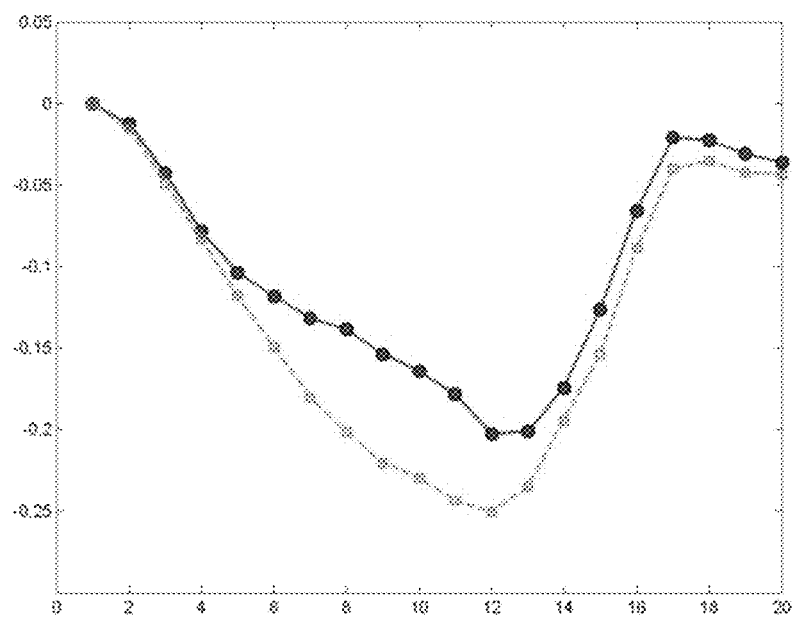
Figure 40C:
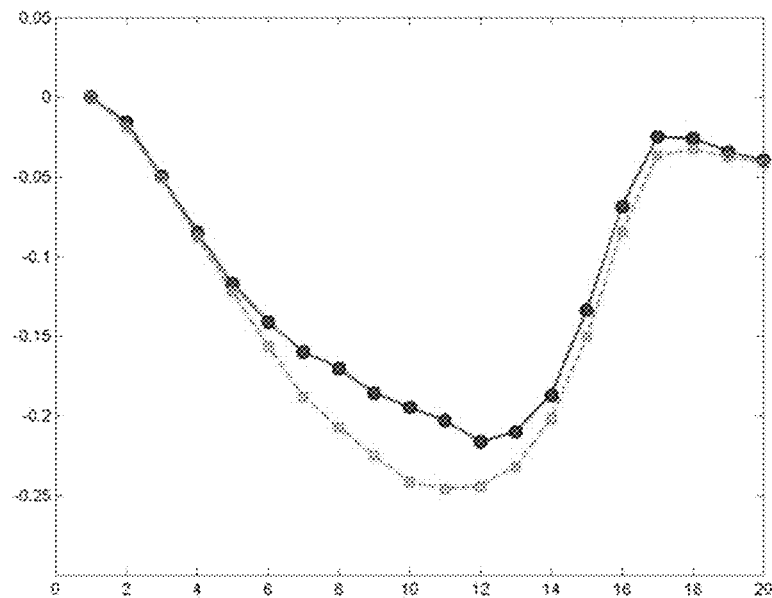
Figure 40D:
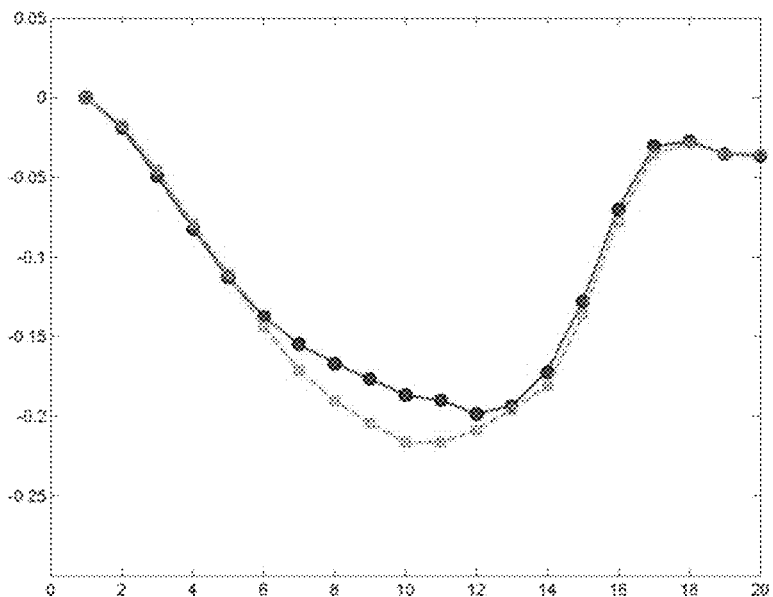
Figure 40E:
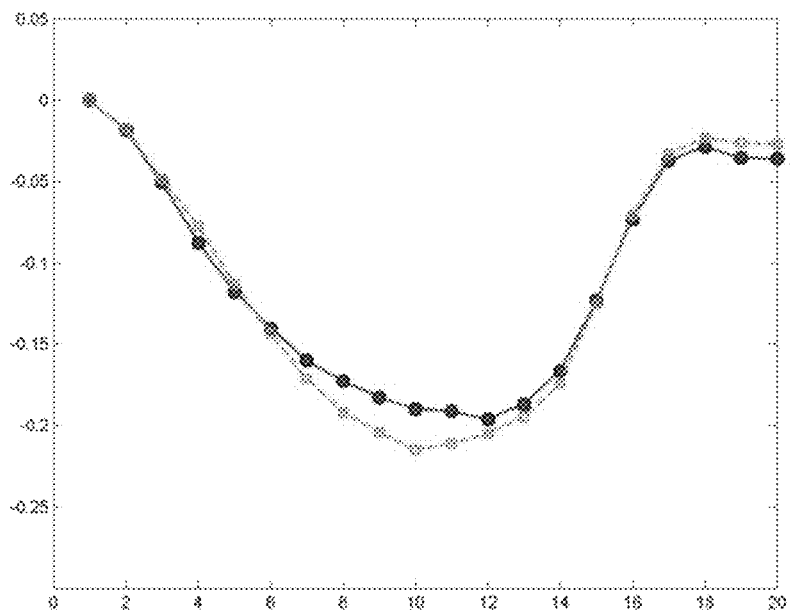
Figure 40F:
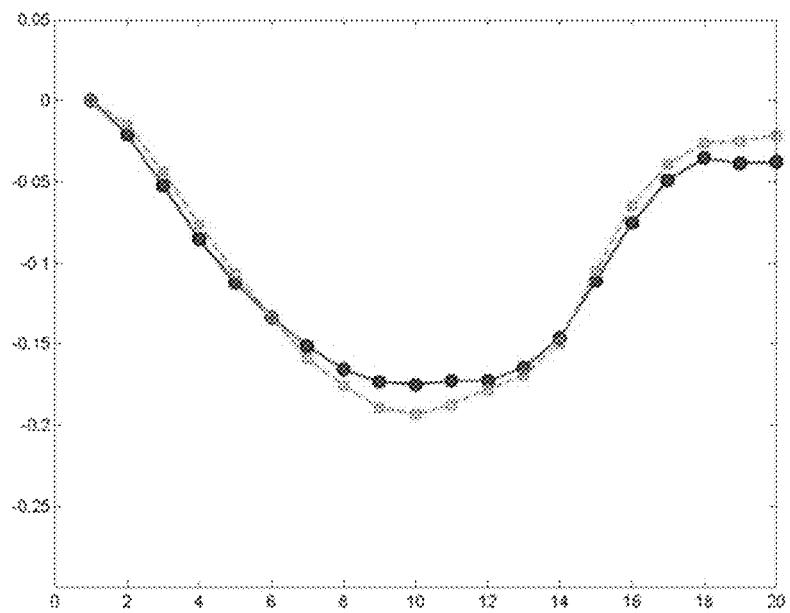
Figure 41A:
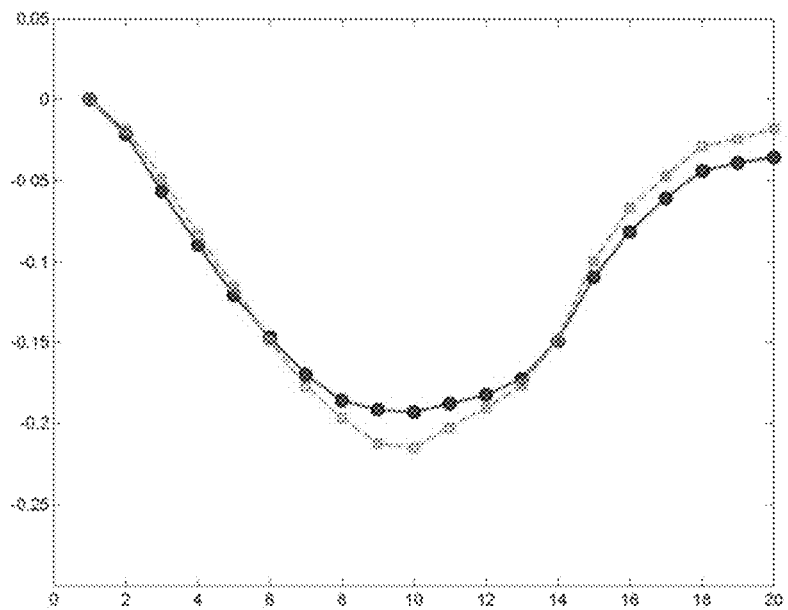
FIG. 41(*a*) is a graph showing calculated circumferential shortening percentage for slice 8 of data set 2.
Figure 41B:
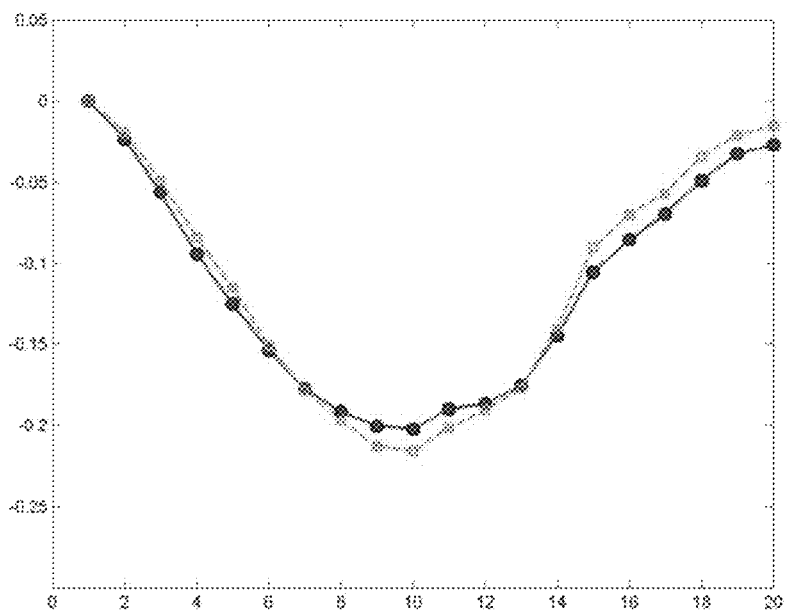
Figure 41C:
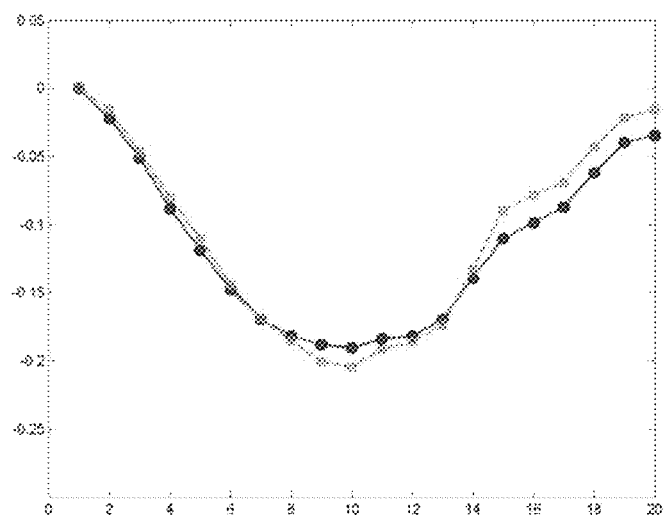
Figure 42A:
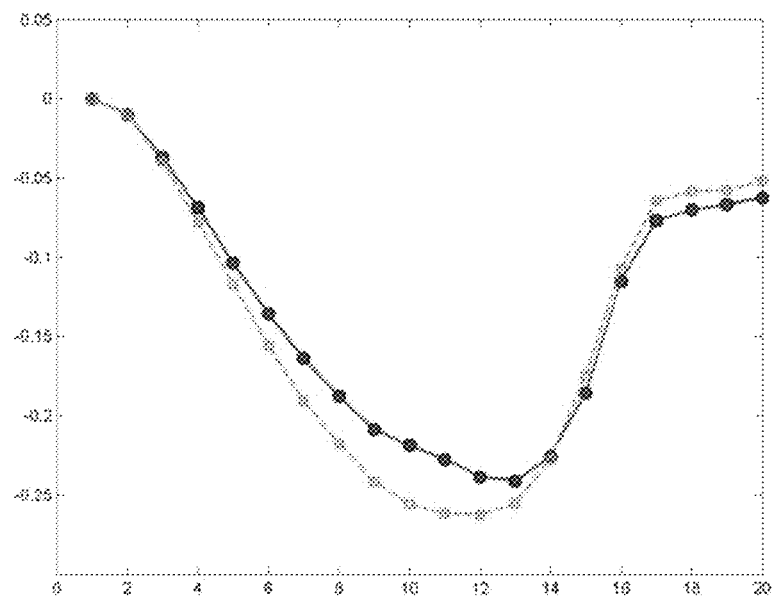
FIG. 42(*a*) is a graph showing calculated circumferential shortening percentage for slice 2 of data set 3.
Figure 42B:
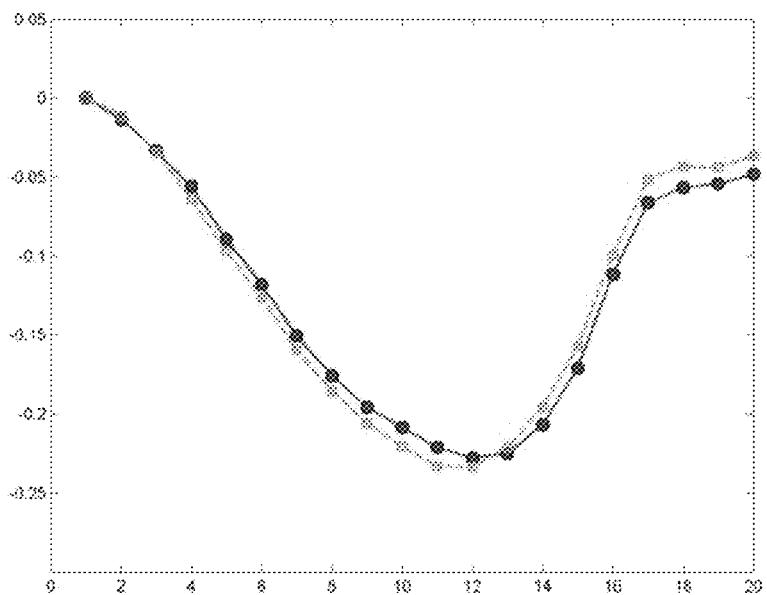
Figure 42C:
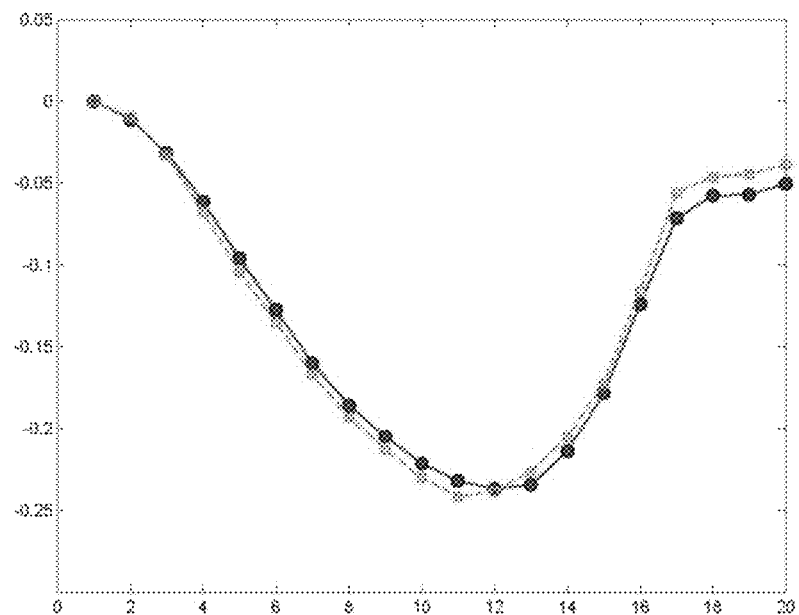
Figure 42D:
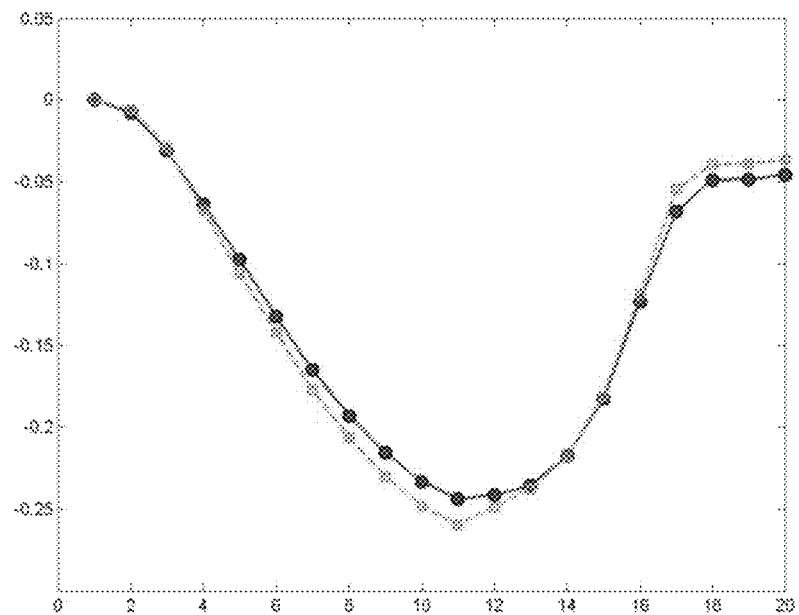
Figure 42E:
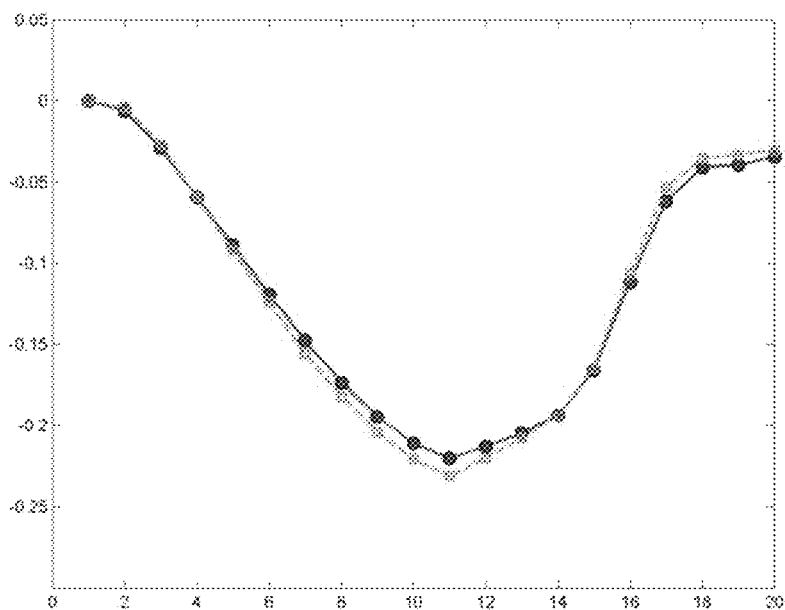
Figure 42F:
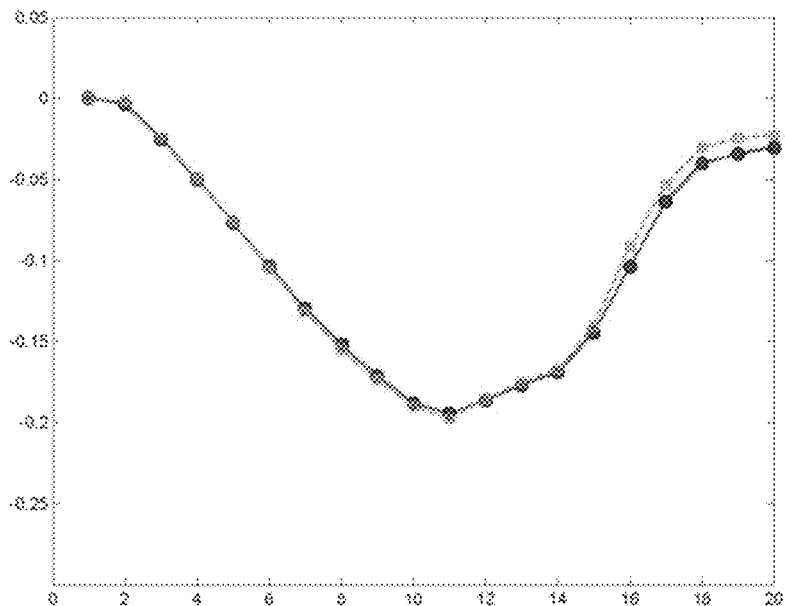
Figure 43A:
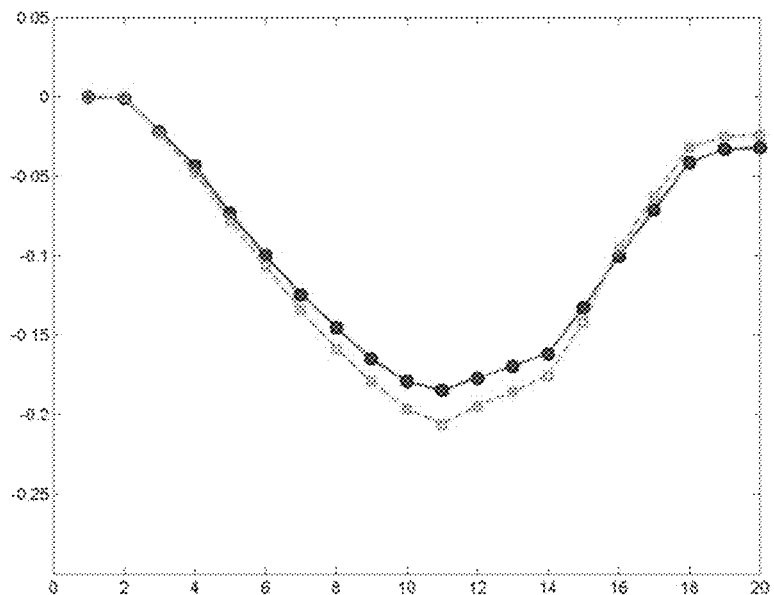
FIG. 43(*a*) is a graph showing calculated circumferential shortening percentage for slice 8 of data set 3.
Figure 43B:
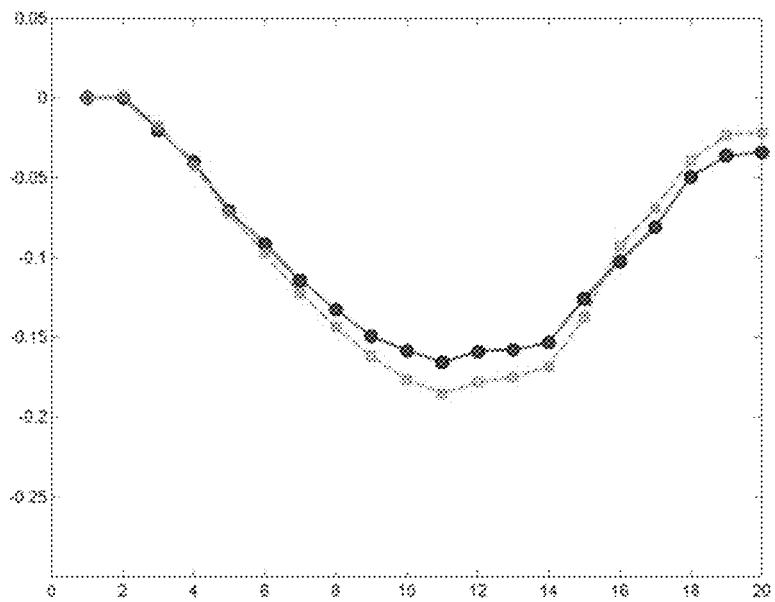
Figure 43C:
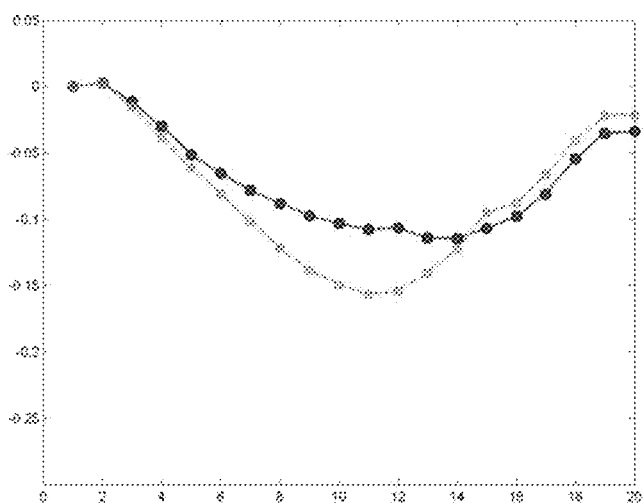
Figure 44A:
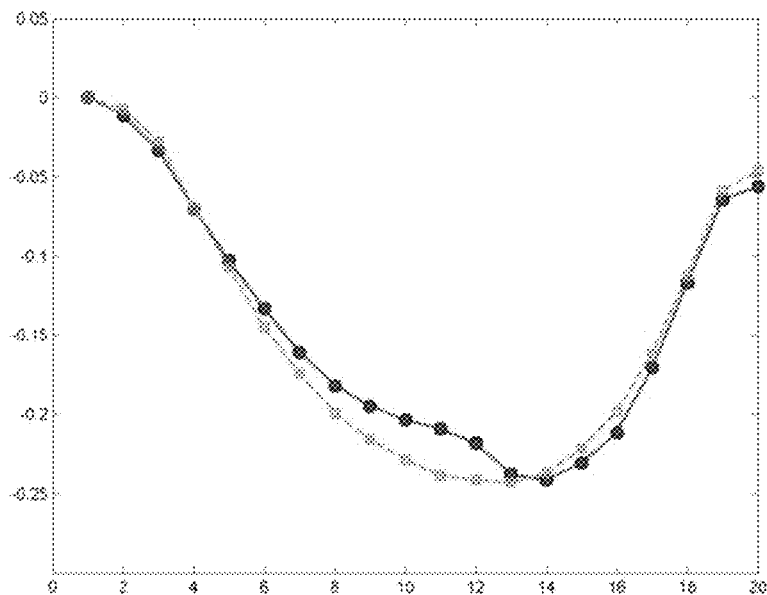
FIG. 44(a) is a graph showing calculated circumferential shortening percentage for slice 2 of data set 4.
Figure 44B:
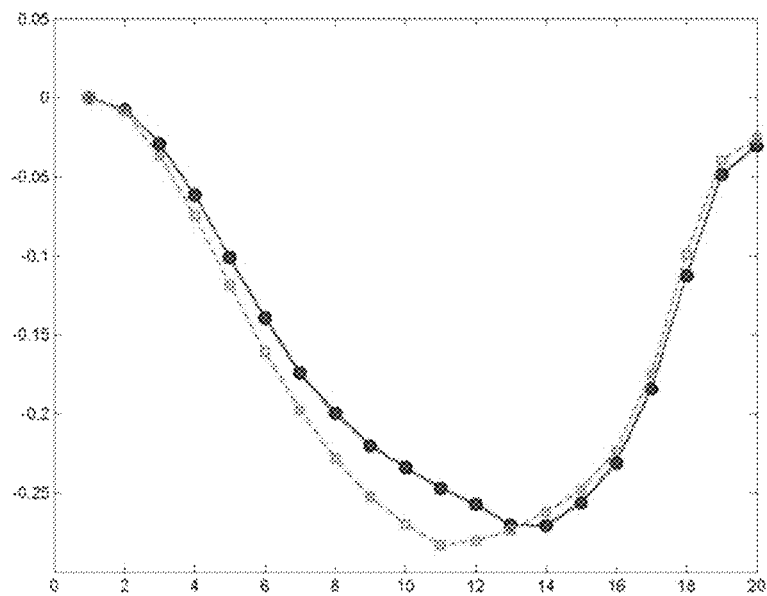
FIG. 44(b) is a graph showing calculated circumferential shortening percentage for slice 3 of data set 4.
Figure 44C:
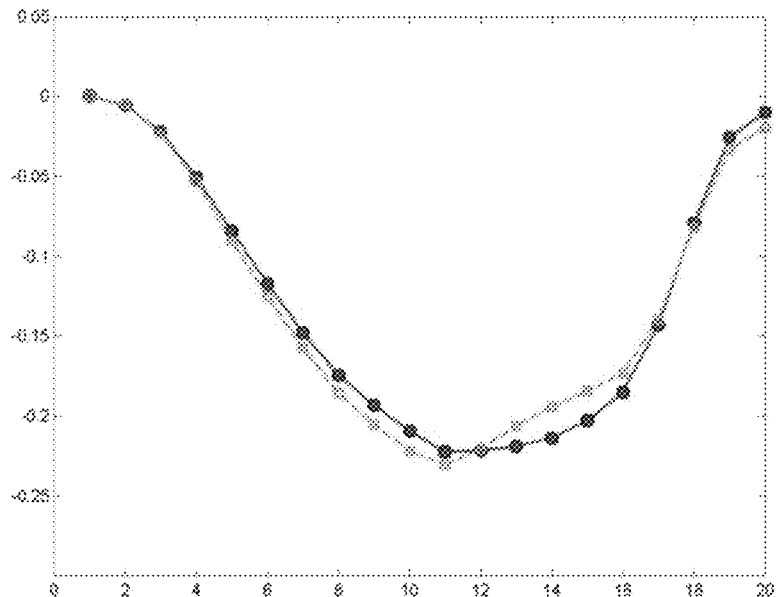
FIG. 44(c) is a graph showing calculated circumferential shortening percentage for slice 4 of data set 4.
Figure 44D:
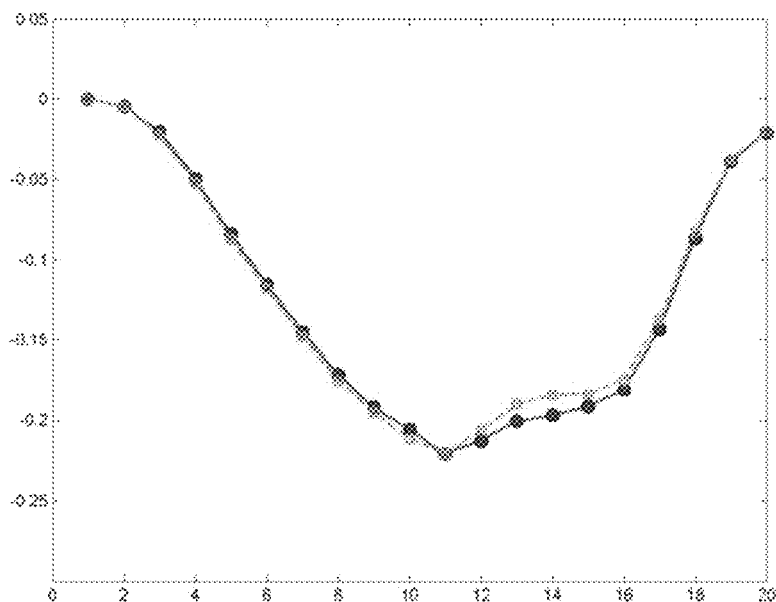
FIG. 44(d) is a graph showing calculated circumferential shortening percentage for slice 5 of data set 4.
Figure 44E:
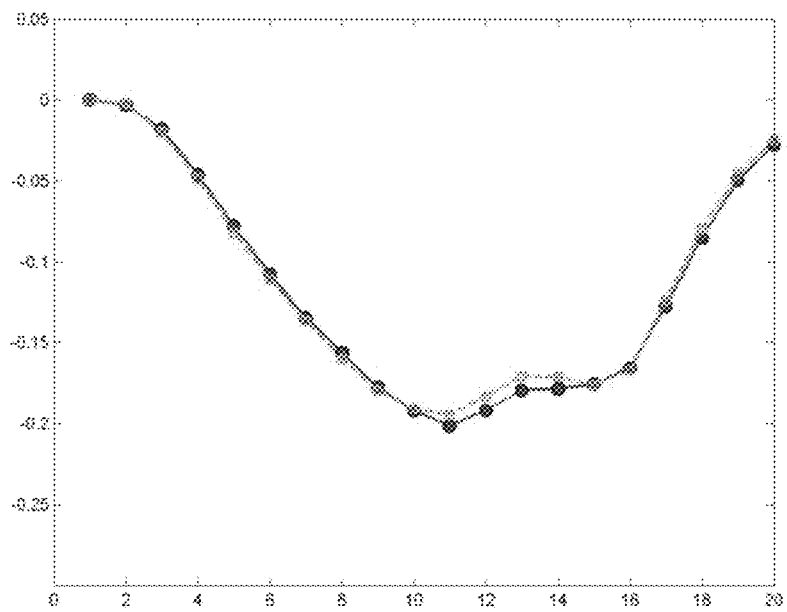
FIG. 44(e) is a graph showing calculated circumferential shortening percentage for slice 6 of data set 4.
Figure 44F:
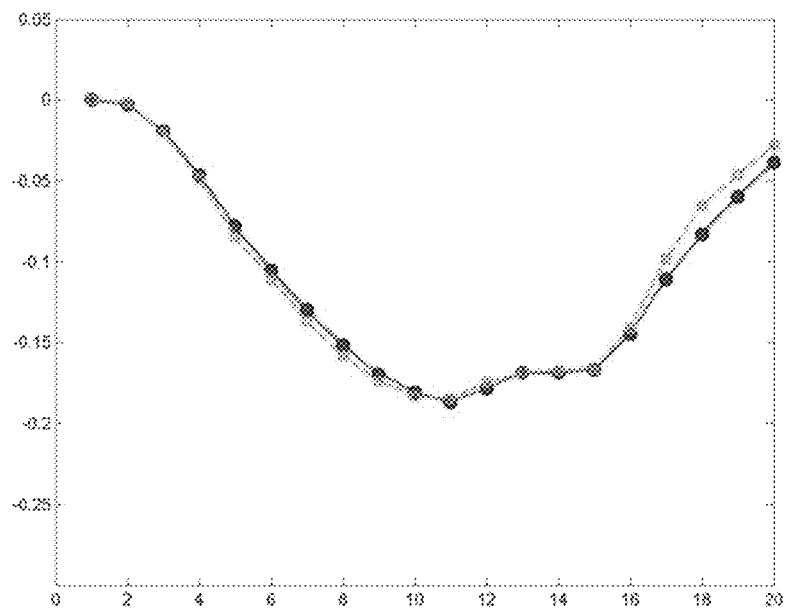
FIG. 44(f) is a graph showing calculated circumferential shortening percentage for slice 7 of data set 4.
Figure 45A:
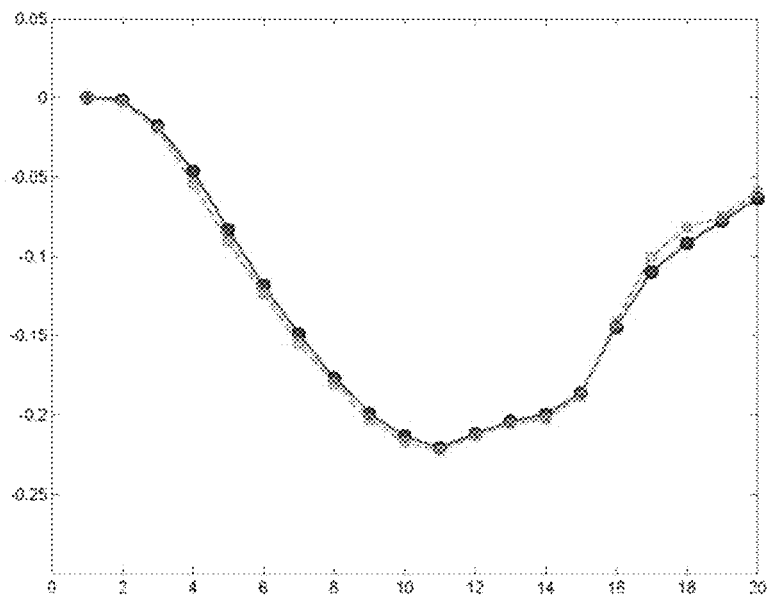
FIG. 45(a) is a graph showing calculated circumferential shortening percentage for slice 8 of data set 4.
Figure 45B:
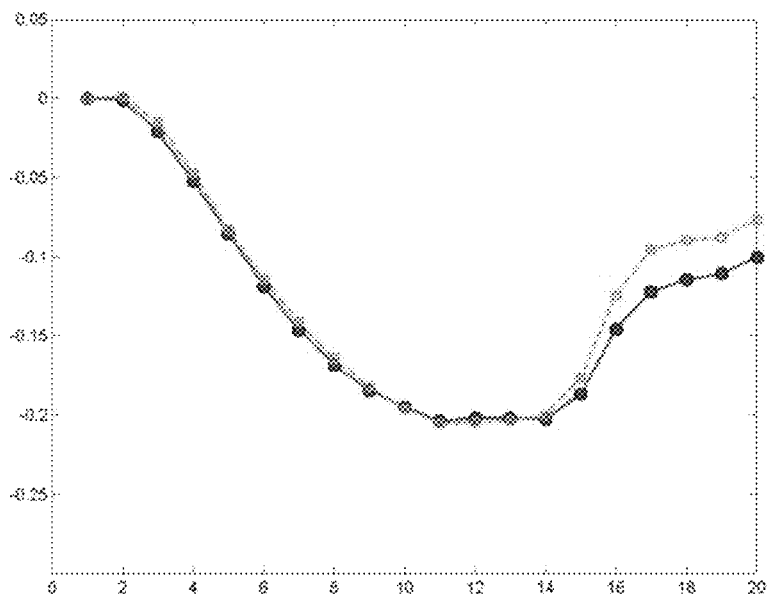
FIG. 45(b) is a graph showing calculated circumferential shortening percentage for slice 9 of data set 4.
Figure 45C:
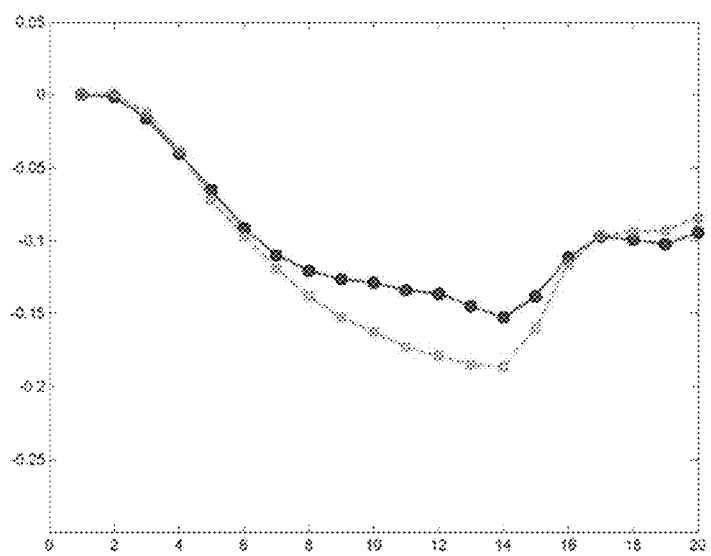
FIG. 45(c) is a graph showing calculated circumferential shortening percentage for slice 10 of data set 4.
Figure 46A:
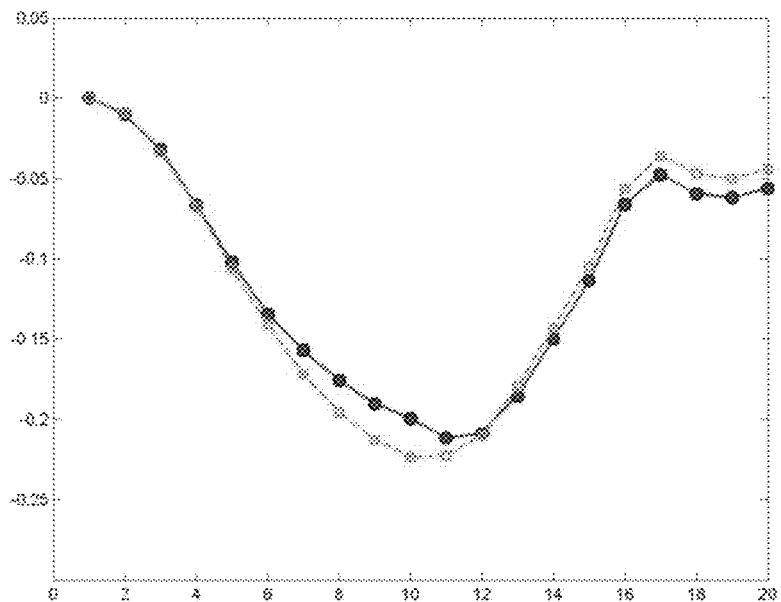
FIG. 46(a) is a graph showing calculated circumferential shortening percentage for slice 2 of data set 5.
Figure 46B:
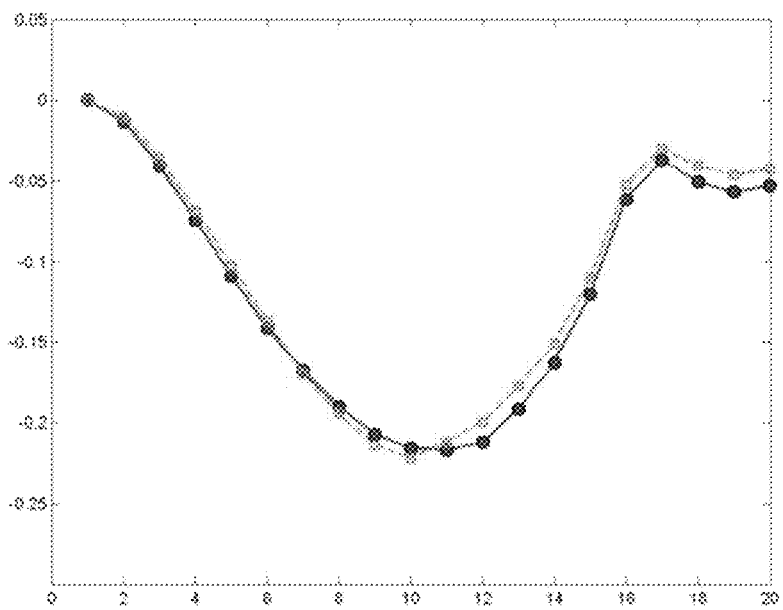
FIG. 46(b) is a graph showing calculated circumferential shortening percentage for slice 3 of data set 5.
Figure 46C:
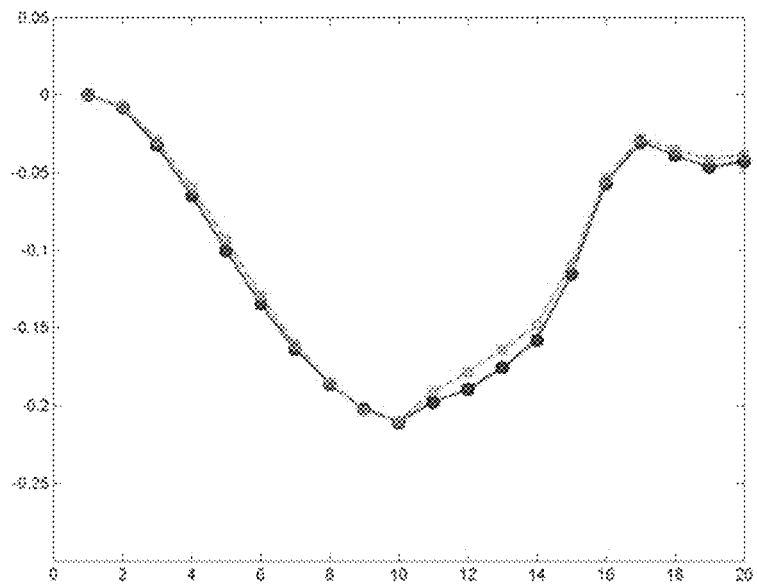
FIG. 46(c) is a graph showing calculated circumferential shortening percentage for slice 4 of data set 5.
Figure 46D:
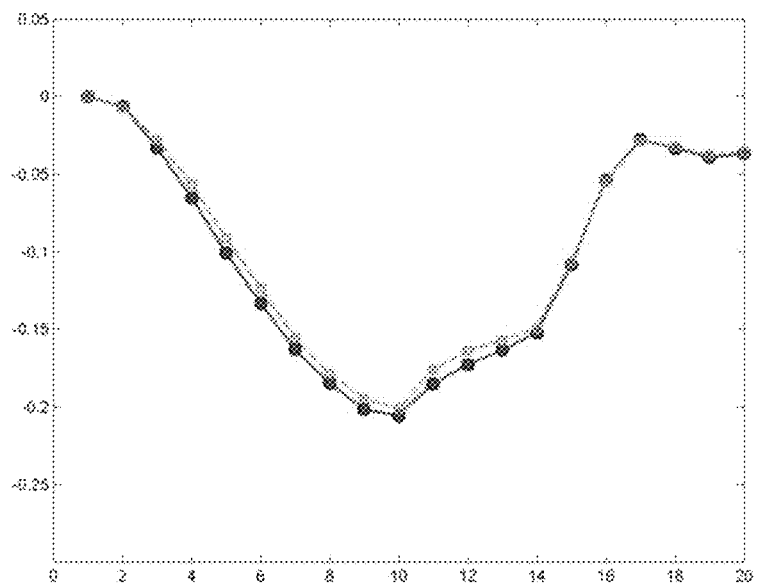
FIG. 46(d) is a graph showing calculated circumferential shortening percentage for slice 5 of data set 5.
Figure 46E:
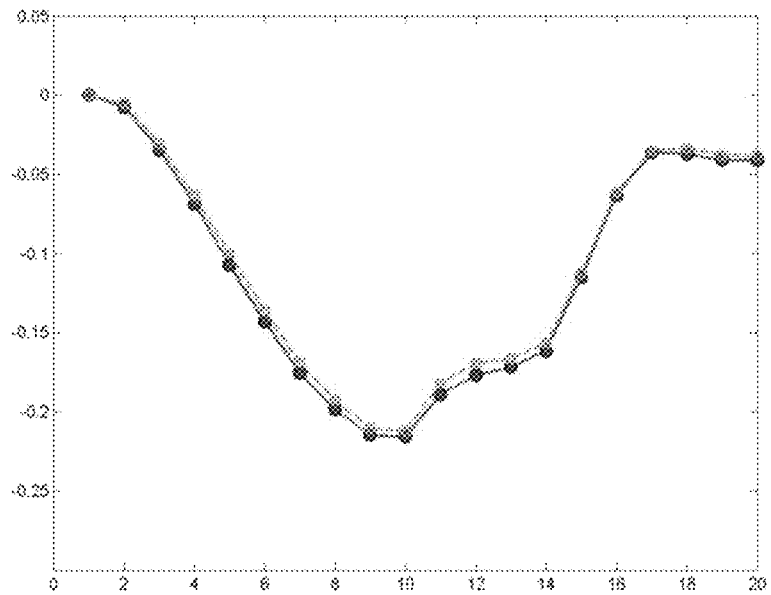
FIG. 46(e) is a graph showing calculated circumferential shortening percentage for slice 6 of data set 5.
Figure 46F:
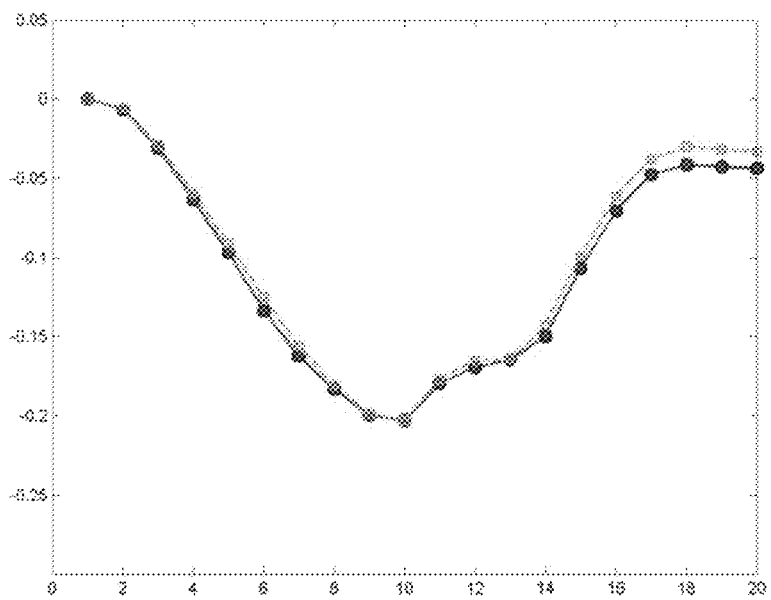
FIG. 46(f) is a graph showing calculated circumferential shortening percentage for slice 7 of data set 5.
Figure 47A:
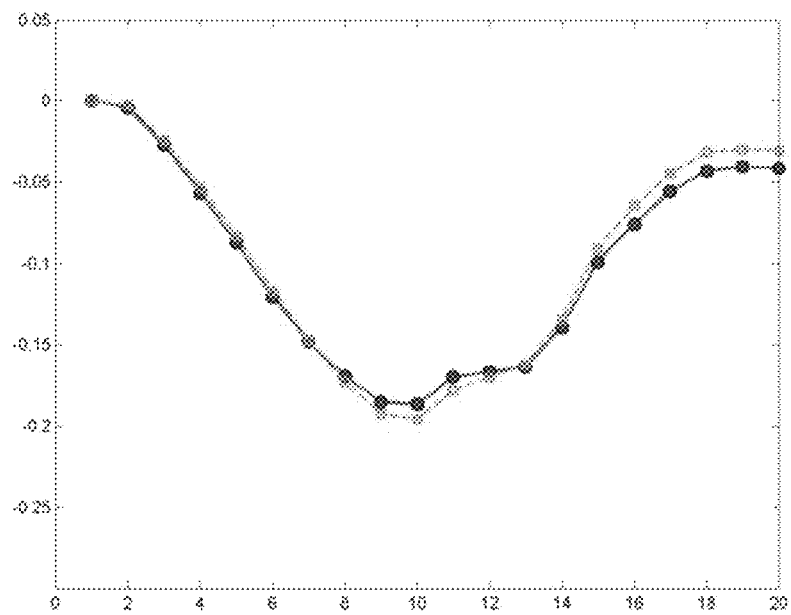
FIG. 47(a) is a graph showing calculated circumferential shortening percentage for slice 8 of data set 5.
Figure 47B:
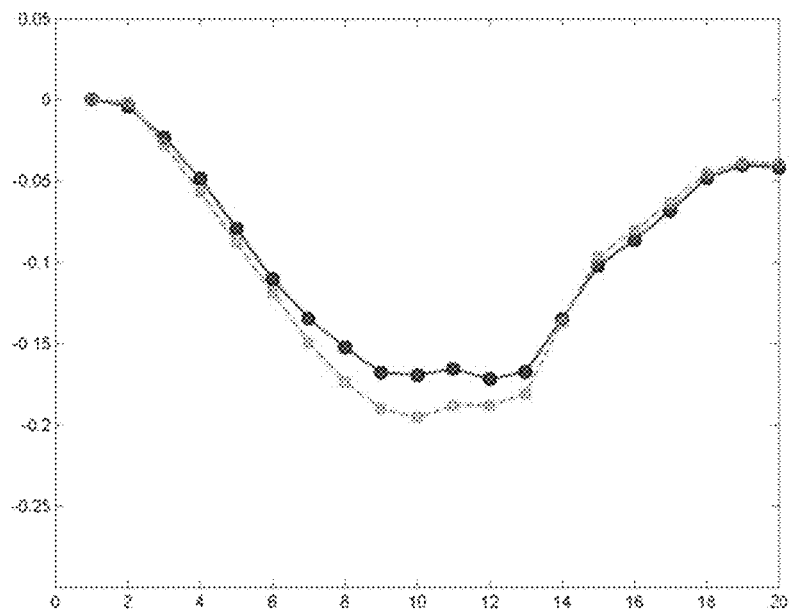
FIG. 47(b) is a graph showing calculated circumferential shortening percentage for slice 9 of data set 5.
Figure 47C:
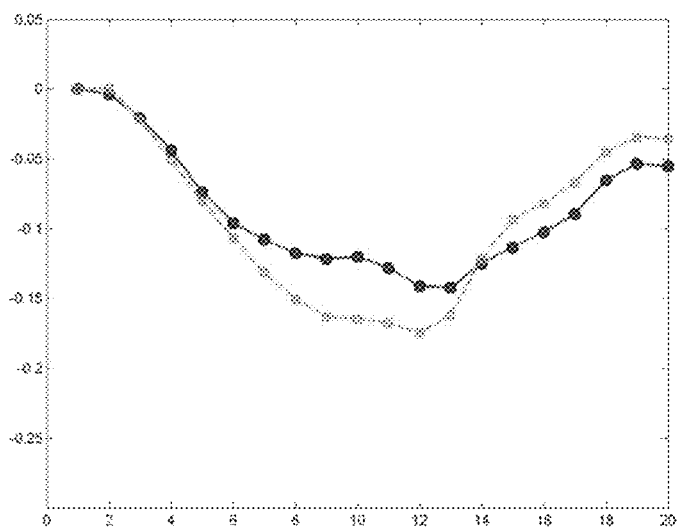
FIG. 47(c) is a graph showing calculated circumferential shortening percentage for slice 10 of data set 5.
Figure 48A:
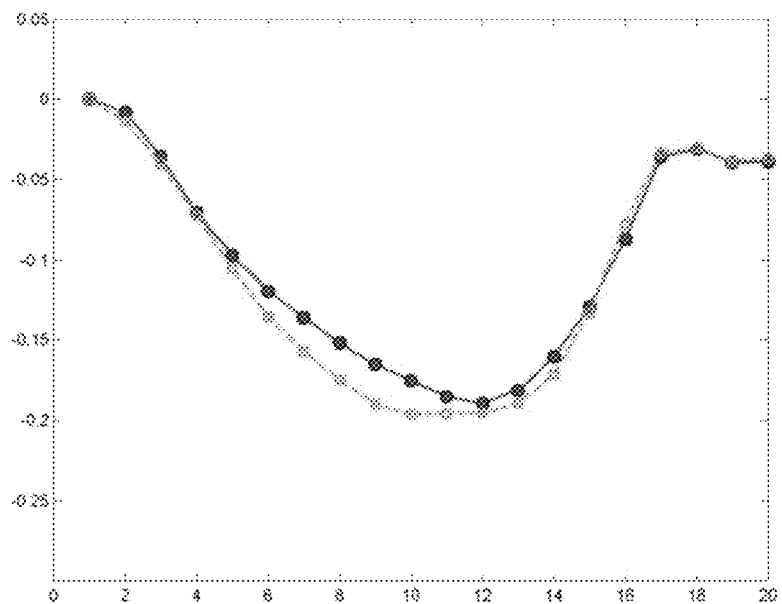
FIG. 48(a) is a graph showing calculated circumferential shortening percentage for slice 2 of data set 6.
Figure 48B:
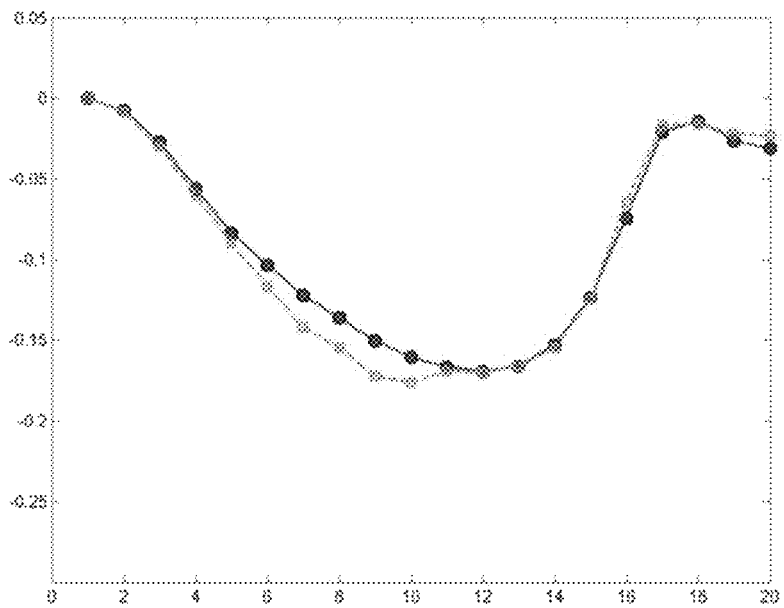
FIG. 48(b) is a graph showing calculated circumferential shortening percentage for slice 3 of data set 6.
Figure 48C:
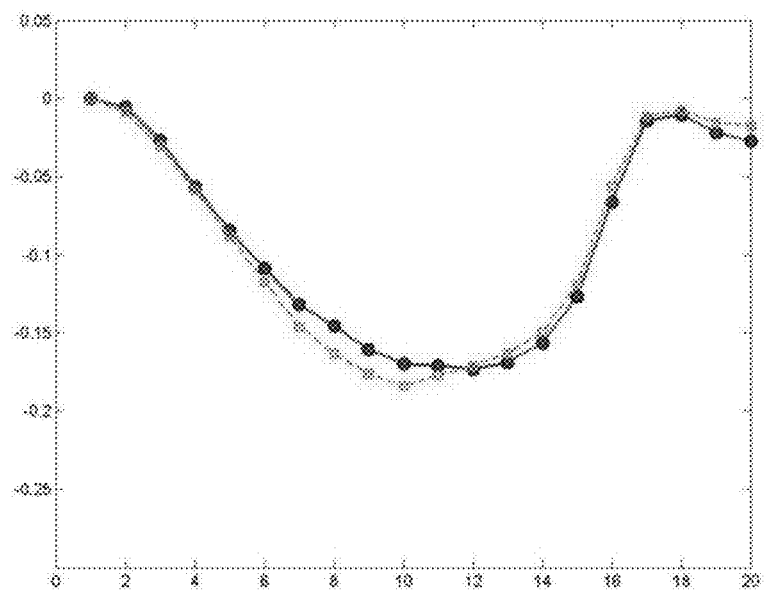
FIG. 48(c) is a graph showing calculated circumferential shortening percentage for slice 4 of data set 6.
Figure 48D:
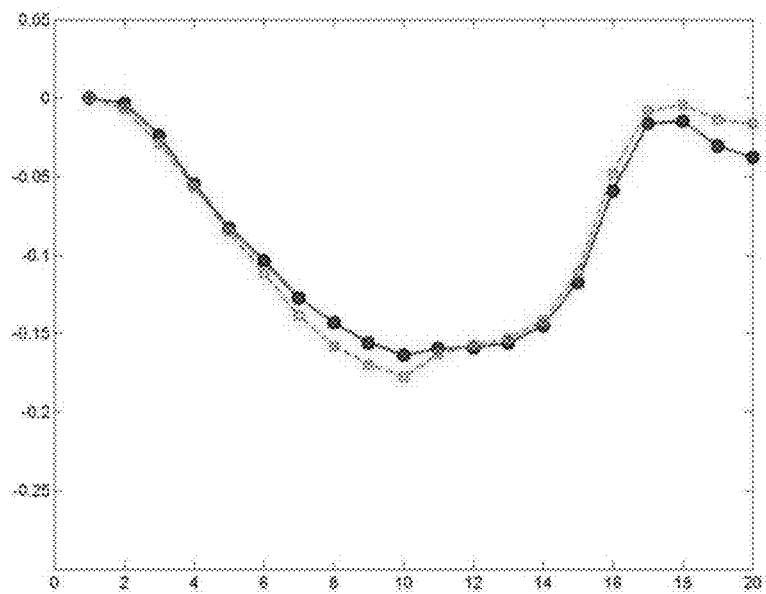
FIG. 48(d) is a graph showing calculated circumferential shortening percentage for slice 5 of data set 6.
Figure 48E:
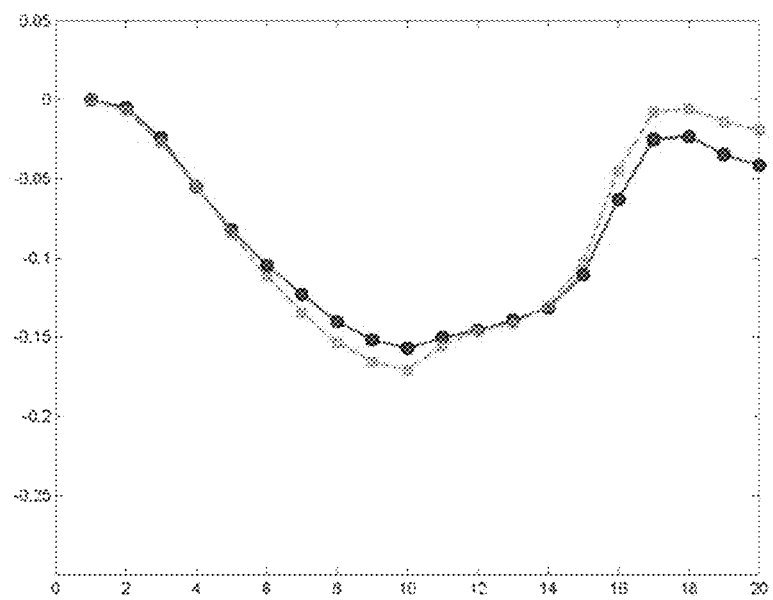
FIG. 48(e) is a graph showing calculated circumferential shortening percentage for slice 6 of data set 6.
Figure 48F:
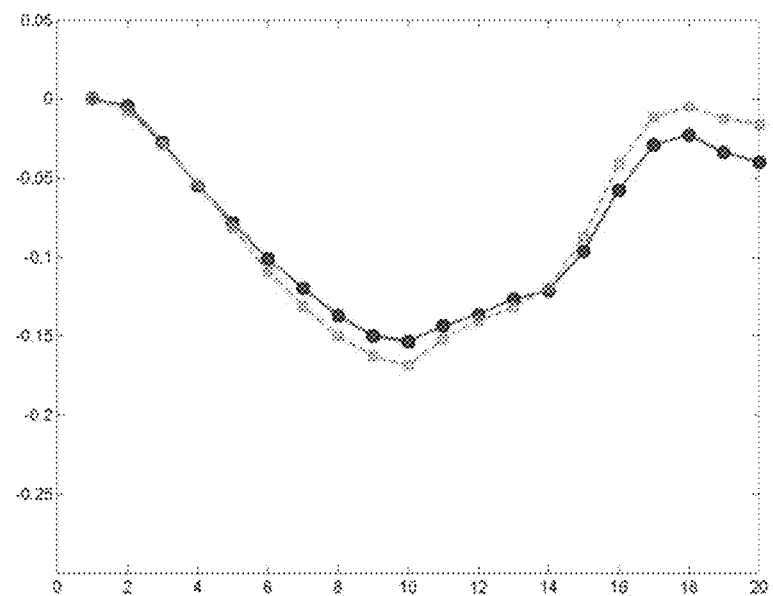
FIG. 48(f) is a graph showing calculated circumferential shortening percentage for slice 7 of data set 6.
Figure 49A:
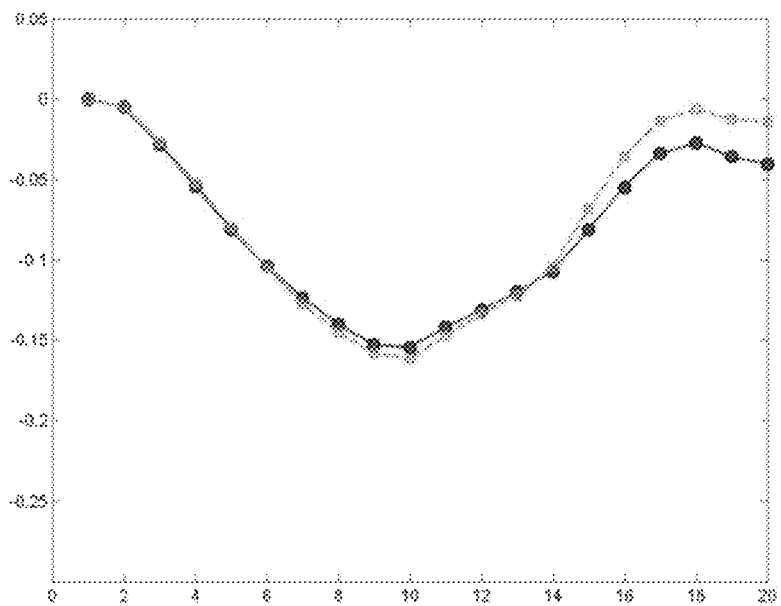
FIG. 49(a) is a graph showing calculated circumferential shortening percentage for slice 8 of data set 6.
Figure 49B:
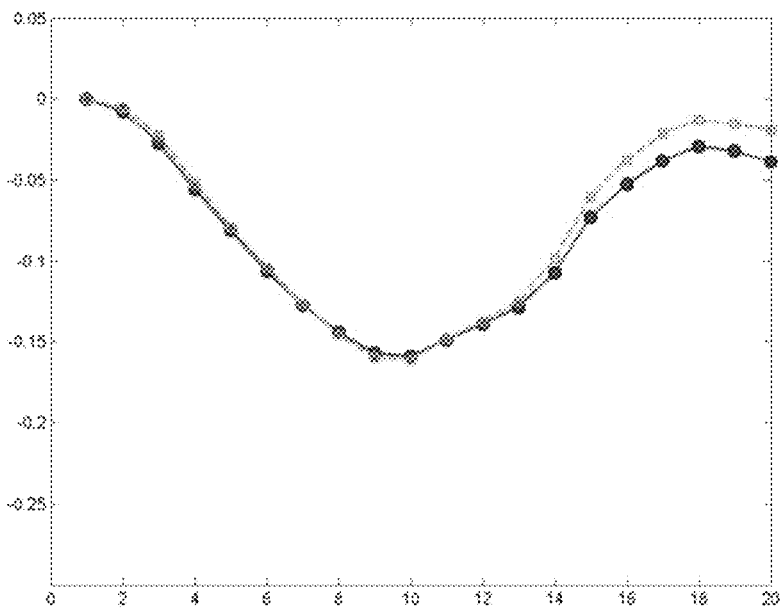
FIG. 49(b) is a graph showing calculated circumferential shortening percentage for slice 9 of data set 6.
Figure 49C:
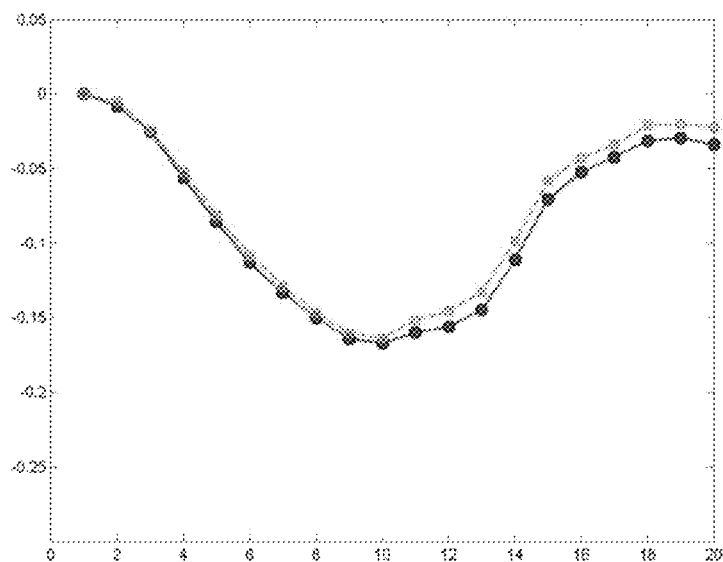
FIG. 49(c) is a graph showing calculated circumferential shortening percentage for slice 10 of data set 6.
Figure 50A:
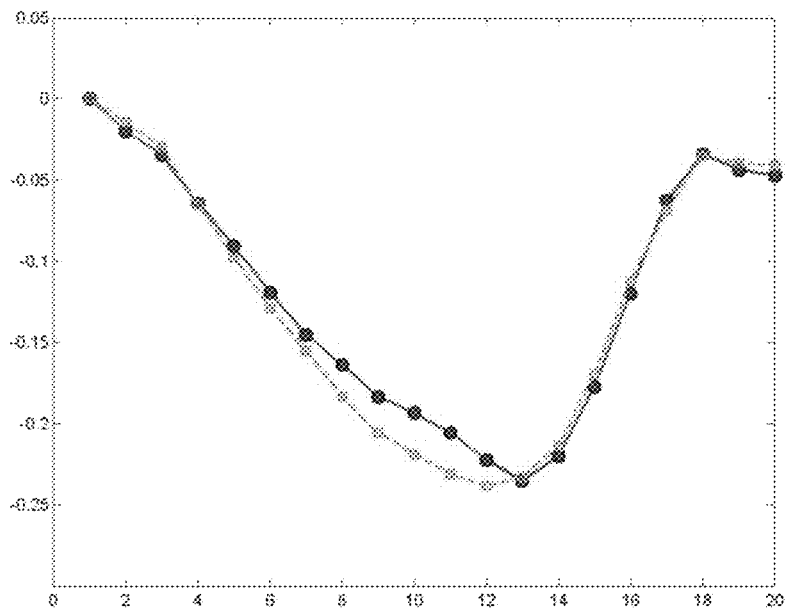
FIG. 50(a) is a graph showing calculated circumferential shortening percentage for slice 2 of data set 7.
Figure 50B:
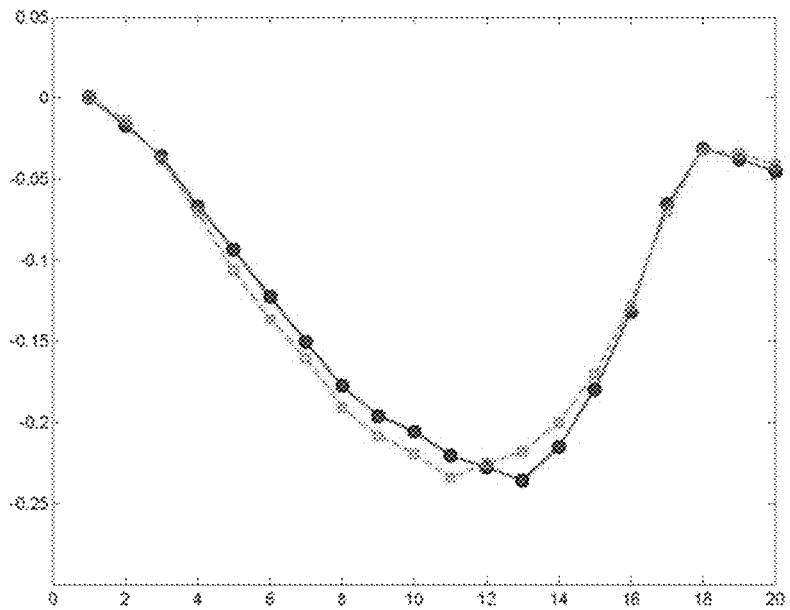
FIG. 50(b) is a graph showing calculated circumferential shortening percentage for slice 3 of data set 7.
Figure 50C:
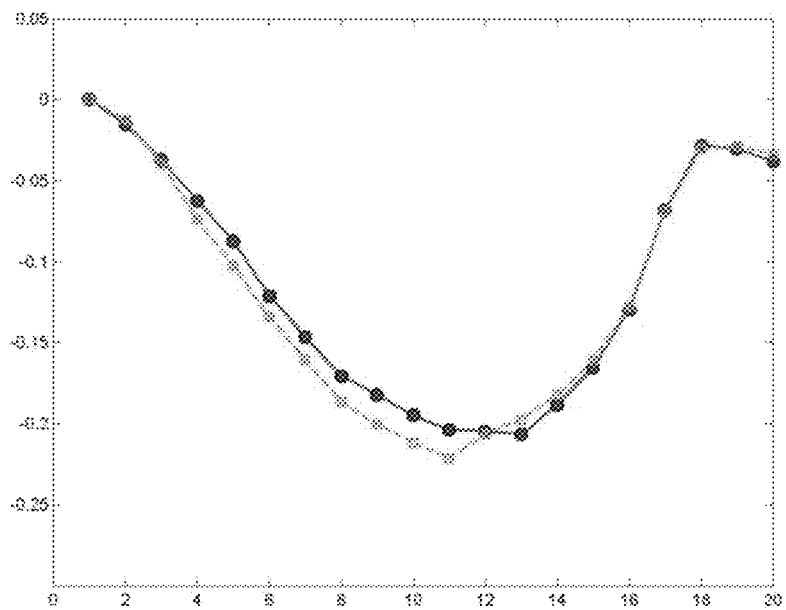
FIG. 50(c) is a graph showing calculated circumferential shortening percentage for slice 4 of data set 7.
Figure 50D:
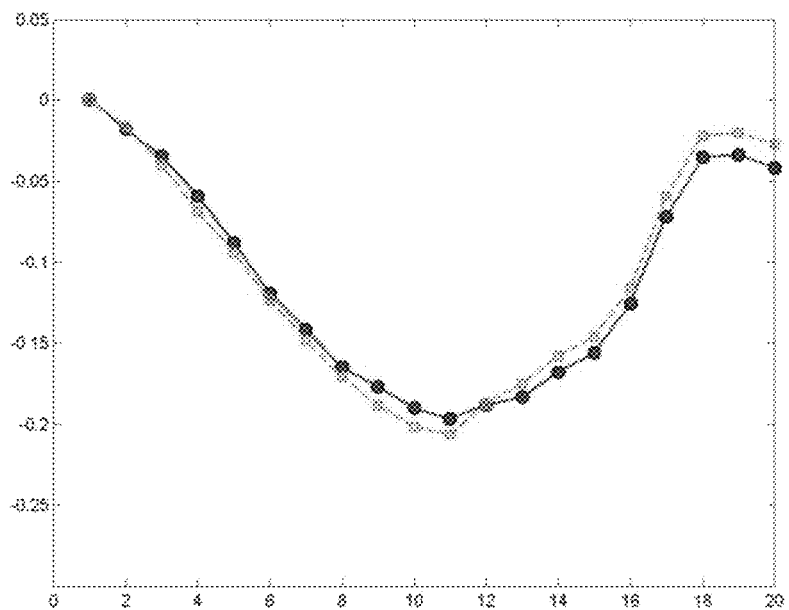
FIG. 50(d) is a graph showing calculated circumferential shortening percentage for slice 5 of data set 7.
Figure 50E:
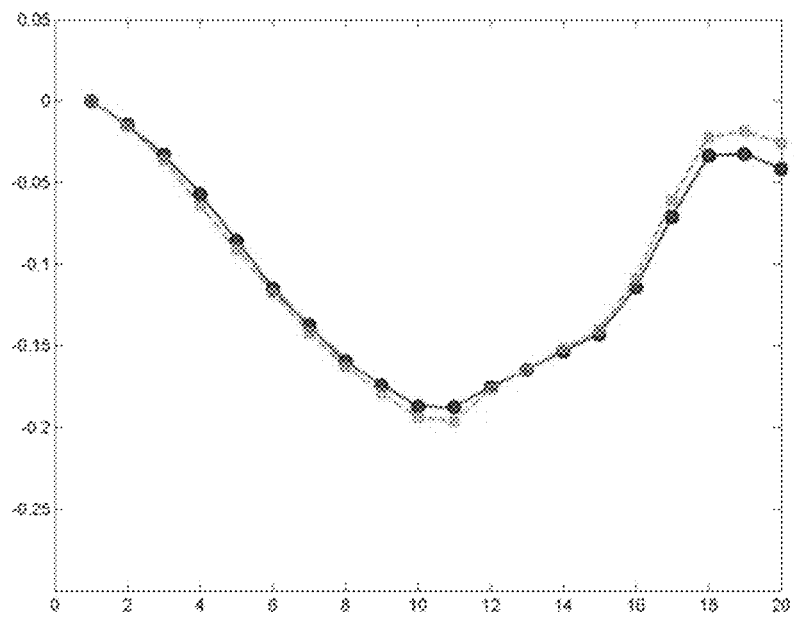
FIG. 50(e) is a graph showing calculated circumferential shortening percentage for slice 6 of data set 7.
Figure 50F:
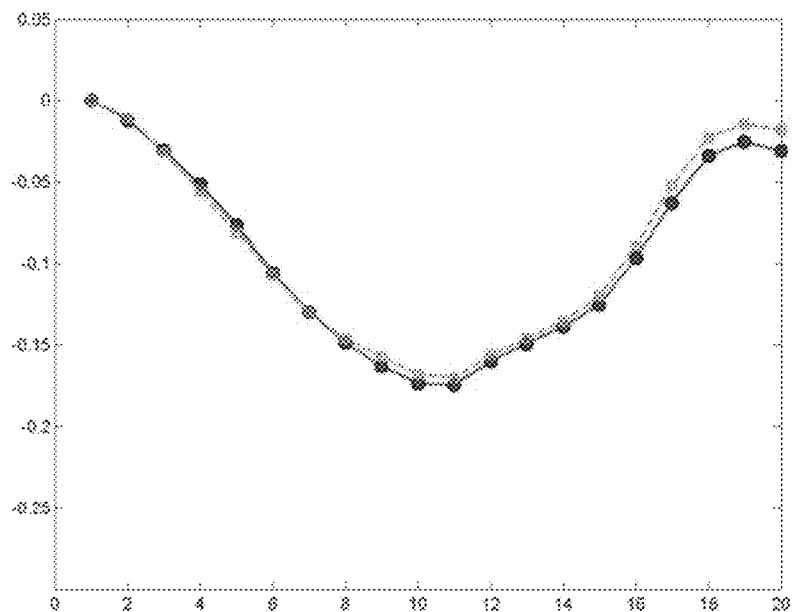
FIG. 50(f) is a graph showing calculated circumferential shortening percentage for slice 7 of data set 7.
Figure 51A:
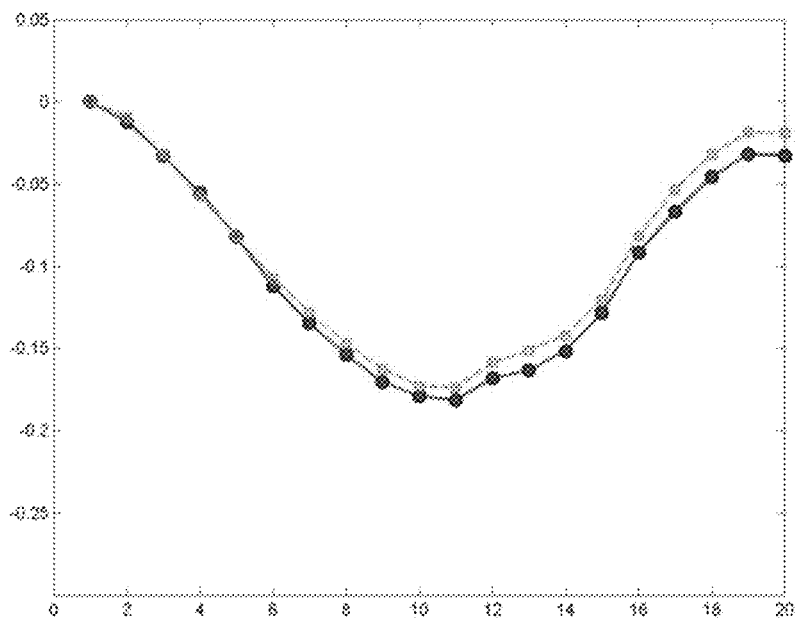
FIG. 51(a) is a graph showing calculated circumferential shortening percentage for slice 8 of data set 7.
Figure 51B:
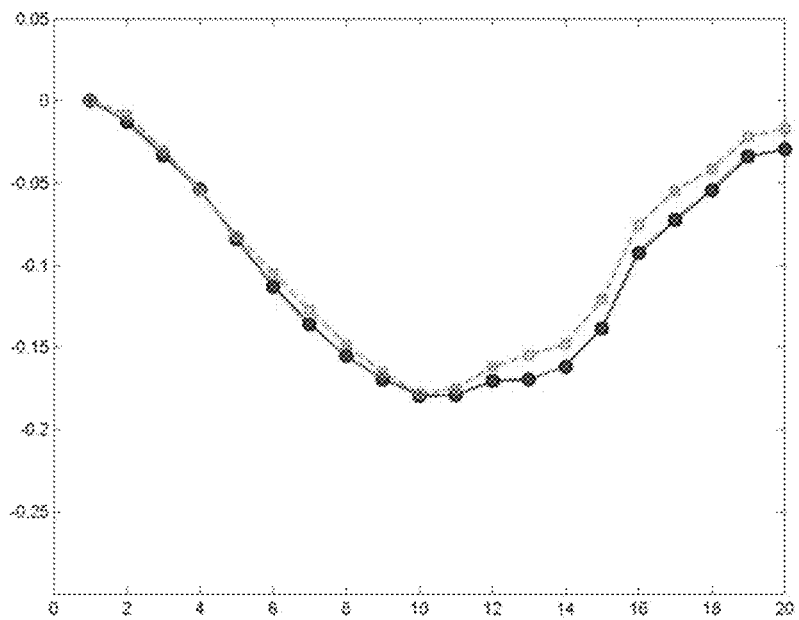
FIG. 51(b) is a graph showing calculated circumferential shortening percentage for slice 9 of data set 7.
Figure 51C:
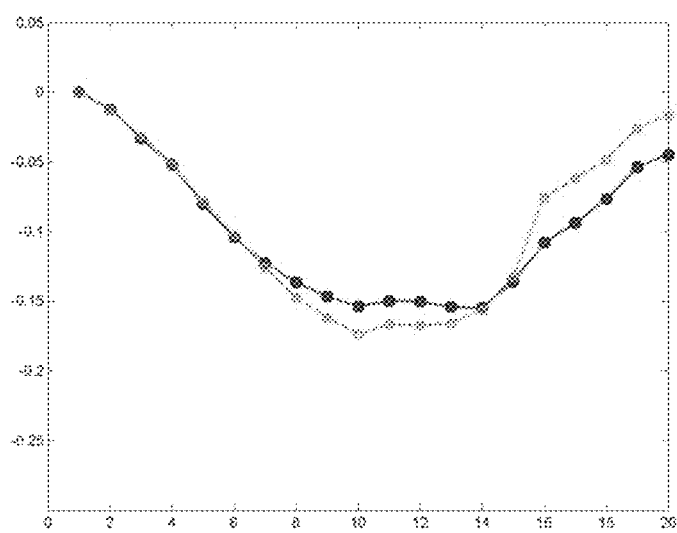
FIG. 51(c) is a graph showing calculated circumferential shortening percentage for slice 10 of data set 7.

Circumferential shortening is the relative change in length of a mid-wall contour with respect to the reference length at end-diastole.

$$\text{Circumferential Shortening} = \frac{L_{cur} - L_{ref}}{L_{ref}} \times 100\% \qquad (26)$$

where $L_{cur}$ is the mid-wall contour length at the current frame, and $L_{ref}$ is the mid-wall contour length at the reference frame. FIG. 38(a) to FIG. 51(c) show the circumferential shortening percentage (Equation 26) at different cardiac phases for different slices (from slice 2 to slice 10) for each data set. The red plots are the results from 3D SinMod and the green plots are the results from 3D HARP. There is a good degree of correspondence present. FIG. 38(a) to FIG. 38(f) show circumferential shortening for slices 2 to 7, respectively, during the cardiac cycle for data set 1. FIG. 39(a) to FIG. 39(c) show circumferential shortening for slices 8 to 10, respectively, during the cardiac cycle for data set 1. FIG. 40(a) to FIG. 40(f) show circumferential shortening for slices 2 to 7, respectively, during the cardiac cycle for data set 2. FIG. 41(a) to FIG. 41(c) show circumferential shortening for slices 8 to 10, respectively, during the cardiac cycle for data set 2. FIG. 42(a) to FIG. 42(f) show circumferential shortening for slices 2 to 7, respectively, during the cardiac cycle for data set 3. FIG. 43(a) to FIG. 43(c) show circumferential shortening for slices 8 to 10, respectively, during the cardiac cycle for data set 3. FIG. 44(a) to FIG. 44(f) show circumferential shortening for slices 2 to 7, respectively, during the cardiac cycle for data set 4. FIG. 45(a) to FIG. 45(c) show circumferential shortening for slices 8 to 10, respectively, during the cardiac cycle for data set 4. FIG. 46(a) to FIG. 46(f) show circumferential shortening for slices 2 to 7, respectively, during the cardiac cycle for data set 5. FIG. 47(a) to FIG. 47(c) show circumferential shortening for slices 8 to 10, respectively, during the cardiac cycle for data set 5. FIG. 48(a) to FIG. 48(f) show circumferential shortening for slices 2 to 7, respectively, during the cardiac cycle for data set 6. FIG. 49(a) to FIG. 49(c) show circumferential shortening for slices 8 to 10, respectively, during the cardiac cycle for data set 6. FIG. 50(a) to FIG. 50(f) show circumferential shortening for slices 2 to 7, respectively, during the cardiac cycle for data set 7. FIG. 51(a) to FIG. 51(c) show circumferential shortening for slices 8 to 10, respectively, during the cardiac cycle for data set 7.

Table 4 shows the average circumferential shortening error between the results from 3D SinMod and 3D HARP for slices 2 to 10 over all cardiac phases. The error is in percentage.

TABLE 4

|  | data 1 | data 2 | data 3 | data 4 | data 5 | data 6 | data 7 |
|---|---|---|---|---|---|---|---|
| slice 2 | 2.12 | 3.36 | 1.55 | 1.09 | 0.93 | 0.91 | 0.94 |
| slice 3 | 1.43 | 2.84 | 0.90 | 1.53 | 0.71 | 0.69 | 0.81 |
| slice 4 | 1.90 | 1.71 | 0.74 | 0.79 | 0.45 | 0.71 | 0.80 |
| slice 5 | 0.51 | 0.93 | 0.77 | 0.41 | 0.47 | 0.80 | 0.82 |
| slice 6 | 0.31 | 0.87 | 0.50 | 0.35 | 0.42 | 0.90 | 0.54 |
| slice 7 | 0.24 | 0.88 | 0.38 | 0.51 | 0.52 | 0.97 | 0.49 |
| slice 8 | 0.95 | 1.00 | 0.94 | 0.40 | 0.59 | 0.81 | 0.74 |
| slice 9 | 0.76 | 0.85 | 1.02 | 0.85 | 0.97 | 0.66 | 0.85 |
| slice 10 | 0.67 | 1.00 | 1.94 | 1.57 | 1.95 | 0.70 | 1.27 | c. Strains

In order to analyze regional strain patterns in the myocardium, the LV and RV are typically divided into segments and each of the directional strains (e.g., radial, circumferential, and/or longitudinal) is averaged over the segment. In 3D, the 16 segment and 17 segment models as recommended by the American Society of Echocardiography should be used [12]. In the 16 segment model, the LV is divided into 6 basal, 6 mid-ventricular, and 4 apical regions. In the 17 segment model, the apex comprises the 17th segment [13, 14, 15, 16, 17, 18, 19]. In 3D, the RV can be divided into 3 layers in the long-axis direction and each layer is further divided into 3 segments [14, 20]. However other finer or sparser partitions have also been utilized. For 2D analysis, typically, mid-ventricular strains for 4-8 regions are reported [21, 22, 23, 24].

Figure 52:
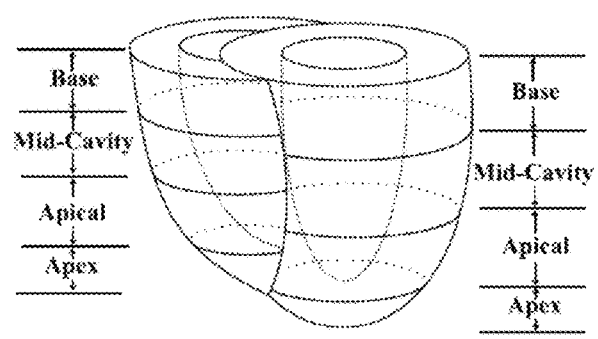
FIG. 52 is a schematic geometrical representation of the regional divisions for strain analysis for both the left and right ventricles in the LA view
Figures 53A, 53B, 53C:
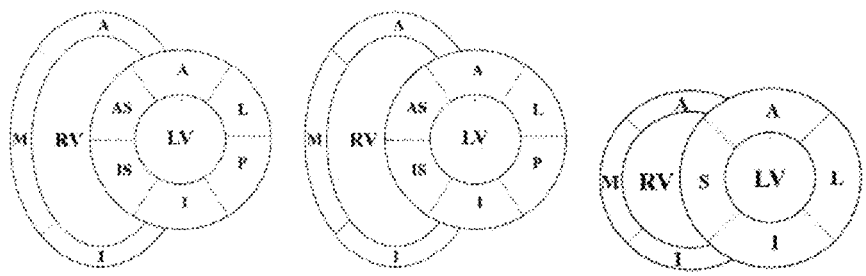
FIG. 53(a) is a schematic geometrical representation of the basal region division for strain analysis for both the left and right ventricles in the SA view.
FIG. 53(b) is a schematic geometrical representation of the mid-cavity region.
FIG. 53(c) is a schematic geometrical representation of the apical region.
Figure 54A:
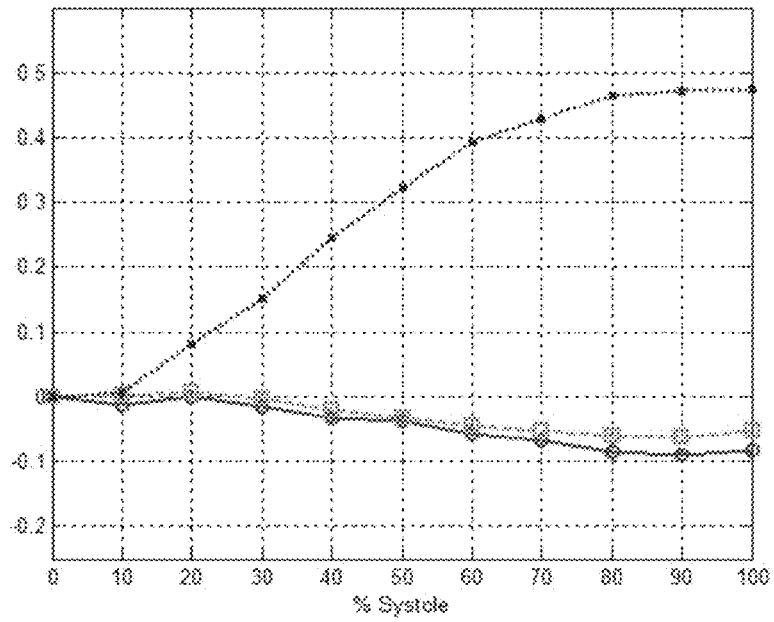
FIG. 54(a) to FIG. 54(f) are graphs of the average radial, circumferential, and longitudinal strain curves during systole for all 7 data sets.
Figure 54B:
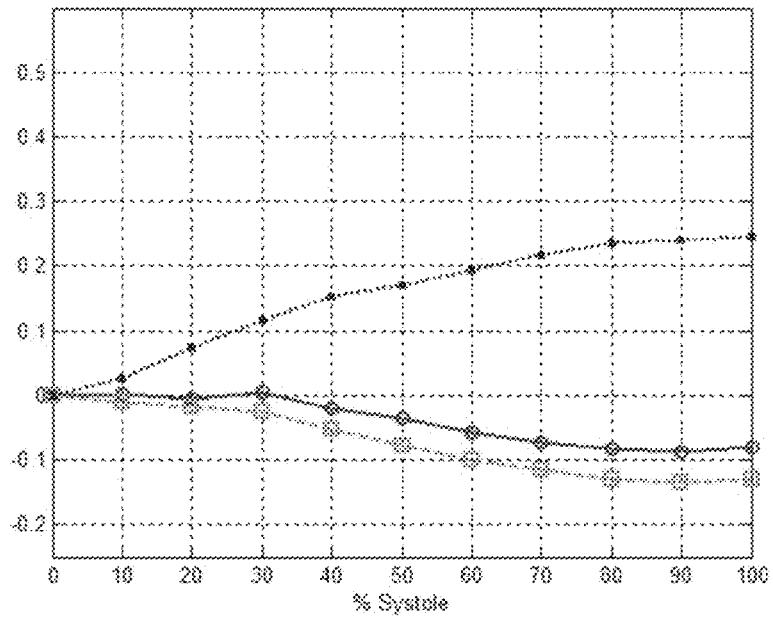
Figure 54C:
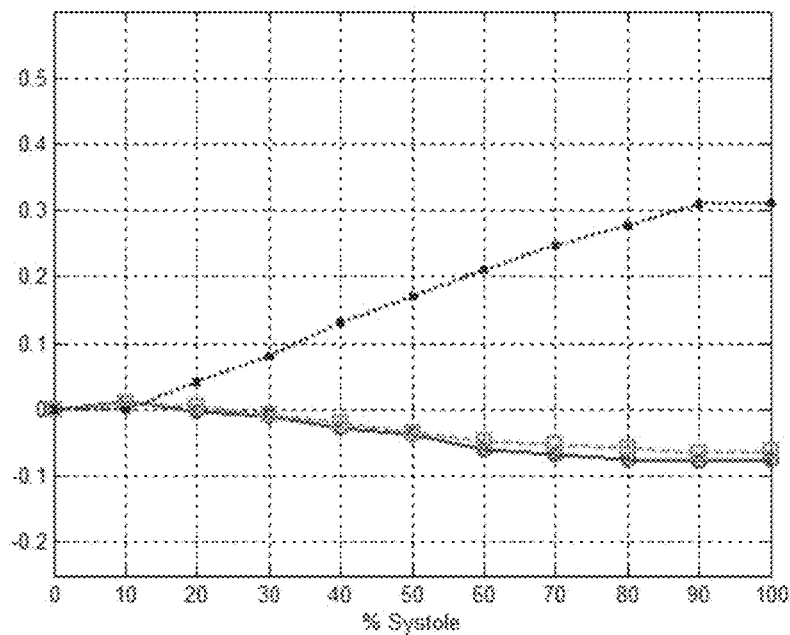
Figure 54D:
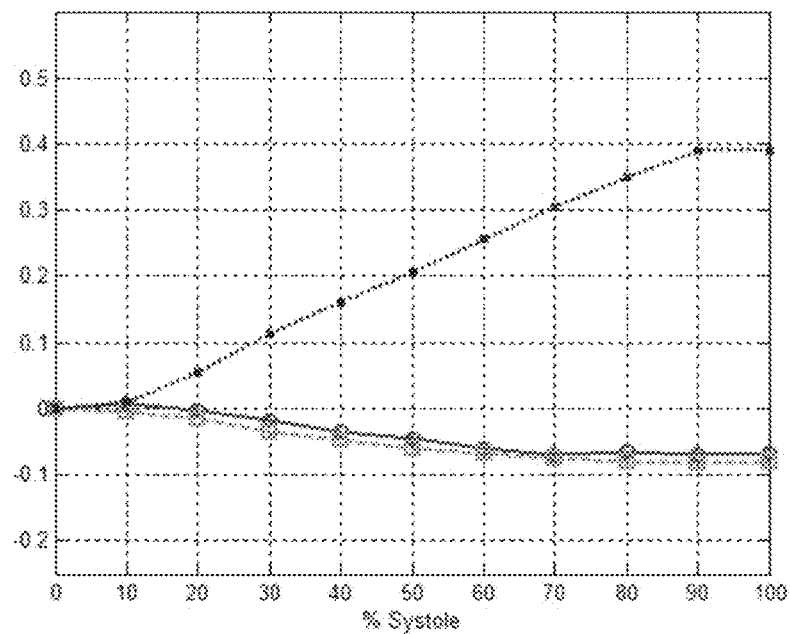
Figure 54E:
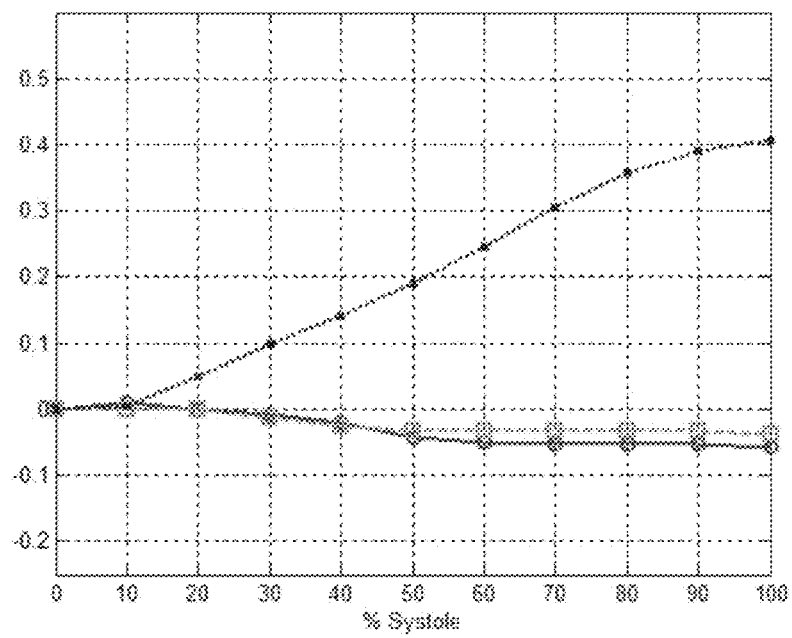
Figure 54F:
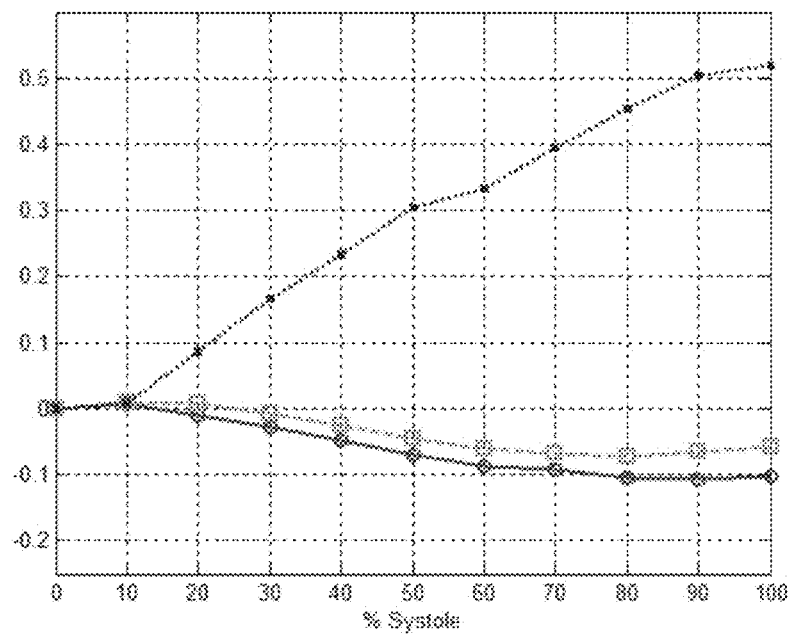
Figure 55A:
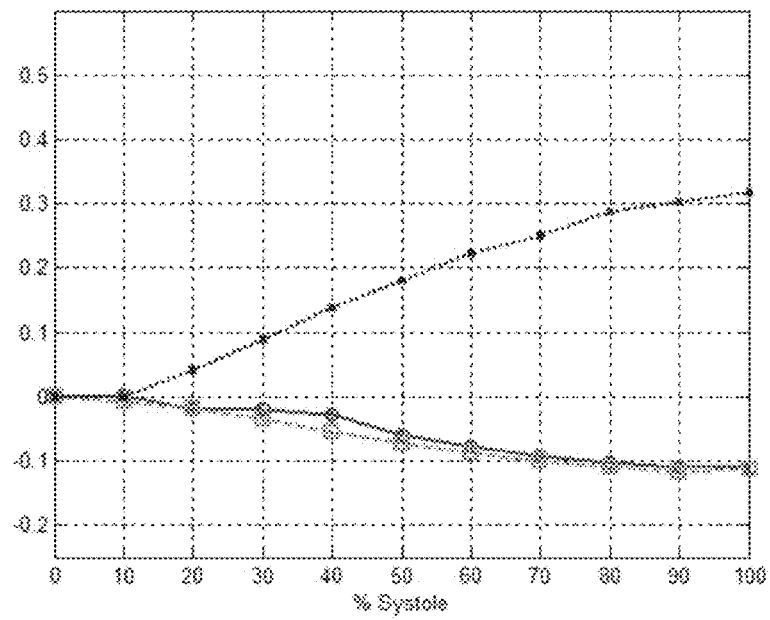
FIG. 55(a) to FIG. 55(f) are graphs of the average radial, circumferential, and longitudinal strain curves during systole for all 7 data sets.
Figure 55B:
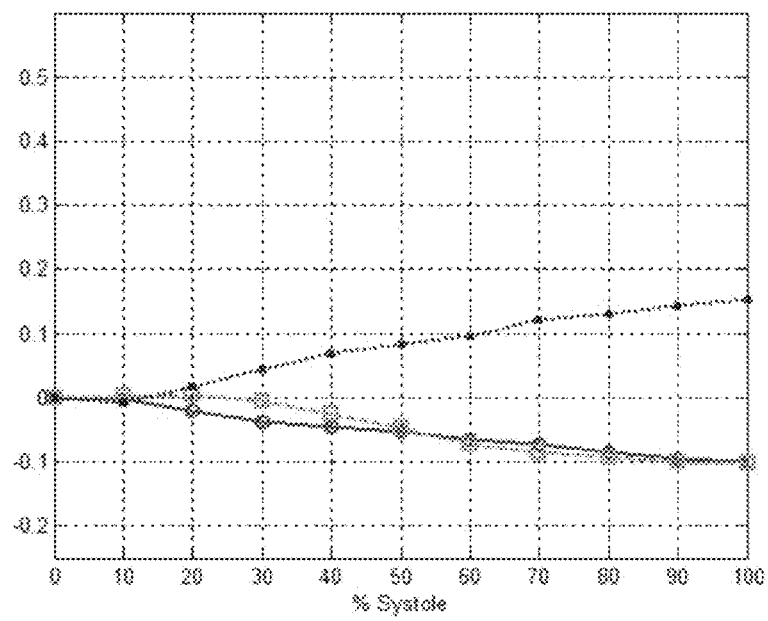
Figure 55C:
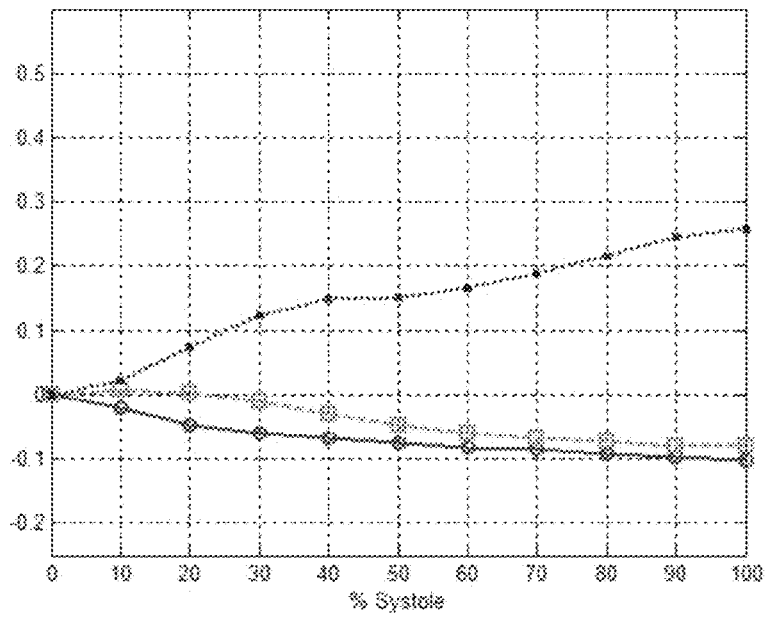
Figure 55D:
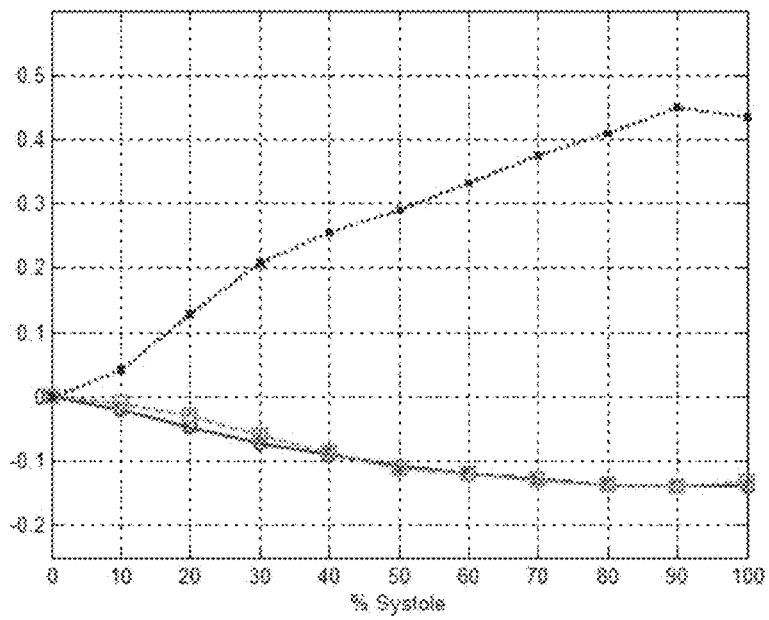
Figure 55E:
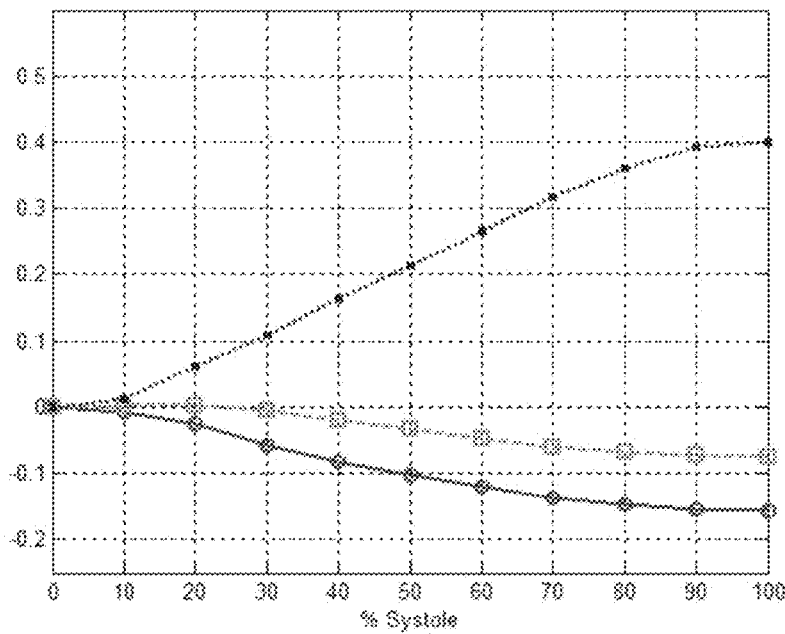
Figure 55F:
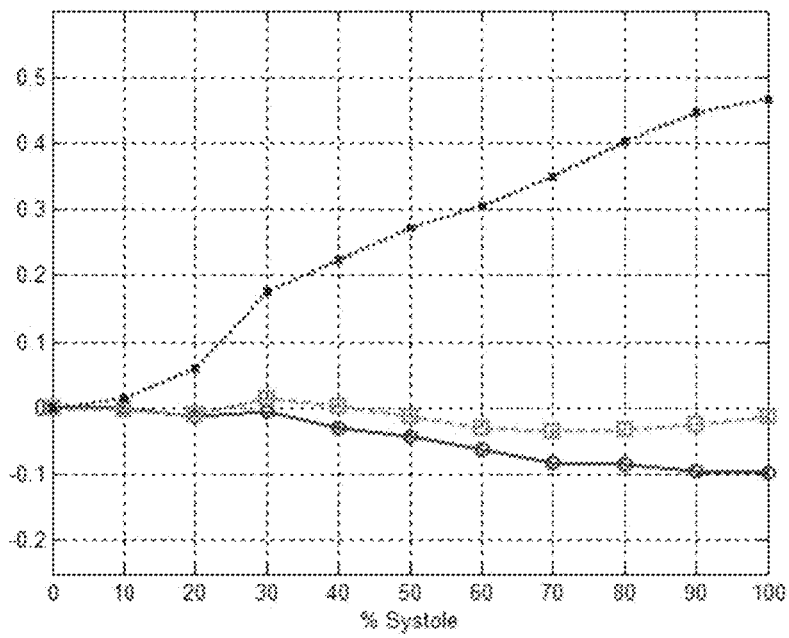
Figure 56A:
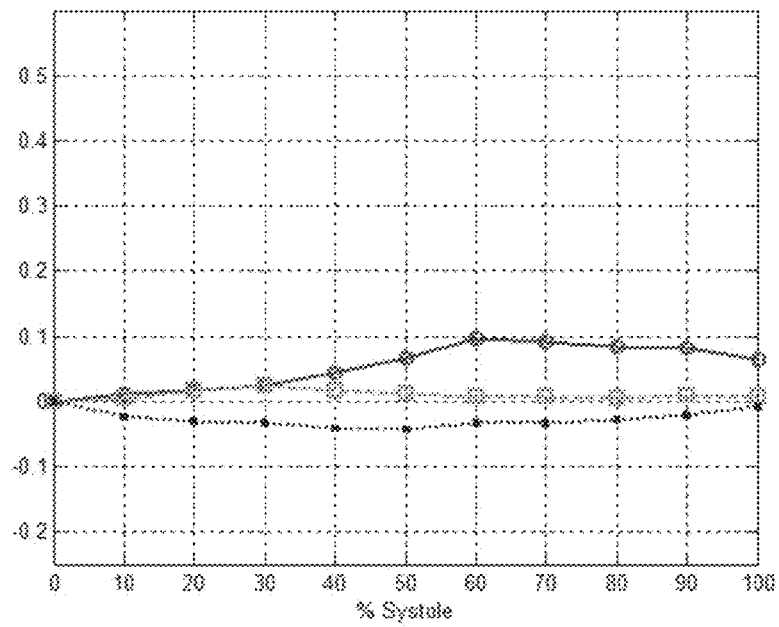
FIG. 56(a) to FIG. 56(e) are graphs of the average radial, circumferential, and longitudinal strain curves during systole for all 7 data sets.
Figure 56B:
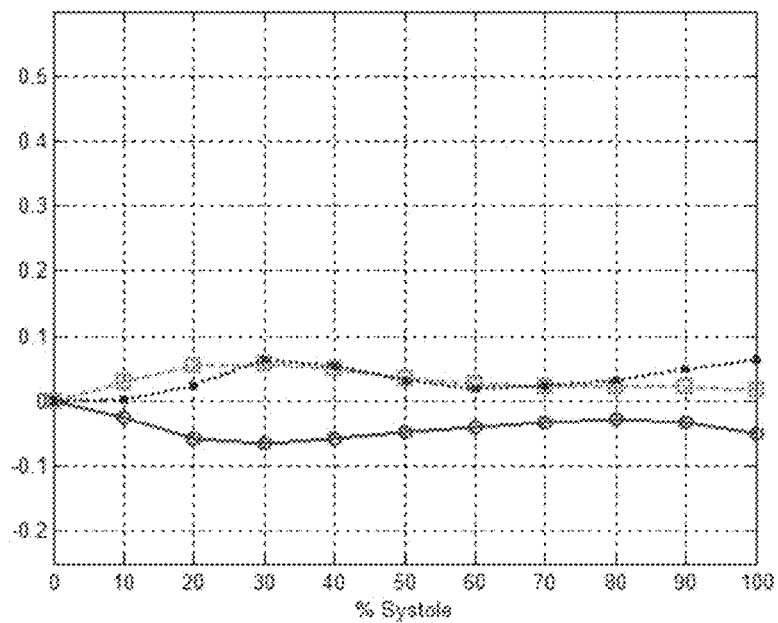
Figure 56C:
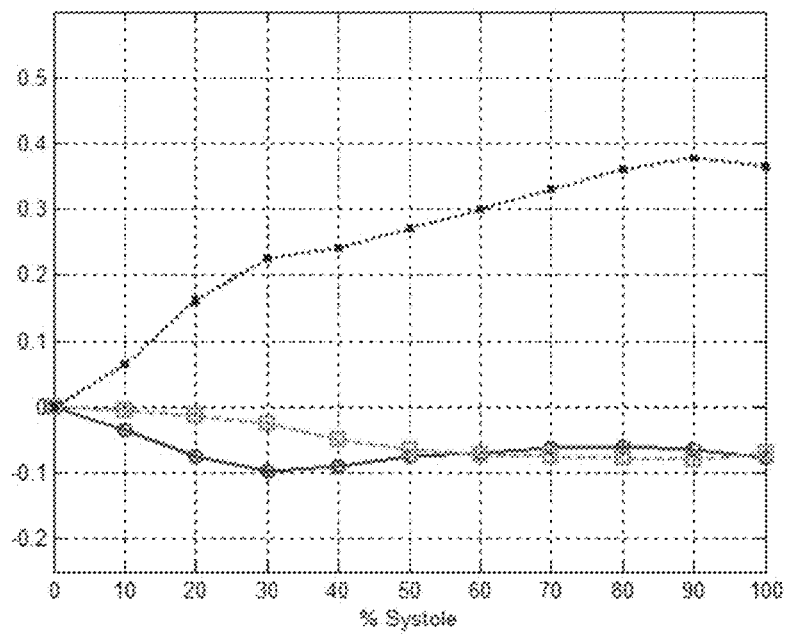
Figure 56D:
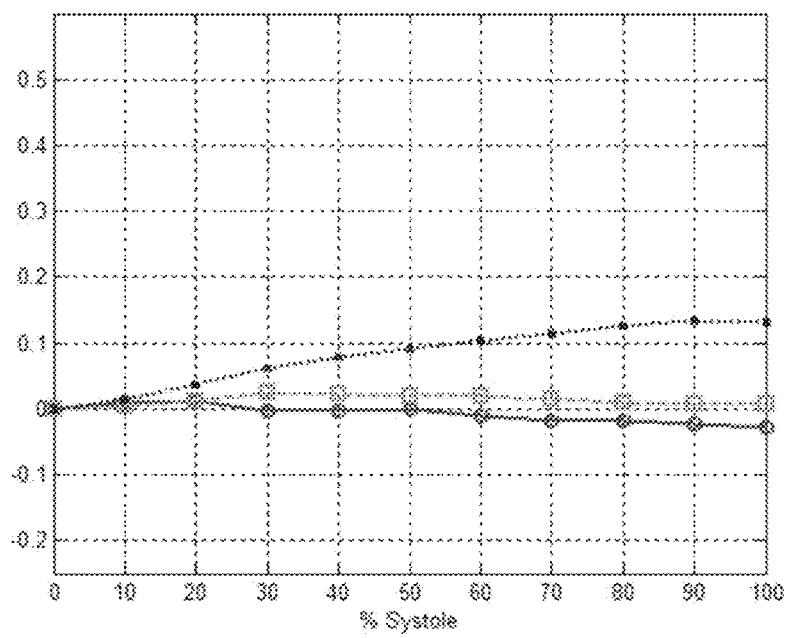
Figure 56E:
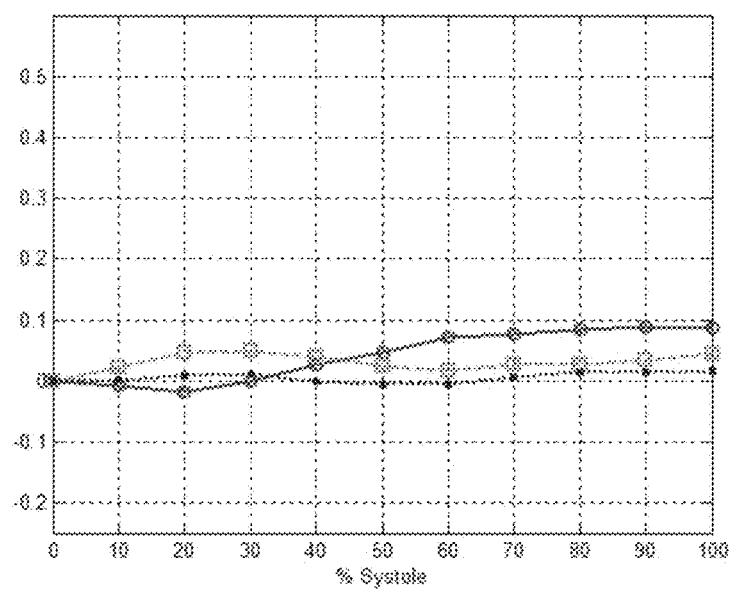

FIG. 52 shows a representation of the regional divisions for strain analysis for both the left and right ventricles in the LA view, as described in Tustison et al. [25]. The division along the long-axis consists of four layers: basal, mid-cavity, apical, and apex. Based on the location of the LV/RV junctions, the basal and mid-cavity portions of the left ventricle are each further divided into six regions in the short-axis view: anterior (A), antero-septal (AS), infero-septal (IS), inferior (I), posterior (P), and lateral (L) as shown in FIG. 53. The 17 segments refer to: basal anterior (segment 1), basal antero-septal (segment 2), basal infero-septal (segment 3), basal inferior (segment 4), basal posterior (segment 5), basal lateral (segment 6), mid-ventricular anterior (segment 7), mid-ventricular antero-septal (segment 8), mid-ventricular infero-septal (segment 9), mid-ventricular inferior (segment 10), mid-ventricular posterior (segment 11), mid-ventricular lateral (segment 12), apical anterior (segment 13), apical septal (segment 14), apical inferior (segment 15), apical lateral (segment 16), and apex (segment 17). Similar to the left ventricle, the right ventricle was divided into basal, mid-cavity, and apical layers and each layer was further divided into anterior, mid, and inferior regions. Tustison et al. [17] calculates both the Eulerian and Lagrangian strain values for LV data sets from three species: canine data, human data, and porcine data. The strain values from the RV for two canine data sets were also included. Results showed that across normal species, radial strains remain positive for most of the regions indicative of systolic thickening of the left ventricle while the circumferential and the longitudinal strains are negative. Circumferential shortening during left ventricular contraction results in the negative strain values in the circumferential direction while compression in the longitudinal direction results in negative longitudinal strains.

The average circumferential and longitudinal strain curves for different segments over systole averaged for all 7 data sets are shown in FIG. 54(a) to FIG. 56(e). As may be observed, radial strains are positive in accordance to systolic thickening of the LV myocardium, whereas the circumferential and longitudinal strains are negative, in accordance to circumferential and longitudinal shortening during systole. In the radial direction very few measurements are available and therefore as expected significant noise is present.

FIG. 54(a) to FIG. 54(f) show the average radial, circumferential, and longitudinal strain curves during systole for all 7 data sets. Radial strain is shown in dotted blue line. Circumferential strain is shown in dashed green line. Longitudinal strain is shown in solid red line. FIG. 54(a) to FIG. 54(f) are respective results for basal anterior (segment 1), basal antero-septal (segment 2), basal infero-septal (segment 3), basal inferior (segment 4), basal posterior (segment 5), basal lateral (segment 6).

FIG. 55(a) to FIG. 55(f) show the average radial, circumferential, and longitudinal strain curves during systole for all 7 data sets. Radial strain is shown in dotted blue line. Circumferential strain is shown in dashed green line. Longitudinal strain is shown in solid red line. FIG. 55(a) to FIG. 55(f) are respective results for mid-ventricular anterior (segment 7), mid-ventricular antero-septal (segment 8), mid-ventricular infero-septal (segment 9), mid-ventricular inferior (segment 10), mid-ventricular posterior (segment 11), mid-ventricular lateral (segment 12).

FIG. 56(a) to FIG. 56(e) show the average radial, circumferential, and longitudinal strain curves during systole for all 7 data sets. Radial strain is shown in dotted blue line. Circumferential strain is shown in dashed green line. Longitudinal strain is shown in solid red line. FIG. 56(a) to FIG. 56(e) are respective results for apical anterior (segment 13), apical septal (segment 14), apical inferior (segment 15), apical lateral (segment 16), and apex (segment 17).

10. Conclusions

Magnetic resonance imaging (MRI) is a highly advanced and sophisticated imaging modality for cardiac motion tracking and analysis, capable of providing 3D analysis of global and regional cardiac function with great accuracy and reproducibility. The anatomy and structure of the heart, fundamentals of continuum mechanics relevant to analysis of ventricular deformations, the basics of MRI, and MRI techniques for imaging cardiac function were discussed. A review of MR tagging techniques for imaging cardiac function was given. A novel 3D sine wave modeling (3D SinMod) approach to automatic analysis of 3D+t cardiac deformations from 3D CSPAMM acquisitions was proposed. The strength of this combined imaging/image analysis approach is the speed of acquisition (3 breath holds) for 3D+t acquisition of CSPAMM tagged data in 3 orthogonal orientations and 5-7 minutes for estimation of displacement and regional strains.

The novel 3D sine wave modeling (3D SinMod) method provides automatic analysis of 3D cardiac deformations [26]. An accelerated 3D complementary spatial modulation of magnetization (CSPAMM) tagging technique [11] was used to modulate the magnetization of the myocardial tissue and to acquire 3D MR data sets of the whole-heart including three orthogonal tags within three breath-holds. With the application of CSPAMM, the effect of tag fading encountered in SPAMM tagging due to $T_1$ relaxation is mitigated and tag deformations can be visualized for the entire cardiac cycle, including diastolic phases. In 3D SinMod, the intensity distribution around each pixel is modeled as a cosine wave front. The principle behind 3D SinMod tracking is that both phase and frequency for each voxel are determined directly from the frequency analysis and the displacement is calculated from the quotient of phase difference and local frequency. The deformation fields clearly demonstrate longitudinal shortening during systole. The contraction of the LV base towards the apex as well as the torsional motion between basal and apical slices is clearly observable from the displacements. The advantages of the method are as follows.

1. The entire framework, from data acquisition to data analysis is in the 3D domain, which permits quantification of both the in-plane and through-plane motion components.
2. The method does not require acquisitions in different cardiac views (SA and LA) and makes the image acquisition planning easier for technologists in hospital.
3. The method is automatic and fast. It requires no user-interaction and the computational time for a full 3D data with 20-24 cardiac phases is about 5-7 minutes. The average CPU time for calculating 3D motion fields between a pair of 3D volumes for each of the data sets was 17.37 seconds.

It will be understood that various details of the presently disclosed subject matter can be changed without departing from the scope of the subject matter disclosed herein. Furthermore, the foregoing description is for the purpose of illustration only, and not for the purpose of limitation.

Throughout this document, various references are cited. All such references are incorporated herein by reference, including the references set forth in the following list:

REFERENCES

[1] Texas Heart Institute, "Heart anatomy," http://www.texasheart.org/HIC/Anatomy/index.cfm.
[2] A. A. Amini and J. L. Prince, Measurement of Cardiac Deformations from MRI: Physical and Mathematical Models. Kluwer Academic Publishers, Dordrecht, The Netherlands, 2001.
[3] P. C. Lauterbur, "Image formation by induced local interactions: Examples employing nuclear magnetic resonance," Nature, vol. 242, pp. 190-191, March 1973.
[4] L. Axel and L. Dougherty, "MR imaging of motion with spatial modulation of magnetization," Radiology, vol. 171, no. 3, pp. 841-845, June 1989.
[5] T. D. Nguyen, S. J. Reeves, and T. S. Denney, Jr., "On the optimality of magnetic resonance tag patterns for heart wall motion estimation," IEEE Transactions on Image Processing, vol. 12, no. 5, pp. 524-532, 2003.
[6] V. M. Pai and L. Axel, "Advances in MRI tagging techniques for determining regional myocardial strain," Current Cardiology Reports, vol. 8, no. 1, pp. 53-58, 2006.
[7] M. L. Shehata, S. Cheng, N. F. Osman, D. A. Bluemke, and J. A. Lima, "Myocardial tissue tagging with cardiovascular magnetic resonance," Journal of Cardiovascular Magnetic Resonance, vol. 11, no. 55, pp. 1-12, December 2009.
[8] L. Axel and L. Dougherty, "Heart wall motion: improved method of spatial modulation of magnetization for MR imaging," Radiology, vol. 172, no. 2, pp. 349-350, 1989.
[9] S. E. Fischer, G. C. McKinnon, S. E. Maier, and P. Boesiger, "Improved myocardial tagging contrast," Magnetic Resonance in Medicine, vol. 30, no. 2, pp. 191-200, August 1993.
[10] T. Arts, F. W. Prinzen, T. Delhaas, J. Milles, A. Rossi, and P. Clarysse, "Mapping displacement and deformation of the heart with local sine wave modeling," IEEE Transactions on Medical Imaging, vol. 29, no. 5, pp. 1114-1123, May 2010.
[11] A. K. Rutz, S. Ryf, S. Plein, P. Boesiger, and S. Kozerke, "Accelerated whole-heart 3D CSPAMM for myocardial motion quantification," Magnetic Resonance in Medicine, vol. 59, no. 4, pp. 755-763, April 2008.
[12] M. D. Cerqueira, N. J. Weissman, V. Dilsizian, A. K. Jacobs, S. Kaul, W. K. Laskey, D. J. Pennell, J. A. Rumberger, T. Ryan, and M. S. Verani, "Standardized myocardial segmentation and nomenclature for tomographic imaging of the heart: A statement for healthcare professionals from the cardiac imaging committee of the council on clinical cardiology of the American heart association," Circulation, vol. 105, pp. 539-542, 2002.
[13] N. J. Tustison, V. G. Davila-Roman, and A. A. Amini, "Myocardial kinematics from tagged MRI based on a 4-D B-spline model," IEEE Transactions on Biomedical Engineering, vol. 50, no. 8, pp. 1038-1040, August 2003.
[14] N. J. Tustison and A. A. Amini, "Biventricular myocardial strains via non-rigid registration of anatomical NURBS models," IEEE Transactions on Medical Imaging, vol. 25, no. 1, pp. 94-112, January 2006.
[15] X. Deng and T. S. Denney, Jr., "Three-dimensional myocardial strain reconstruction from tagged MRI using a cylindrical B-spline model," IEEE Transactions on Medical Imaging, vol. 23, no. 7, pp. 861-867, July 2004.
[16] C. Xu, J. J. Pilla, G. Isaac, J. H. Gorman, A. S. Blom, R. C. Gorman, Z. Ling, and L. Dougherty, "Deformation analysis of 3D tagged cardiac images using an optical flow method," Journal of Cardiovascular Magnetic Resonance, vol. 12, no. 19, March 2010.
[17] L. Pan, J. L. Prince, J. A. C. Lima, and N. F. Osman, "Fast tracking of cardiac motion using 3D-HARP," IEEE Transactions on Biomedical Engineering, vol. 52, no. 8, pp. 1425-1435, August 2005.
[18] C. C. Moore, C. H. Lugo-Olivieri, E. R. McVeigh, and E. A. Zerhouni, "Three-dimensional systolic strain patterns in the normal human left ventricle: Characterization with tagged MR imaging," Radiology, vol. 214, no. 2, pp. 453-466, February 2000.
[19] C. C. Moore, E. R. McVeigh, and E. A. Zerhouni, "Quantitative tagged magnetic resonance imaging of the normal human left ventricle," Top Magnetic Resonance Imaging, vol. 11, no. 6, pp. 359-371, 2000.
[20] S. S. Klein, T. P. Graham, Jr., and C. H. Lorenz, "Noninvasive delineation of normal right ventricular contractile motion with magnetic resonance imaging myocardial tagging," Annals of Biomedical Engineering, vol. 26, no. 5, pp. 756-763, September-October 1998.
[21] S. Sampath, N. F. Osman, and J. L. Prince, "A combined harmonic phase and strain-encoded pulse sequence for measuring three-dimentional strain," Magnetic Resonance Imaging, vol. 27, no. 1, pp. 55-61, January 2009.
[22] S. Sampath and J. L. Prince, "Automatic 3D tracking of cardiac material markers using slice-following and harmonic-phase MRI," Magnetic Resonance Imaging, vol. 25, no. 2, pp. 197-208, February 2007.

[23] S. Sampath, J. A. Derbyshire, E. Atalar, N. F. Osman, and J. L. Prince, "Real-time imaging of two-dimensional cardiac strain using a harmonic phase magnetic resonance imaging (HARP-MRI) pulse sequence," Magnetic Resonance in Medicine, vol. 50, no. 1, pp. 154-163, July 2003.

[24] Z. Qian, D. N. Metaxas, and L. Axel, "Non-tracking-based 2D strain estimation in tagged MRI," in IEEE International Symposium on Biomedical Imaging: Nano to Macro, vol. 1, May 2008, pp. 711-714.

[25] N. J. Tustison, "Biventricular myocardial strains with anatomical NURBS models from tagged MRI," Ph.D. dissertation, Washington University in St. Louis, August 2004.

[26] H. Wang and A. A. Amini, "Cardiac deformation analysis using 3D sinmod from 3D CSPAMM tagged MRI," in Proceedings of SPIE Medical Imaging 2013: Biomedical Applications in Molecular, Structural, and Functional Imaging, Mar. 29, 2013.

What is claimed is:

1. A method for analysis of 3D deformations and regional function of a heart comprising:
   receiving, by an image processing device, three sets of 3D plus time volumetric data with mutually perpendicular tag lines of a volume of a heart;
   modeling in 3D, by the image processing device, using the three sets of 3D plus time volumetric data, a neighborhood around each voxel in the volume as a moving sine wave front with local frequency and amplitude, separately, in each of x, y, and z directions as:

$$V_1(x, y, z) = A_1 \cos\left(\omega_x\left(x + \frac{u}{2}\right) + \varphi\right) + n_1(x, y, z)$$

$$V_2(x, y, z) = A_2 \cos\left(\omega_x\left(x + \frac{u}{2}\right) + \varphi\right) + n_2(x, y, z)$$

where:
   $\omega x$ and $\varphi$ are the spatial frequency and phase of the wave, respectively;
   $A_1$ and $A_2$ are wave magnitudes for a 3D volume $V_1$ and a short time later, a 3D volume $V_2$;
   $n_1$ and $n_2$ are additive noise; and
   u is the displacement between these two volumes at position (x, y, z) along the x direction; and
   the displacements v and w in the y and z directions have a corresponding formulation; and further wherein the 3D plus time volumetric data comprises 3D plus time volumetric data of one or more mid-wall contour deformation of the heart at the beginning of systole, 3D plus time volumetric data of one or more mid-wall contour deformations of the heart at end-systole, or both, and further wherein the one or more mid-wall contour deformation of the heart at the beginning of systole, the one or more mid-wall contour deformations of the heart at end-systole, or both are tracked by 3D SinMod; and
   determining, using the image processing device, phase and frequency of the moving sine wave front for each voxel directly from the local frequency and amplitude and a 3D displacement from a quotient of phase difference and local frequency, thereby resulting in 3D deformation information for each voxel, wherein at least some of the 3D deformation information indicates a heart deformation involving a twisting motion combined with longitudinal shortening and wall thickening.

2. The method of claim 1, wherein each of the three sets of 3D plus time volumetric data is acquired, by a magnetic resonance imaging (MRI) scanner, using a 3D complementary spatial modulation of magnetization (3D CSPAMM) tagging technique.

3. The method of claim 2, wherein the 3D CSPAMM tagging technique includes rotating, by the MRI scanner, a tagging gradient in such a way as to acquire 3D+t data with orthogonal tags.

4. The method of claim 1, wherein determining the phase and frequency for each voxel and the displacement comprises:
   Fourier transforming, by the image processing device, the 3D volume $V_1(x, y, z)$ and the 3D volume $V_2(x, y, z)$ in a first tagging direction;
   applying, by the image processing device, identical 3D band-pass filters to the Fourier-transformed volumes to isolate corresponding spectral peaks and produce two complex volumes in the Fourier domain, $V_{bf1}(\omega_x; \omega_y, \omega_z)$ and $V_{bf2}(\omega_x, \omega_y, \omega_z)$;
   applying, by the image processing device, a low frequency band-pass filter and a high frequency band-pass filter to the two complex volumes in the Fourier domain, followed by an inverse Fourier transform to produce four complex volumes, $V_{bfLf1}(x, y, z)$, $V_{bfHf1}(x, y, z)$, $V_{bfLf2}(x, y, z)$, and $V_{bfHf2}(x, y, z)$;
   determining, by the image processing device, the power spectra and cross power spectrum given by:

$$P_{Lf}(x,y,z) = |V_{bfLf1}|^2 + |V_{bfLf2}|^2$$

$$P_{Hf}(x,y,z) = |V_{bfHf1}|^2 + |V_{bfHf2}|^2$$

$$P_{cc}(x,y,z) = V_{bfLf1}\overline{V}_{bfLf2} + V_{bfHf1}\overline{V}_{bfHf2}$$

where $\overline{V}$ is the complex conjugate of V;
   determining, by the image processing device, the local frequency $\omega_x$ and local displacement u from:

$$\omega_x(x, y, z) = \omega_c \sqrt{\frac{P_{Hf}}{P_{Lf}}} \quad u(x, y, z) = \frac{\arg(P_{cc})}{\omega_x}$$

where $\omega_c$ is the band-pass center-frequency;
   up-sampling, by the image processing device, the local displacement to the initial size of the volume; and
   repeating the same steps for the other tagging directions to produce full 3D displacements.

5. The method of claim 1, wherein the one or more mid-wall contour deformation of the heart at the beginning of systole, the one or more mid-wall contour deformations of the heart at end-systole, or both are compared using a motion field from a 3D SinMod. algorithm with 3D HARP.

6. The method of claim 1, further comprising generating average radial, circumferential, and longitudinal strain curves during systole.

7. The method of claim 6, wherein the average radial, circumferential, and longitudinal strain curves comprise strain curves for one or more regions of the heart selected from the group consisting of mid-ventricular anterior, mid-ventricular antero-septal, mid-ventricular infero-septal, mid-ventricular inferior, mid-ventricular posterior, and mid-ventricular lateral, or any combination thereof.

8. The method of claim 7, wherein the average radial, circumferential, and longitudinal strain curves comprise strain curves for each of the mid-ventricular anterior, mid-ventricular antero-septal, mid-ventricular infero-septal, mid-ventricular inferior, mid-ventricular posterior, and mid-ventricular lateral regions of the heart.

9. A system for analysis of 3D deformations and regional function of a heart comprising:
a magnetic resonance imaging (MRI) scanner configured to acquire three sets of 3D plus time volumetric data with mutually perpendicular tag lines of a volume of a heart;
a data storage device in communication with the MRI scanner and configured to store the three sets of 3D plus time volumetric data; and
an image processing device in communication with data storage device and configured to:
model in 3D, using the three sets of 3D plus time volumetric data, a neighborhood around each voxel in the volume as a moving sine wave front with local frequency and amplitude, separately, in each of x, y, and z directions as:

$$V_1(x, y, z) = A_1 \cos\left(\omega_x\left(x + \frac{u}{2}\right) + \varphi\right) + n_1(x, y, z)$$

$$V_2(x, y, z) = A_2 \cos\left(\omega_x\left(x + \frac{u}{2}\right) + \varphi\right) + n_2(x, y, z)$$

where:
$\omega x$ and $\varphi$ are the spatial frequency and phase of the wave, respectively;
$A_1$ and $A_2$ are wave magnitudes for a 3D volume $V_1$ and a short time later, a 3D volume $V_2$;
$n_1$ and $n_2$ are additive noise; and
u is the displacement between these two volumes at position (x, y, z) along the x direction; and
the displacements v and w in the y and z directions have a corresponding formulation; and further wherein the 3D plus time volumetric data comprises 3D plus time volumetric data of one or more mid-wall contour deformation of the heart at the beginning of systole, 3D plus time volumetric data of one or more mid-wall contour deformations of the heart at end-systole, or both, and further wherein the one or more mid-wall contour deformation of the heart at the beginning of systole, the one or more mid-wall contour deformations of the heart at end-systole, or both are tracked by 3D SinMod; and
determine phase and frequency of the moving sine wave front for each voxel directly from the local frequency and amplitude and a 3D displacement from a quotient of phase difference and local frequency, thereby resulting in 3D deformation information for each voxel, wherein at least some of the 3D deformation information indicates a heart deformation involving a twisting motion combined with longitudinal shortening and wall thickening.

10. The system of claim 9, wherein the MRI scanner acquires each of the three sets of 3D plus time volumetric data using a 3D complementary spatial modulation of magnetization (3D CSPAMM) tagging technique.

11. The system of claim 10, wherein the MRI scanner, performing the 3D CSPAMM tagging technique, rotates a tagging gradient in such a way as to acquire 3D+t data with orthogonal tags.

12. The system of claim 9, wherein the image processing device determines the phase and frequency for each voxel and the displacement by:
Fourier transforming the 3D volume $V_1(x, y, z)$ and the 3D volume $V_2(x, y, z)$ in a first tagging direction;
applying identical 3D band-pass filters to the Fourier-transformed volumes to isolate corresponding spectral peaks and produce two complex volumes in the Fourier domain, $V_{bf1}(\omega_y, \omega_y, \omega_z)$ and $V_{bf2}(\omega_x, \omega_y, \omega_z)$;
applying a low frequency band-pass filter and a high frequency band-pass filter to the two complex volumes in the Fourier domain, followed by an inverse Fourier transform to produce four complex volumes, $V_{bfLf1}(x, y, z)$, $V_{bfHf1}(x, y, z)$, $V_{bfLf}(x, y, z)$, and $V_{bfHf2}(x, y, z)$;
determining the power spectra and cross power spectrum given by:

$$P_{Lf}(x,y,z) = |V_{bfLf1}|^2 + |V_{bfLf2}|^2$$

$$P_{Hf}(x,y,z) = |V_{bfHf1}|^2 + |V_{bfHf2}|^2$$

$$P_{cc}(x,y,z) = V_{bfLf1}\overline{V}_{bfLf2} + V_{bfHf1}\overline{V}_{bfHf2}$$

where $\overline{V}$ is the complex conjugate of V;
determining the local frequency $\omega_x$ and local displacement u from:

$$\omega_x(x, y, z) = \omega_c \sqrt{\frac{P_{Hf}}{P_{Lf}}} \quad u(x, y, z) = \frac{\arg(P_{cc})}{\omega_x}$$

where $w_c$ is the band-pass center-frequency;
up-sampling the local displacement to the initial size of the volume; and
repeating the same steps for the other tagging directions to produce full 3D displacements.

* * * * *